United States Patent [19]
Castro Pineiro et al.

[11] Patent Number: 5,618,812
[45] Date of Patent: Apr. 8, 1997

[54] BENZODIAZEPINE DERIVATIVES

[75] Inventors: Jose L. Castro Pineiro, Harlow; William R. Carling, Bishops Stortford; Mark S. Chambers, Watford; Stephen R. Fletcher, Hatfield Heath, Nr. Bishops Stortford; Sarah C. Hobbs, Bishops Stortford; Victor G. Matassa, Furneux Pelham; Kevin W. Moore, Buntingford; Graham A. Showell, Welwyn Garden City; Michael G. Russell, Welwyn Garden City, all of United Kingdom

[73] Assignee: Merck Sharp & Dohme, Ltd., Hoddesdon, England

[21] Appl. No.: 374,748

[22] PCT Filed: Jul. 28, 1993

[86] PCT No.: PCT/GB93/01599
§ 371 Date: Jan. 26, 1995
§ 102(e) Date: Jan. 26, 1995

[87] PCT Pub. No.: WO94/03437
PCT Pub. Date: Feb. 17, 1994

[30] Foreign Application Priority Data

| Jul. 29, 1992 | [GB] | United Kingdom | 9216123 |
| Jul. 30, 1992 | [GB] | United Kingdom | 9216231 |
| Jul. 30, 1992 | [GB] | United Kingdom | 9216238 |
| Oct. 6, 1992 | [GB] | United Kingdom | 9220957 |
| Oct. 30, 1992 | [GB] | United Kingdom | 9222821 |
| Nov. 2, 1992 | [GB] | United Kingdom | 9222934 |
| Nov. 11, 1992 | [GB] | United Kingdom | 9223583 |
| Dec. 16, 1992 | [GB] | United Kingdom | 9226242 |
| Dec. 17, 1992 | [GB] | United Kingdom | 9226360 |
| Jan. 22, 1993 | [GB] | United Kingdom | 9301277 |
| Apr. 7, 1993 | [GB] | United Kingdom | 9307318 |

[51] Int. Cl.⁶ .......... A61K 31/55; C07D 401/04; C07D 403/04
[52] U.S. Cl. .......... 514/221; 540/509
[58] Field of Search .......... 540/509; 514/221

[56] References Cited

U.S. PATENT DOCUMENTS

| 5,302,591 | 4/1994 | Fletcher et al. | 514/221 |
| 5,360,802 | 11/1994 | Chambers et al. | 514/221 |

FOREIGN PATENT DOCUMENTS

| 0434369A1 | 6/1991 | European Pat. Off. |
| 0434364A2 | 6/1991 | European Pat. Off. |
| 0539170A1 | 4/1993 | European Pat. Off. |
| 0545478A1 | 6/1993 | European Pat. Off. |
| 93/12791 | 7/1993 | WIPO |

OTHER PUBLICATIONS

"Benzodiazepine Gastrin and Brain Cholecystokinin Receptor Ligands: L–365,260", Mark G. Bock, et al., Journal of Medicinal Chemistry, vol. 32, No. 1, Jan. 1989, pp. 13–16.
Mol. Pharm. vol. 46, 943–948, 1994, "Biological Properties of . . . L–740,093, . . . " by S. Patel et al.

Primary Examiner—Philip I. Datlow
Attorney, Agent, or Firm—Robert J. North; Melvin Winokur

[57] ABSTRACT

Compounds of Formula (I), and salts and prodrugs thereof, wherein $R^1$ represents H, optionally substituted $C_{1-6}$alkyl or $C_{3-7}$cycloalkyl; $R^2$ is $NHR^{12}$ or $(CH_2)_xR^{13}$ where 5 is 0, 1 or 2; $R^3$ represents $C_{1-6}$alkyl, halo or $NR^6R^7$; $R^4$ and $R^5$ are H, $C_{1-12}$alkyl optionally substituted by $NR^9R^{9'}$ or an azacyclic or azabicyclic group, optionally substituted $C_{4-9}$cycloalkyl, $C_{4-9}$cycloalkyl $C_{1-4}$alkyl, aryl, aryl$C_{1-6}$alkyl or azacyclic or azabicyclic groups, or $R^4$ and $R^5$ together form the residue of an optionally substituted azacyclic or azabicyclic ring system; x is 0, 1, 2 or 3; $R^{12}$ is optionally substituted phenyl or pyridyl; $R^{13}$ represents a group (A) wherein $R^{14}$ is H or $C_{1-6}$alkyl; $R^{15}$ is H, $C_{1-6}$alkyl, halo or $NR^6R^7$; and the dotted line is an optional covalent bond; are CCK and/or gastrin antagonists useful in therapy.

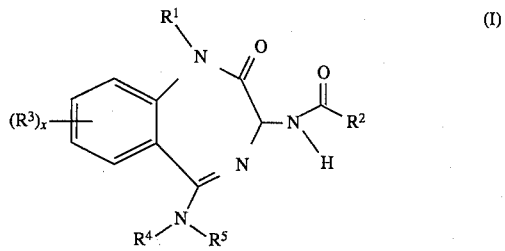

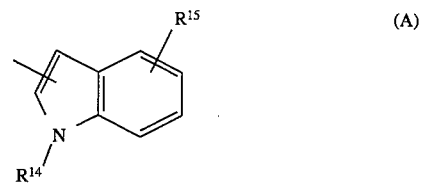

18 Claims, No Drawings

BENZODIAZEPINE DERIVATIVES

This is a national stage application under 35USC371 of international application PCT/GB93/01599, filed Jul. 28, 1993.

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, New York, p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33[1982] and references cited therein; J. A. Williams, *Biomed Res.* 3 107[1982]; and J. E. Morley, *Life Sci.* 30, 479[1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin receptors: implications for behavioural actions", *Brain Res.*, 362, 175–79[1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; cervo et. al., 1988, *Eur. J. Pharmacol*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485[1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application no. 0 167 919 discloses benzodiazepine CCK and gastrin antagonists substituted in the 3-position by, inter alia, a phenyl urea or an indole amide and at the 5-position by an optionally substituted phenyl or pyridyl group.

U.S. Pat. No. 3,414,563 discloses benzodiazepine derivatives optionally substituted at the 3-position by $C_{1-4}$alkyl or phenyl and substituted at the 5-position by an amino, alkylamino or dialkylamino group or a 3 to 8-membered azacycle, bound through nitrogen, which azacycle may optionally contain a further O, S or N atom. The compounds are said to have CNS activity. There is no suggestion of a nitrogen-containing substitutuent at the 3-position. Nor is there any suggestion that the disclosed compounds are antagonists at CCK or gastrin receptors.

The present invention provides benzodiazepine compounds of formula (I):

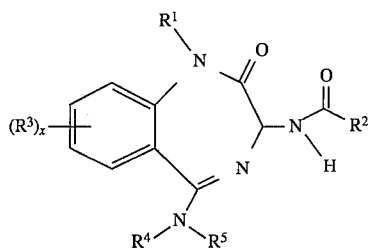

wherein:

R$^1$ represents H, C$_{1-6}$alkyl optionally substituted by one or more halo, C$_{3-7}$cycloalkyl, cyclopropylmethyl, (CH$_2$)$_r$imidazolyl, (CH$_2$)$_r$triazolyl, (CH$_2$)$_r$tetrazolyl (where r is 1, 2 or 3), CH$_2$CO$_2$R$^{11}$ (where R$^{11}$ is C$_{1-4}$alkyl) or CH$_2$CONR$^6$R$^7$ (where R$^6$ and R$^7$ each independently represents H or C$_{1-4}$alkyl, or R$^6$ and R$^7$ together form a chain (CH$_2$)$_p$ where p is 4 or 5);

R$^2$ represents NHR$^{12}$ or (CH$_2$)$_s$R$^{13}$ where s is 0, 1 or 2;

R$^3$ represents C$_{1-6}$alkyl, halo or NR$^6$R$^7$, where R$^6$ and R$^7$ are as previously defined;

R$^4$ and R$^5$ each independently represents H, C$_{1-12}$alkyl optionally substituted by NR$^9$R$^{9'}$ (where R$^9$ and R$^{9'}$ are as previously defined) or an azacyclic or azabicyclic group, C$_{4-9}$cycloalkyl optionally substituted by one or more C$_{1-4}$alkyl groups, C$_{4-9}$cycloalkylC$_{1-4}$alkyl optionally substituted in the cycloalkyl ring by one or more C$_{1-4}$alkyl groups, optionally substituted aryl, optionally substituted arylC$_{1-6}$alkyl or azacyclic or azabicyclic groups, or R$^4$ and R$^5$ together form the residue of an optionally substituted azacyclic or azabicyclic ring system;

x is 0, 1, 2 or 3;

R$^{12}$ represents a phenyl or pyridyl group optionally substituted by one or more substituents selected from C$_{1-6}$alkyl, halo, hydroxy, C$_{1-4}$alkoxy, (CH$_2$)$_q$-tetrazolyl optionally substituted in the tetrazole ring by C$_{1-4}$alkyl, (CH$_2$)$_q$-imidazolyl, (CH$_2$)$_q$-triazolyl (where q is 0, 1, 2 or 3), 5-hydroxy-4-pyrone, NR$^6$R$^7$, NR$^9$COR$^{11}$, NR$^9$CONR$^{9'}$R$^{11}$ (where R$^9$ and R$^{9'}$ are each independently H or C$_{1-4}$alkyl and R$^{11}$ is as previously defined), CONR$^6$R$^7$ (where R$^6$ and R$^7$ are as previously defined), SO(C$_{1-6}$alkyl), SO$_2$(C$_{1-6}$alkyl), trifluoromethyl, CONHSO$_2$R$^8$, SO$_2$NHCOR$^8$ (where R$^8$ is C$_{1-6}$alkyl, optionally substituted aryl, 2,2-difluorocyclopropane or trifluoromethyl), SO$_2$NHR$^{10}$ (where R$^{10}$ is a nitrogen containing heterocycle), B(OH)$_2$, (CH$_2$)$_q$CO$_2$H, where q is as previously defined; or R$^{12}$ represents a group

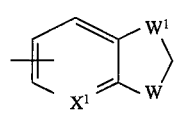

where X$^1$ represents CH or N; W represents CH$_2$ or NR$^9$, where R$^9$ is as previously defined, and W$^1$ represents CH$_2$, or W and W$^1$ each represent O; or R$^{12}$ represents phenyl substituted by a group

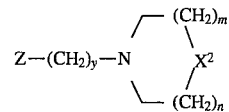

wherein X$^2$ is O, S or NR$^9$, where R$^9$ is as previously defined; Z is a bond, O or S; m is 1, 2 or 3; n is 1, 2 or 3; and y is 0, 1, 2 or 3;

R$^{13}$ represents a group

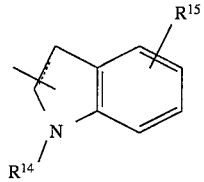

wherein R$^{14}$ represents H or C$_{1-6}$alkyl; R$^{15}$ represents H, C$_{1-6}$alkyl, halo or NR$^6$R$^7$, where R$^6$ and R$^7$ are a previously defined; and the dotted line represents an optional covalent bond;

and pharmaceutically acceptable salts or prodrugs thereof, with the proviso that, when NR$^4$R$^5$ represents an unsubstituted azacyclic ring system, R$^2$ does not represent NHR$^{12}$ where R$^{12}$ is optionally substituted phenyl or

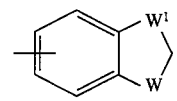

It will be appreciated that formula (I) is intended to embrace all possible isomers, including optical isomers, and mixtures thereof, including racemates.

As used herein, the definition of each expression, when it occurs more than once in any structure, is intended to be independent of its definition elsewhere in the same structure.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

Halo includes fluoro, chloro, bromo and iodo. Preferably halo will be fluoro or chloro.

As used herein, unless otherwise indicated, alkyl means straight or branched chain saturated hydrocarbon.

As used herein, azacyclic means non-aromatic nitrogen-containing monocyclic, and azabicyclic means non-aromatic nitrogen-containing bicyclic.

Unless otherwise stated, aryl means optionally substituted carbocyclic or heterocyclic aromatic groups, especially phenyl.

Heteroaryl means aromatic rings preferably having 5 or 6 ring atoms and containing at least one atom selected from O, S and N.

A first subgroup of compounds according to the invention is represented by compounds of formula (I), and salts and prodrugs thereof, wherein R$^1$ represents C$_{1-6}$alkyl, C$_{3-7}$cycloalkyl, cyclopropylmethyl, CH$_2$CO$_2$R$^{11}$ or CH$_2$CONR$^6$R$^7$; R$^2$ represents NHR$^{12}$ where R$^{12}$ represents a phenyl group optionally substituted by one or more substituents selected from C$_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl, 5-hydroxy-4-pyrone, $NR^6R^7$, $NR^9COR^{11}$, $NR^9CONR^9'R^{11}$, $CONR^6R^7$, $SO(C_{1-6}alkyl)$, $SO_2(C_{1-6}alkyl)$, trifluoromethyl, $CONHSO_2R^8$, $SO_2NHCOR^8$, $SO_2NHR^{10}$, $B(OH)_2$ and $(CH_2)_tCO_2H$, where t is zero, 1 or 2; or $R^{12}$ represents a group

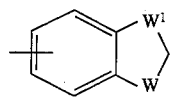

and $NR^4R^5$ represents a group

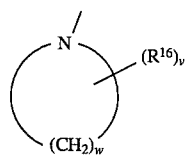

wherein each $R^{16}$ independently represents $C_{1-6}$alkyl, $C_{1-6}$alkoxy, hydroxy, oxo, $SR^{11}$, $NR^6R^7$, $NR^9C_{1-4}alkylR^{17}$, $=NOR^9$ or

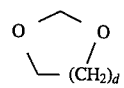

where $R^{11}$, $R^6$, $R^7$ and $R^9$ are as previously defined, $R^{17}$ is halo or trifluoromethyl, and d is 2 or 3; v is 1, 2, 3, 4, 5, 6, 7 or 8; and w is 4, 5, 6, 7, 8, 9, 10 or 11.

Within the abovementioned subgroup of compounds according to the invention there may be identified a subclass of compounds of formula (I), and salts and prodrugs thereof, wherein $R^{12}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl, 5-hydroxy-4-pyrone, $NR^6R^7$, $NR^9COR^{11}$, $NR^9COR^9'R^{11}$, $CONR^6R^7$, $SO(C_{1-6}alkyl)$, $SO_2(C_{1-6}alkyl)$, trifluoromethyl, $CONHSO_2R^8$, $SO_2NHCOR^8$, $SO_2NHR^{10}$, $B(OH)_2$ and $(CH_2)_tCO_2H$; or $R^{12}$ represents a group

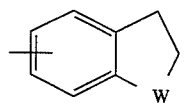

where W represents $CH_2$ or $NR^9$; $R^{16}$ represents $C_{1-6}$alkyl, $C_{1-6}$alkoxy, hydroxy, oxo, $SR^{11}$, $NR^6R^7$, $NR^9C_{1-4}alkylR^{17}$, $=NOR^9$ or $OR^{18}$ $OR^{19}$, where $R^{18}$ and $R^{19}$ each independently represent $C_{1-4}$alkyl or $R^{18}$ and $R^{19}$ together form a chain $CH_2CH_2$ or $CH_2CH_2CH_2$; and v is 1.

A second subgroup of compounds according to the invention is represented by compounds of formula (I), and salts and prodrugs thereof, wherein $R^1$ represents H, $C_{1-6}$alkyl, $C_{3-7}$cycloalkyl, cyclopropylmethyl, $(CH_2)_r$imidazolyl, $(CH_2)_r$triazolyl, $(CH_2)_r$tetrazolyl, $CH_2CO_2R^{11}$ or $CH_2CONR^6R^7$; $R^2$ is $NHR^{12}$ where $R^{12}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl, 5-hydroxy-4-pyrone, $NR^6R^7$, $NR^9COR^{11}$, $NR^9CONR^9'R^{11}$, $CONR^6R^7$, $SO(C_{1-6}alkyl)$, $SO_2(C_{1-6}alkyl)$, trifluoromethyl, $CONHSO_2R^8$, $SO_2NHCOR^8$, $SO_2NHR^{10}$, $B(OH)_2$ and $(CH_2)_qCO_2H$; or $R^{12}$ represents a group

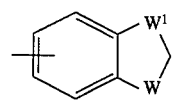

and $R^4$ and $R^5$ together form the residue of a bridged azabicyclic ring system.

Within the abovementioned second subgroup of compounds according to the invention there may be identified a subclass of compounds of formula (I), and salts and prodrugs thereof, wherein $R^1$ represents $C_{1-6}$alkyl, $C_{3-7}$cycloalkyl, cyclopropylmethyl, $CH_2CO_2R^{11}$ or $CH_2CONR^6R^7$; and $R^{12}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl, 5-hydroxy-4-pyrone, $NR^6R^7$, $NR^9COR^{11}$, $NR^9COR^9'R^{11}$, $CONR^6R^7$, $SO(C_{1-6}alkyl)$, $SO_2(C_{1-6}alkyl)$, trifluoromethyl, $CONHSO_2R^8$, $SO_2NHCOR^8$, $SO_2NHR^{10}$, $B(OH)_2$ and $(CH_2)_tCO_2H$, where t is zero, 1 or 2; or $R^{12}$ represents a group

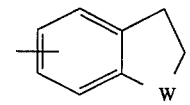

where W represents $CH_2$ or $NR^9$.

A third subgroup of compounds according to the invention is represented by compounds of formula (I), and salts and prodrugs thereof, wherein $R^1$ represents H, $C_{1-6}$alkyl, $C_{3-7}$cycloalkyl, cyclopropylmethyl, $CH_2CO_2R^{11}$ or $CH_2CONR^6R^7$, $R^{12}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl, 5-hydroxy-4-pyrone, $NR^6R^7$, $NR^9COR^{11}$, $NR^9CONR^9'R^{11}$, $CONR^6R^7$, $SO(C_{1-6}alkyl)$, $SO_2$ $(C_{1-6}alkyl)$, trifluoromethyl, $R^{12}$ represents a group

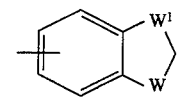

and $R^4$ and $R^5$ are independently selected from H, $C_{1-12}$alkyl, $C_{4-9}$cycloalkyl$(CH_2)_k$ optionally substituted by one or more $C_{1-4}$alkyl groups, bridged $C_{6-10}$bicycloalkyl, $(CH_2)_kR^{20}$ (where $R^{20}$ is $NR^6R^7$ as previously defined, or an azacyclic or azabicyclic group and k is 0, 1, 2, 3 or 4), optionally substituted aryl, and optionally substituted aryl$C_{1-6}$alkyl.

Within this third subgroup of compounds according to the invention there may be identified a subclass of compounds of formula (I), and salts and prodrugs thereof, wherein $R^1$ represents $C_{1-6}$alkyl, $C_{3-7}$cycloalkyl, cyclopropylmethyl, $CH_2CO_2R^{11}$ or $CH_2CONR^6R^7$; and $R^{12}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl, 5-hydroxy-4-pyrone $NR^6R^7$, $NR^9COR^{11}$, $NR^9COR^9R^{11}$, $CONR^6R^7$, $SO(C_{1-6}$alkyl), $SO_2(C_{1-6}$alkyl), trifluoromethyl, $CONHSO_2R^8$, $SO_2NHCOR^8$, $SO_2NHR^{10}$, $B(OH)_2$ and $(CH_2)_tCO_2H$, where t is zero, 1 or 2; or $R^{12}$ represents a group

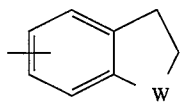

where W represents $CH_2$ or $NR^9$; and $R^4$ and $R^5$ are independently selected from H, $C_{1-12}$alkyl, $C_{4-9}$cycloalkyl, optionally substituted aryl, optionally substituted aryl$C_{1-6}$alkyl, and azacyclic and azabicyclic groups.

A fourth subgroup of compounds according to the invention is represented by compounds of formula (I), and salts and prodrugs thereof, wherein $R^1$ represents $C_{1-6}$alkyl, $C_{3-7}$cycloalkyl, cyclopropylmethyl, $CH_2CO_2R^{11}$ or $CH_2CONR^6R^7$; $R^2$ represents $NHR^{12}$ where $R^{12}$ represents phenyl substituted by a group

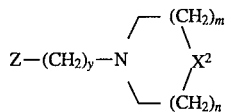

and $R^4$ and $R^5$ each independently represents H, $C_{1-12}$alkyl, $C_{4-9}$cycloalkyl, optionally substituted aryl, optionally substituted aryl$C_{1-6}$alkyl or an azacyclic or azabicyclic group, or $R^4$ and $R^5$ together form the residue of an azacyclic or a bridged azabicyclic ring system.

A fifth subgroup of compounds according to the invention is represented by compounds of formula (I), and salts and prodrugs thereof, wherein $R^1$ represents H, $C_{1-6}$alkyl, $C_{3-7}$cycloalkyl, cyclopropylmethyl, $(CH_2)_r$imidazolyl, $(CH_2)_r$triazolyl, $(CH_2)_r$tetrazolyl, $CH_2CO_2R^{11}$ or $CH_2CONR^6R^7$; $R^2$ represents $NHR^{12}$ where $R^{12}$ represents a pyridyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl, 5-hydroxy-4-pyrone, $NR^6R^7$, $NR^9COR^{11}$, $NR^9CONR^9R^{11}$, $CONR^6R^7$, $SO(C_{1-6}$alkyl), $SO_2(C_{1-6}$alkyl), trifluoromethyl, $CONHSO_2R^8$, $SO_2NHCOR^8$, $SO_2NHR^{10}$, $B(OH)_2$ and $(CH_2)_qCO_2H$; or $R^{12}$ represents a group

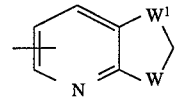

and $R^4$ and $R^5$ each independently represents H, $C_{1-12}$alkyl, $C_{4-9}$cycloalkyl optionally substituted by one or more $C_{1-4}$alkyl groups, $C_{4-9}$cycloalkyl$C_{1-4}$alkyl, optionally substituted aryl, optionally substituted aryl$C_{1-6}$alkyl or an azacyclic or azabicyclic group, or $R^4$ and $R^5$ together form the residue of an optionally substituted azacyclic or a bridged azabicyclic ring system.

A sixth subgroup of compounds according to the invention is represented by compounds of formula (I), and salts and prodrugs thereof, wherein $R^1$ represents H, $C_{1-6}$alkyl, $C_{3-7}$cycloalkyl, cyclopropylmethyl, $(CH_2)_r$imidazolyl, $(CH_2)_r$triazolyl, $(CH_2)_r$tetrazolyl, $CH_2CO_2R^{11}$ or $CH_2CONR^6R^7$; $R^2$ represents $(CH_2)_sR^{13}$; and $R^4$ and $R^5$ together form the residue of an azacyclic or azabicyclic ring system.

A seventh subgroup of compounds according to the invention is represented by compounds of formula (I), and salts and prodrugs thereof, wherein $R^1$ represents H, $C_{1-6}$alkyl, $C_{3-7}$cycloalkyl, cyclopropylmethyl, $(CH_2)_r$imidazolyl, $(CH_2)_r$triazolyl, $(CH_2)_r$tetrazolyl, $CH_2CO_2R^{11}$ or $CH_2CONR^6R^7$; $R^2$ is $NHR^{12}$ where $R^{12}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$-triazolyl, 5-hydroxy-4-pyrone, $NR^6R^7$, $NR^9COR^{11}$, $NR^9CONR^9R^{11}$, $CONR^6R^7$, $SO(C_{1-6}$alkyl), $SO_2(C_{1-6}$alkyl), trifluoromethyl, $CONHSO_2R^8$, $SO_2NHCOR^8$, $SO_2NHR^{10}$, $B(OH)2$ and $(CH_2)_qCO_2H$; or $R^{12}$ represents a group

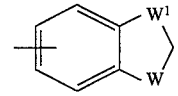

and $R^4$ and $R^5$ together form the residue of a fused or spiro azabicyclic ring system.

When $R^1$ is $C_{3-7}$cycloalkyl, suitable cycloalkyl groups include cyclopropyl, cyclopentyl and cyclohexyl groups, preferably cyclopropyl.

Preferably $R^1$ represents $C_{1-6}$alkyl optionally substituted by one or more halo, such as $C_{1-4}$alkyl optionally substituted by one, two or three fluoro. Preferred values for $R^1$ include methyl, ethyl, n-propyl, i-propyl, i-butyl and 2,2,2-trifluoroethyl.

When $R^2$ represents $NHR^{12}$ and $R^{12}$ represents phenyl or pyridyl substituted by $CONHSO_2R^8$ or $SO_2NHCOR^8$, suitable values for $R^8$ include $C_{1-6}$alkyl, optionally substituted aryl and trifluoromethyl.

When $R^8$ is optionally substituted aryl, this will preferably be optionally substituted phenyl. Suitable substituents include $C_{1-4}$alkyl, $C_{1-4}$alkoxy, halo and trifluoromethyl. Preferred is unsubstituted phenyl or phenyl substituted by $C_{1-6}$alkyl, such as methyl, for example, phenyl substituted by $C_{1-6}$alkyl in the ortho position.

When $R^8$ is $C_{1-6}$alkyl, it will preferably represent $C_{1-4}$alkyl. Particularly preferred are methyl and iso-propyl, especially iso-propyl.

When $R^{12}$ is phenyl or pyridyl substituted by $SO_2NHR^{10}$, suitable values of $R^{10}$ include, for example, thiazole, thiadiazole and pyrazine.

Preferably q is zero.

When $R^2$ represents $NHR^{12}$, and $R^{12}$ represents optionally substituted phenyl or pyridyl, the substituents will preferably be selected from $C_{1-6}$alkyl, such as methyl and ethyl, halo, such as chloro, bromo, fluoro and iodo, and trifluoromethyl.

When $R^{12}$ represents monosubstituted phenyl, the substituent will preferably be located at the 3- or 4-position of the phenyl ring, more preferably at the 3-position. When $R^{12}$ represents disubstituted phenyl the substituents will preferably be located at the 3- and 4-positions of the phenyl ring.

When $R^{12}$ represents optionally substituted pyridyl it will preferably represent optionally substituted 3-pyridyl. When $R^{12}$ represents monosubstituted 3-pyridyl, the substituent will preferably be located at the 5-position of the pyridyl ring.

When $R^{12}$ represents a group

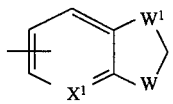

where $X^1$ is CH the fused 5-membered ring will preferably be fused across the 3- and 4-positions of the phenyl ring and where $X^1$ is N the 5-membered ring will preferably be fused across the 4- and 5-positions of the phenyl ring.

Preferably W and $W^1$ are $CH_2$.

When $R^{12}$ represents phenyl substituted by a group

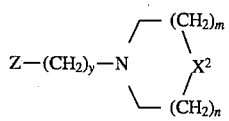

the substituent will preferably be located at the 3- or 4-position of the phenyl ring, more preferably at the 3-position.

Preferably m is 1 or 2, more preferably 1.
Preferably n is 1 or 2, more preferably 1.
Preferably y is 0 or 1, more preferably 0.
Suitable values for $X^2$ include O, S, NH and $NCH_3$.
Preferably Z represents a bond.

When $R^2$ represents $(CH_2)_sR^{13}$, s is preferably 0 or 1, more preferably 0, $R^{14}$ is preferably H and $R^{15}$ is preferably H. The optional covalent bond may suitably be either present or absent, preferably present.

Particularly preferred are compounds of formula (I) wherein $R^2$ represents $NHR^{12}$ and $R^{12}$ represents phenyl substituted by one or two substituents selected from $C_{1-6}$alkyl, halo and trifloromethyl; or $R^{12}$ represents

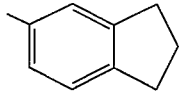

Suitable values for $R^3$ include methyl and dimethylamino.

Preferably x is 0 or 1, more preferably 0.

When $R^4$ or $R^5$ represents optionally substituted aryl or optionally substituted aryl$C_{1-6}$alkyl, suitable aryl groups include phenyl, thienyl, furyl, pyrrolyl and pyridyl, preferably phenyl. Suitable aryl substituents include, for example, $C_{1-4}$alkyl, $C_{1-4}$alkoxy, halo and trifluoromethyl.

When $R^4$ or $R^5$ represents an azacyclic or azabicyclic group, or $C_{1-6}$alkyl substituted by an azacyclic or azabicyclic group, the azacyclic or azabicyclic group may contain, in addition to the nitrogen atom, a further heteroatom selected from O and S, or a group $NR^{21}$, where $R^{21}$ is H or $C_{1-4}$alkyl.

When $R^4$ or $R^5$ represents an azacyclic group or $C_{1-6}$alkyl substituted by an azacyclic group, the azacyclic group will suitably contain from 5 to 10 ring atoms.

When $R^4$ or $R^5$ represents an azabicyclic group or $C_{1-6}$alkyl substituted by an azabicyclic group, the azabicyclic group will suitably contain from 7 to 10 ring atoms.

When $R^4$ or $R^5$ represents $C_{4-9}$cycloalkyl substituted by one or more $C_{1-4}$alkyl groups or $C_{4-9}$cycloalkyl$C_{1-4}$alkyl substituted in the cycloalkyl ring by one or more $C_{1-4}$alkyl groups, the $C_{1-4}$alkyl groups may be located on any available ring carbon atom. In particular, geminal disubstitution is provided for. The $C_{1-4}$alkyl groups will preferably be methyl groups.

Suitably $R^4$ and $R^5$ are selected from H, $C_{1-6}$alkyl, such as methyl, ethyl and n-propyl, $C_{4-9}$cycloalkyl, such as cyclopentyl, cyclohexyl, cycloheptyl and cyclooctyl, optionally substituted by one or more methyl groups, $C_{4-9}$cycloalkyl$C_{1-4}$alkyl, such as cyclohexylmethyl, aryl$C_{1-6}$alkyl, such as benzyl, $C_{1-6}$alkyl substituted by $NR^9R^9$, such as $CH_2CH_2N(CH_3)_2$, $C_{1-6}$alkyl substituted by an azacyclic group, such as $C_{1-4}$alkyl substituted by morpholinyl, and azacyclic groups, such as N-methylpiperidine.

When $R^4$ and $R^5$ together form the residue of an azacyclic or azabicyclic ring system, the azacyclic or azabicyclic ring system may contain, in addition to the nitrogen atom to which $R^4$ and $R^5$ are attached, a second heteroatom selected from O, S or a group $NR^{22}$ where $R^{22}$ is H $C_{1-4}$alkyl, $CO_2R^a$, $COR^a$ or $SO_2R^a$ where $R^a$ is $C_{1-6}$alkyl, optionally substituted phenyl or benzyl optionally substituted in the phenyl ring by one or more substituents, where the phenyl substituents are selected from $C_{1-4}$alkyl, $C_{1-4}$alkoxy, halo and trifluoromethyl.

When $R^4$ and $R^5$ together form the residue of an azacyclic ring system, the ring system may be substituted by one or more groups selected from $C_{1-6}$alkyl, $C_{1-6}$alkoxy, hydroxy, halo, trifluoromethyl, oxo, $SR^{11}$, $NR^6R^7$, $NR^9C_{1-4}$alkyl$R^{23}$, $=NOR^9$ or $$\underset{(CH_2)_b}{O \diagup \diagdown O}$$

where $R^6$, $R^7$, $R^9$ and $R^{11}$ are as previously defined, $R^{23}$ is halo or trifluoromethyl, and b is 2 or 3. The substituents may be located on any available carbon atom. In particular, geminal disubstitution is provided for where appropriate. Particularly suitable substituents include oxo, ketyl, $C_{1-6}$alkyl, $C_{1-6}$alkoxy, trifluoromethyl and $NHC_{1-4}$alkyl$CF_3$ groups. Preferred are $C_{1-6}$alkyl groups, especially methyl.

When $R^4$ and $R^5$ form the residue of an azacyclic ring system, the ring system suitably contains from 5 to 10 ring atoms, preferably 6, 7 or 8 ring atoms, more preferably 7 ring atoms.

When $R^4$ and $R^5$ together form the residue of an azabicyclic ring system, the azabicyclic ring system may be fused, spiro or bridged, preferably fused or bridged, more preferably bridged. The azabicyclic ring system may optionally be substituted by one or more $C_{1-4}$alkyl, such as methyl, groups. The alkyl substituents may be located on any available carbon atoms of the azabicyclic ring system. In particular, geminal disubstitution is provided for.

Preferably the azabicyclic ring system is unsubstituted.

Suitably the azabicyclic ring system contains from 7 to 10 ring atoms, preferably 7, 8 or 9 ring atoms.

Particularly preferred are compounds of formula (I) wherein $R^4$ and $R^5$ together form the residue of an azacyclic ring system substituted by one or more methyl groups, or $R^4$ and $R^5$ together form the residue of a bridged azabicyclic ring system, especially 3-azabicyclo[3.2.2]nonan-3-yl.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic acids or bases. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The present invention also encompasses a pharmaceutical composition comprising a compound of formula (I), or a salt or prodrug thereof and a pharmaceutically acceptable carrier.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression such as depression resulting from organic disease, secondary to stress associated with personal loss, or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occurring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0,005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 mg/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) wherein $R^2$ is $NHR^{12}$ may be prepared by reaction of intermediates of formula (II) with compounds of formula (III)

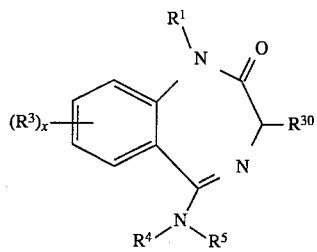

(II)

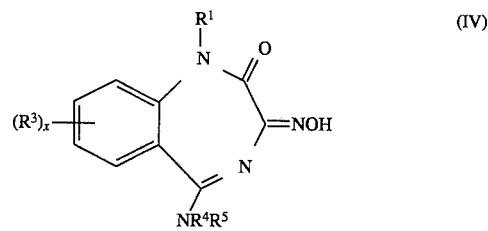

wherein $R^1$, $R^3$, $R^4$, $R^5$, $R^{12}$ and x are as defined for formula (I) above, one of $R^{30}$ and $R^{31}$ represents $NH_2$ and the other of $R^{30}$ and $R^{31}$ represents $-N=C=O$.

The reaction is conveniently effected in a suitable organic solvent, such as an ether, for example, tetrahydrofuran.

The compounds of formula (I) wherein $R^2$ is $(CH_2)_sR^{13}$ may be prepared by reaction of intermediates of formula (II) wherein $R^{30}$ is $NH_2$ (hereinafter intermediates (IIA)) with compounds of formula $HOC(=O)(CH_2)_sR^{13}$, wherein s and $R^{13}$ are as previously defined, in the presence of a base and a coupling reagent.

Suitable bases of use in the reaction include tertiary amines such as, for example, triethylamine.

A preferred coupling agent for use in the reaction is 1-(3-dimethylaminopropyl)-3-ethyl-carbodiimide hydrochloride (EDC), preferably in the presence of 1-hydroxybenzotriazole.

The reaction is conveniently effected in a suitable organic solvent, such as, for example, dimethylformamide.

Intermediates of formula (IIA) may be prepared from compounds of formula (IV):

(IV)

wherein $R^1$, $R^2$, $R^3$, $R^4$, $R^5$ and x are as defined for formula (I) above, by reduction, for example, by catalytic hydrogenation or reduction using a suitable metal under acidic conditions.

Suitable hydrogenation catalysts include, for example, nobel metal catalysts, e.g. ruthenium, or rhodium which may be supported, for example, on carbon.

The reaction is preferably conducted in a suitable organic solvent, such as an alcohol, for example, methanol, at elevated temperature, e.g. about 60° C.

Suitable reduction methods using metals include, for example, the use of zinc and trifluoroacetic acid in a suitable solvent, such as acetic acid, preferably at elevated temperature, e.g. at about 40° C.

Preferably, intermediates of formula (IIA) may be prepared from compounds of formula (V)

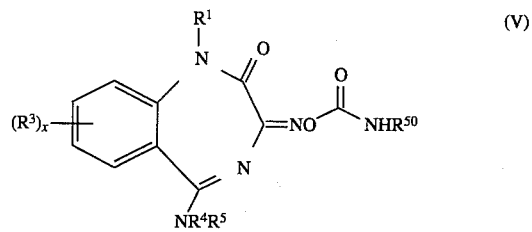

(V)

wherein $R^1$, $R^2$, $R^3$, $R^4$, $R^5$ and x are as defined for formula (I) and $R^{50}$ represents $C_{1-4}$alkyl, by reduction, for example, by catalytic hydrogenation.

Suitable hydrogenation catalysts include, for example, nobel metal catalysts, such as palladium, which may be supported, for example, on carbon.

The reaction is conveniently conducted in a suitable organic solvent, such as an alcohol, for example, methanol, suitably at ambient temperature.

Intermediates of formula (II) wherein $R^{30}$ is —N=C=O (hereinafter intermediates (IIB)) may be prepared from amines of formula (IIA) by reaction with triphosgene in the presence of a base, such as a tertiary amine, for example, triethylamine. The reaction is conveniently effected in a suitable organic solvent, such as an ether, for example, tetrahydrofuran, suitably at low temperature, such as about 0° C.

Intermediates of formula (V) may be prepared from intermediates of formula (IV) by reaction with a compound of formula $R^{50}N=C=O$, wherein $R^{50}$ is as previously defined.

The reaction is conveniently effected in a suitable organic solvent, such as an ether, for example, tetrahydrofuran, suitably at elevated temperature, for example, about 60° C.

Intermediates of formula (IV) may be prepared from compounds of formula (VI)

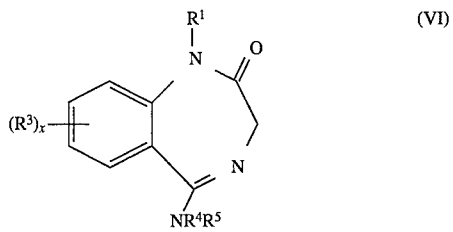

wherein $R^1$, $R^2$, $R^3$, $R^4$, $R^5$ and x are as defined for formula (I), by reaction with isoamyl nitrite in the presence of a base.

Suitable bases of use in the reaction include alkali metal alkoxides, such as potassium t-butoxide.

Compounds of formula (VI) may be prepared from compounds of formula (VII)

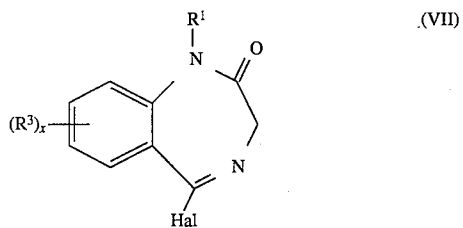

wherein $R^1$, $R^3$ and x are as defined for formula (I) and Hal represents halo, such as chloro, by reaction with an amine of formula $HNR^4R^5$.

Compounds of formula (VII) may be prepared as described in United Kingdom Patent Specification no. 1,145,471.

Compounds of formula (III) wherein $R^{31}$ is —N=C=O (IIIB) may be prepared from the corresponding compounds of formula (III) wherein $R^{31}$ is $NH_2$ (IIIA) analogously to the preparation of compounds of formula (IIB) from compounds of formula (IIA).

Compounds of formula (IIIA) and $HOC(=O)(CH_2)_xR^{13}$ are commercially available or may be prepared from commercially available starting materials by known methods.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following non-limiting examples are provided to assist in a further understanding of the invention.

EXAMPLE 1

N-[3(R,S)-2,3-Dihydro-5-(1,4-dioxa-8-azaspiro[4,5]decan-8-yl)-2-oxo-1-propyl-1H-1,4-benzodiazepin-3-yl]N'-[3-methylphenyl]urea a) 5-(1,4-Dioxa-8-azaspiro[4,5]decan-8-yl]-2-oxo-1-propyl-1,4-benzodiazenine To a solution of 1-propyl-1,2,3,4-tetrahydro-3H-1,4-benzodiazepin-2,5-dione (13.5 g) (prepared in the same way as described in Example 4a and b except using N-propylanthranilic acid methyl ester as starting material) in dichloromethane (250 ml) was added phosphorus pentachloride (15.9 g) in dichloromethane (100 ml) over 30 min. The reaction mixture was stirred at room temperature for 2 h then concentrated under high vacuum. The residue obtained was redissolved in dichloromethane (200 ml), cooled to 0° C. and 1,4-dioxa-8-azaspiro[4.5]decane (24.2 ml) in dichloromethane (100 ml) was added dropwise. The reaction mixture was allowed to warm to room temperature and left to stir for 14 h, washed with saturated sodium carbonate solution (2×15 ml), dried ($MgSO_4$), filtered and concentrated in vacuo. The residue was dissolved in dichloromethane and filtered through a short plug of silica using 20% ethyl acetate in dichloromethane as eluant, then triturated with diethyl ether to give the required compound (18.2 g). mp 142° C. $^1$H NMR (360 MHz, $D_6$-DMSO) δ0.68 (3H, t, J=7.4 Hz), 1.24 (1H, m), 1.38 (1H, m), 1.51 (2H, m), 1.72 (2H, m), 3.25 (4H, m), 3.35 (1H, d, J=11.4 Hz), 3.55 (1H, m), 3.88 (4H, s), 3.94 (1H, d, J=11.4 Hz), 4.20 (1H, m), 7.31 (1H, m), 7.54 (3H, m). MS (CI) m/e 344 [MH]$^+$.

b) 5-(1,4-Dioxa-8-azaspiro[4,5]decan-8-yl)-3-oximido-2-oxo-1-propyl-1,4-benzodiazenine The product from step a) (18 g) was dissolved in dry toluene and cooled to −20° C. under an atmosphere of nitrogen. Potassium tert-butoxide (16.3 g) was added and after 20 min isoamyl nitrite (7.72 ml) was added dropwise. The reaction mixture was stirred at −20° C. for 14 h then allowed to warm to room temperature and quenched with dilute hydrochloric acid to pH 7. The organic layer was separated and the aqueous layer was extracted with ethyl acetate (2×200 ml). The organic layers were combined, dried ($MgSO_4$), filtered and concentrated under vacuum. The residue was triturated with diethyl ether to give the required compound (5.27 g). mp 197° C. $^1$H NMR (360 MHz, $D_6$-DMSO) δ0.71 (3H, 2×t, J=7.3 Hz), 1.24–1.54 (6H, m), 3.04–3.80 (5H, m), 3.91 (4H, s), 4.23 (1H, m), 7.18–7.62 (4H, m), 9.95 and 10.17 (1H, 2×s). MS (CI) m/e 373 [MH]$^+$.

c) N-[3(R,S)-2,3-Dihydro-5-(1,4-dioxa-8-azaspiro[4.5] decan-8-yl)-2-oxo-1-propyl-1H-1,4-benzodiazepin-3-yl]N'-[3-methylphenyl]urea The product from step b) (1.5 g) was dissolved in methanol (40 ml) and 5% rhodium on carbon catalyst (1.5 g) was added to the solution. The reaction mixture was heated at 60° C. under 50 psi of hydrogen on a Parr apparatus for 6 h then cooled, filtered and concentrated under vacuum. The residue was dissolved in dry dichloromethane (40 ml) and m-tolyl isocyanate (0.5 ml) was added in one portion. The reaction mixture was stirred at room temperature for 2 h then concentrated under vacuum. The residue was purified by chromatography on silica gel using 65% ethyl acetate in hexane as eluant to give the title compound (0.14 g). mp 238°–240° C. $^1$H NMR (360 MHz, D$_6$-DMSO) δ0.70 (3H, t, J=7.5 Hz), 1.26 (1H, m), 1.39 (1H, m), 1.54 (2H, m), 1.73 (2H, m), 2.21 (3H, s), 3.25 (4H, m), 3.64 (1H, m), 3.88 (4H, s), 4.23 (1H, m), 4.92 (1H, d, J=8.4 Hz), 6.70 (1H, d, J=6.8 Hz), 7.01–7.65 (8H, m), 8.82 (1H, s). MS (CI) m/e 492 [MH]$^+$. Anal. Found C, 65.92; H, 6.61; N, 14.27. $C_{27}H_{33}N_5O_4$ requires C, 65.97; H, 6.77; N, 14.25%.

EXAMPLE 2

N-[3(R,S)-2,3-Dihydro-2-oxo-5-(4-oxopiperidin-1-yl)-1-propyl-1H-1,4-benzodiazepin-3-yl]N'-[3-methylphenyl] urea To a solution of the product from Example 1c) (0.1 g) in 1,4-dioxan (30 ml) was added perchloric acid (3 ml). The reaction mixture was stirred at room temperature for 14 h then concentrated under high vacuum. The residue was partitioned between ethyl acetate (50 ml) and saturated sodium hydrogen carbonate solution (30 ml) then the organic layer was dried (Na$_2$SO$_4$), filtered and concentrated under vacuum. The crude product was purified by chromatography on silica gel using 65% ethyl acetate in hexane as eluant to give the title compound (0.06 g). mp 150°–152° C. $^1$H NMR (360 MHz, D$_6$-DMSO) δ0.70 (3H, t, J=7.3 Hz), 1.27 (1H, m), 1.41 (1H, m), 2.22 (3H, s), 2.26 (2H, m), 2.49 (2H, m), 3.52 (4H, m), 3.64 (1H, m), 4.23 (1H, m), 4.97 (1H, d, J=8.4 Hz), 6.71 (1H, d, J=7.2 Hz), 7.10 (3H, m), 7.17 (1H, s), 7.42 (1H, m), 7.68 (3H, m), 8.83 (1H, s). MS (CI) m/e 448 [MH]$^+$. Anal. Found C, 65.45; H, 6.49; N, 15.09. $C_{25}H_{29}N_5O_3$·0.6H$_2$O requires C, 65.51; H, 6.64; N, 15.28%.

EXAMPLE 3

N-[3(R,S)-2,3-Dihydro-2-oxo-1-propyl-5-(4-[1,1,1-trifluoroethylamine]piperidin-1-yl)-1H-1,4-benzodiazepin-3-yl] N'-[3-methylphenyl]urea The product from Example 2 (0.5 g) was dissolved in methanol (50 ml) with trifluoroethylamine hydrochloride (0.272 g). Crushed 3 Å sieves (10 g) were added to the mixture, followed by sodium cyanoborohydride (0.087 g). Methanolic hydrogen chloride was added dropwise until a pH of 5 was attained and stirring was continued at room temperature for 4 days. The reaction mixture was filtered and the solvent was removed under vacuum. The residue was dissolved in ethyl acetate and washed with saturated sodium hydrogen carbonate solution. The organic layer was dried (Na$_2$SO$_4$), filtered and concentrated in vacuo. The solid obtained was recrystallised from ethyl acetate/hexane to give the title compound (0.16 g). mp 209°–210° C. $^1$H NMR (360 MHz, D$_6$-DMSO) δ0.70 (3H, t, J=7.3 Hz), 1.14–1.45 (4H, m), 1.73–1.85 (2H, m), 2.21 (3H, s), 2.35 (1H, m, disappears on D$_2$O shake), 2.65–2.83 (3H, m), 3.22 (2H, m), 3.60–3.67 (3H, m), 4.23 (1H, m), 4.92 (1H, d, J=8.4 Hz), 6.70 (1H, d, J=6.8 Hz), 6.99–7.12 (4H, m), 7.38 (1H, m), 7.54 (1H, d, J=7.6 Hz), 7.64 (2H, m), 8.81 (1H, s). MS (CI) m/e 531 [MH]$^+$. Anal. Found C, 61.48; H, 6.18; N, 15.82. $C_{27}H_{33}F_3N_3O_2$ requires C, 61.12; H, 6.27; N, 15.84%.

EXAMPLE 4

N-[3(R,S)-2,3-Dihydro-5-(4,4-dimethylpiperidin-1-yl)-1-methyl-2-oxo-1H-1,4-benzodiazepin-3-yl]N'-[indan-5-yl] urea Intermediate 1: 4,4-Dimethylpiperidine To a solution of lithium aluminium hydride in diethyl ether (430 ml of a 1.0M solution) under nitrogen, at reflux, was added a suspension of 3,3-dimethylglutarimide (20 g) in anhydrous diethyl ether (570 ml), dropwise over a period of 1 h. The mixture was then heated at reflux for a further 8 h then cooled to 0° C. Water (16 ml) was added dropwise, followed by aqueous sodium hydroxide (16 ml of a 4N solution) and water (48 ml). The resultant solid was removed by filtration, the filtrate dried (Na$_2$SO$_4$) and evaporated. The pale yellow oil was distilled under reduced pressure to afford the title piperidine (12.3 g). bp 44° C./25 mmHg. $^1$H NMR (360 MHz, CDCl$_3$) δ0.93 (6H, s), 1.29–1.32 (4H, m), 2.78–2.81 (4H, m).

a) Methyl 2-(N-bromoacetyl-N-methylamino)benzoate

A solution of bromoacetyl bromide (209 g) in dichloromethane (200 ml) was added dropwise to a cooled (ice bath) solution of methyl N-methylanthranilate (168 g) in dichloromethane (1.41). A solution of sodium hydroxide (59 g) in water (400 ml) was added dropwise and the reaction mixture was stirred at room temperature for 20 h. The organic phase was separated and washed with 1M hydrochloric acid (500 ml), brine (300 ml), saturated sodium hydrogen carbonate solution (400 ml), dried (Na$_2$SO$_4$) then evaporated to afford the required product (255 g). $^1$H NMR (360 MHz, CDCl$_3$) δ3.23 (3H, s), 3.54 (1H, d, J=11 Hz), 3.60 (1H, d, J=11 Hz), 3.90 (3H, s), 7.40 (1H, d, J=8 Hz), 7.51 (1H, dd, J$_1$=J$_2$=8 Hz), 7.65 (1H, dd, J$_1$=J$_2$=8 Hz), 8.04 (1H, d, J=8 Hz).

b) 1-Methyl-1,2,3,4-tetrahydro-3H-1,4-benzodiazepin-2,5-dione

Ammonia gas was bubbled through an ice-cooled solution of methyl 2-N-bromoacetyl-N-methylamino)benzoate (255 g) in methanol (1600 ml) until saturated. The cooling bath was removed and the reaction mixture left standing at room temperature for 18 h. The precipitate was collected to afford the required product (79 g). mp 190°–193° C. $^1$H NMR (360 MHz, CDCl$_3$) δ3.42 (3H, s), 3.80 (2H, brs), 6.80 (1H, s), 7.24 (1H, d, J=8 Hz), 7.32 (1H, dd, J$_1$=J$_2$=8 Hz), 7.57 (1H, dd, J$_1$=J$_2$=8 Hz), 7.90 (1H, d, J=8 Hz). Found: C, 63.20; H, 5.25; N, 14.77. $C_{10}H_{10}N_2O_2$ requires C, 63.15; H, 5.30; N, 14.73%.

c) 1.2-Dihydro-5-(4,4-dimethylpiperidin-1-yl)-1-methyl-3H-1,4-benzodiazepin-2-one To a solution of the product of part b) (10 g) in anhydrous dichloromethane (700 ml) was added phosphorus pentachloride (13.17 g) in anhydrous dichloromethane (500 ml) over a period of 30 min. The reaction mixture was stirred at ambient temperature for 2.5 h. The solvent was evaporated in vacuo and the residue redissolved in anhydrous dichloromethane (400 ml). After cooling to 0° C., a solution of 4,4-dimethylpiperidine (Intermediate 1) (5.95 g) and triethylamine (18.3 ml) in anhydrous dichloromethane (100 ml) was added dropwise. The reaction mixture was allowed to warm to ambient temperature with stirring for 19 h, washed with saturated potassium carbonate solution (500 ml), water (200 ml) and brine (150 ml). The organic layer was dried ($K_2CO_3$) and treated with decolourising charcoal and silica gel. After filtering, the solvent was evaporated in vacuo. The residue was redissolved in dichloromethane (300 ml) and extracted with citric acid solution (10%, 3×50 ml). The combined aqueous layers were basified (4M NaOH solution) and extracted with dichloromethane (6×125 ml). These organic extracts were combined, dried ($K_2CO_3$) and evaporated in vacuo to give the title compound (7.5 g). mp 143°–145° C. $^1$H NMR (360 MHz, $CDCl_3$) δ0.98 (6H, s), 1.26–1.36 (2H, m), 1.46–1.53 (2H, m), 3.13–3.32 (4H, m), 3.36 (3H, s), 3.50 (1H, d, J=12.0 Hz), 4.24 (1H, d, J=12.0 Hz), 7.21 (1H, t, J=8.3 Hz), 7.27 (1H, d, J=8.3 Hz), 7.46–7.53 (2H, m). MS (CI) m/e 286 [MH]$^+$.

d) 1,2-Dihydro-5-(4,4-dimethylpiperidin-1-yl)-1-methyl-3-oximido-3H-1,4-benzodiazepin-2-one A solution of the product of part c) (7 g) in anhydrous toluene (200 ml) was cooled to −20° C. under an atmosphere of nitrogen, and potassium tert-butoxide (7.5 g) was added portionwise over 5 min. After stirring at −20° C. for 30 min, isopentyl nitrite (3.9 ml) was added dropwise. The reaction mixture was stirred at −20° C. for 5 h 30 min and then allowed to warm to ambient temperature. The mixture was poured onto a rapidly stirred mixture of ethyl acetate (300 ml) and water (50 ml) containing citric acid (4.68 g), stirred vigorously for 5 min and then neutralised to pH 7 using saturated potassium carbonate solution. The organic layer was separated and the aqueous layer extracted with ethyl acetate (2×100 ml). The combined organic phases were dried ($Na_2SO_4$) and evaporated in vacuo to give an orange solid. This was triturated with diethyl ether to give the title compound (6.92 g). mp 215° C. (dec.). $^1$H NMR (360 MHz, $D_6$-DMSO) δ0.97 (6H, s), 1.23–1.36 (2H, m), 1,40–1.50 (2H, m), 3.22–3.50 (7H, m), 7.26–7.32 (1H, m), 7.44 (1H, d, J=7.9 Hz), 7.48–7.60 (2H, m), 10.10 (1H, brs). MS (CI) m/e 315 [MH]$^+$.

e) 1,2-Dihydro-5-(4,4-dimethylpiperidin-1-yl)-1-methyl-3-(O-ethylaminocarbonyl)oximido-3H-1,4-benzodiazepin-2-one To a suspension of the product of part d) (3.64 g) in anhydrous tetrahydrofuran (60 ml) was added triethylamine (1.6 ml) followed by ethyl isocyanate (1.4 ml) dropwise. This mixture was heated at 60° C. under an atmosphere of nitrogen for 3 h. The solvent was evaporated in vacuo and the residue chromatographed on silica gel using a gradient of 0% to 3% methanol in dichloromethane as eluant to give the title compound (4.5 g). $^1$H NMR (360 MHz, $CDCl_3$) δ1.02 (6H, brs), 1.13 (3H, t, J=7.3 Hz), 1.20–1.84 (4H, m), 3.20–3.30 (3H, m), 3.35–3.42 (4H, m), 3.60–3.78 (1H, m), 3.80–4.00 (1H, m), 6.36–6.42 (1H, m), 7.20–7.35 (3H, m), 7.46–7.52 (1H, m). MS (CI) m/e 386 [MH]$^+$.

f) N-[3(R,S)-2,3-Dihydro-5-(4,4-dimethylpiperidin-1-yl)-1-methyl-2-oxo-1H-1,4-benzodiazepin-3-yl]N'-[indan-5-yl]urea To a solution of the product of part e) (4.5 g) in methanol (250 ml) was added 10% palladium on carbon (1 g). The mixture was hydrogenated at 40 psi for 3 h and then the catalyst was filtered off and washed with methanol. The solvent was evaporated in vacuo to give the amine (3.5 g) which was used without further purification.

To a solution of 5-aminoindane (2.32 g) in anhydrous tetrahydrofuran (150 ml) cooled to 0° C. under an atmosphere of nitrogen was added triphosgene (1.72 g) in one portion. Triethylamine (7.2 ml) was added dropwise. After stirring at 0° C. for 30 min a solution of the amine (3.5 g) in anhydrous tetrahydrofuran (20 ml) was added dropwise. The mixture was stirred at 0° C. for 5 min and then was allowed to warm to ambient temperature and stirred for 10 min. The solvent was evaporated in vacuo and the residue partitioned between ethyl acetate (150 ml) and water (75 ml). The undissolved solid was collected by filtration to afford the title product (3.17 g). mp 132° C. (dec.). $^1$H NMR (360 MHz, $CDCl_3$) δ0.96 (6H, s), 1.30–1.39 (2H, m), 1.44–1.56 (2H, m), 2.04 (2H, quin, J=7.4 Hz), 2.84 (4H, q, J=7.0 Hz), 3.16–3.26 (2H, m), 3.28–3.38 (2H, m), 3.42 (3H, s), 5.32 (1H, d, J=8.0 Hz), 6.59–6.66 (1H, m), 6.95–7.13 (3H, m), 7.24–7.36 (3H, m), 7.51–7.58 (2H, m). MS (CI) m/e 460 [MH]$^+$. Anal. Found C, 67.85; H, 7.11; N, 14.60. $C_{27}H_{33}N_5O_2H_2O$ requires C, 67.90; H, 7.39; N, 14.66%.

An alternative procedure can be used for preparation of N-[3(R,S)-2,3-dihydro-5-(4,4-dimethylpiperidin-1-yl)-1-methyl-2-oxo-1H-1,4-benzodiazepin-3-yl]N'-indan-5-yl] urea:

Step 1: Indan-5-yl isocyanate

To a solution of 5-aminoindane (25 g) in anhydrous diethyl ether (1250 ml), under an atmosphere of nitrogen, at 0° C. was added triphosgene (18.3 g). The mixture was stirred at 0° C. for 2 min then triethylamine (64.7 ml) was added until pH8. The mixture was stirred at 0° C. for 10 min then at. 10° C. for 10 min. The undissolved solids were filtered off and the filtrate evaporated in vacuo. The residue was distilled at 100° C./1 mbar to afford the title compound (20 g). $^1$H NMR (360 MHz, $CDCl_3$) δ2.07 (2H, quin, J=7.5 Hz), 2.86 (4H, m), 6.84 (1H, dd, J=7.9 and 2.0 Hz), 6.94 (1H, s), 7.13 (1H, d, J=7.9 Hz).

Step 2: N-[3(R,S)-2,3-Dihydro-5-(4,4-dimethylpiperidin-1-yl)-1-methyl-2-oxo-1H-1,4-benzodiazepin-3-yl]N'-[indan-5-yl]urea To a solution of 1,2-dihydro-5-(4,4-dimethylpiperidin-1-yl)-1-methyl-3-(O-ethylaminocarbonyl)oximido-3H-1,4-benzodiazepin-2-one (10.3 g) in methanol (400 ml) was added 10% palladium on carbon (2.24 g, 21% (w/w)). The mixture was hydrogenated at 40 psi for 4 h then the catalyst was filtered off and washed with methanol. The solvent was evaporated in vacuo to give the crude amine (8.3 g).

To a stirred solution of the crude amine (8.3 g) in anhydrous diethyl ether (50 ml) under an atmosphere of nitrogen, at room temperature, was added a solution of indan-5-yl isocyanate (4.2 g) in anhydrous diethyl ether (7 ml). After stirring at room temperature for 10 min the title compound (8.9 g) was collected by filtration.

EXAMPLE 5

Chiral Separation of N-[3(R,S)-2,3-dihydro-5-(4,4-dimethylpiperidin-1-yl)-1-methyl-2-oxo-1H-1,4-benzodiazepin-3-yl]N'-[indan-5-yl]urea N-[3(R,S)-2,3-Dihydro-5-(4,4-dimethylpiperidin-1-yl)-1-methyl-2-oxo-1H-1,4-benzodiazepin-3-yl]N'-[indan-5-yl] urea (0.17 g) was dissolved in 1:1 chloroform:methanol (4 ml). 440 µl of this solution was injected onto a dinitrobenzoyl leucine column (250×20 mm i.d., 5 µm) per run using 95:5:1 1-chlorobutane:methanol:acetic acid as the mobile phase. Using a flow rate of 20 ml/min and UV detection at 330 nm, the two enantiomers were efficiently separated. The fractions containing each separate enantiomer were combined and evaporated in vacuo. Separately each enantiomer was partitioned between ethyl acetate (25 ml) and potassium carbonate solution (0.5M, 10 ml). The organic phases were dried ($Na_2SO_4$) and evaporated in vacuo. The residues obtained were redissolved in dichloromethane and saturated ethereal hydrogen chloride (~2 ml) was added. The solvents were evaporated in vacuo and the residues obtained were triturated with diethyl ether and the resulting solids collected by filtration to give:

Peak A (69 mg). mp 180° C. (dec.). $^1$H NMR (360 MHz, D$_6$-DMSO) δ 0.92–1.06 (6H, m), 1.22–1.62 (4H, m), 1.97 (2H, quin, J=7.3 Hz), 2.77 (4H, q, J=7.3 Hz), 3.23–3.70 (7H, m), 5.30–5.38 (1H, m), 7.05–7.13 (2H, m), 7.29 (2H, brs), 7.56 (1H, t, J=7.5 Hz), 7.71 (1H, d, J=8.2 Hz), 7.83–7.92 (2H, m), 9.93 (1H, brs), 10.56 (1H, brs). MS (CI) m/e 460 [MH]$^+$. Anal. Found C, 61.67; H, 6.81; N, 13.67. C$_{27}$H$_{33}$N$_5$O$_2$.HCl.1.5(H$_2$O) requires C, 62.00; H, 7.13; N, 13.39%. [α]$^{22}_D$ -241.1° (c=0.54, MeOH). Purity A:B=>99.5:0.5.

Peak B (67mg). mp 180° C. (dec.). $^1$H NMR (360 MHz, D$_6$-DMSO) δ 0.92–1.06 (6H, m), 1.22–1.62 (4H, m), 1.97 (2H, quin, J=7.3 Hz), 2.77 (4H, q, J=7.3 Hz), 3.23–3.70 (7H, m), 5.30–5.38 (1H, m), 7.05–7.13 (2H, m), 7.28 (2H, brs), 7.56 (1H, t, J=7.5 Hz), 7.71 (1H, d, J=8.2 Hz), 7.83–7.92 (2H, m), 9.33 (1H, brs), 10.46 (1H, brs). MS (CI) m/e 460 [MH]$^+$. Anal. Found C, 61.49; H, 7.06; N, 13.39. C$_{27}$H$_{33}$N$_5$O$_2$.HCl. 1.75(H$_2$O) requires C, 61.47; H, 7.16; N, 13.27%. [α]$^{26}_D$ +226.8° (c=0.63, MeOH). Purity A:B=1.7:98.3.

EXAMPLE 6

N-[3(R,S)-2,3-Dihydro-5-(cis-2,6-dimethylpiperidin-1-yl)-1-methyl-2-oxo-1H-1,4-benzodiazepin-3-yl]N'-[3-methylphenyl]urea a) 1,2-Dihydro-5-(cis-2,6-dimethylpiperidin-1-yl)-1-methyl-3-oximido-3H-1,4-benzodiazepin-2-one Prepared as in Example 4, steps c) and d), from 1-methyl-1,2,3,4-tetrahydro-3H-1,4-benzodiazepin-2,5-dione (5 g) and cis-2,6-dimethylpiperidine (3.5 ml). mp 240° C. (dec.). $^1$H NMR (360 MHz, D$_6$-DMSO) δ 0.85–0.96 (3H, m), 1.20–1.92 (9H, m), 3.31 (3H, s), 3.97–4.09 (1H, m), 4.36–4.56 (1H, m), 7.25–7.34 (1H, m), 7.40 (1H, d, J=7.7 Hz), 7.49–7.60 (2H, m), 9.88–10.16 (1H, m). MS (CI) m/e 315[MH]$^+$.

b) N-[3(R,S)-2,3-Dihydro-5-(cis-2,6-dimethylpiperidin-1-yl)-1-methyl-2-oxo-1H-1,4-benzodiazepin-3-yl]N'-[3-methylphenyl]urea To a suspension of the product of part a) (1.5 g) in methanol (150 ml) was added 5% rhodium on carbon (1.5 g, 100% (w/w)). The mixture was hydrogenated at 40 psi at 60° C. for 6 h 30 min and, after cooling, the catalyst was filtered off and washed with methanol. The solvent was evaporated in vacuo to give the amine (1.43 g).

The amine was redissolved in anhydrous tetrahydrofuran (20 ml) and cooled to 0° C. under an atmosphere of nitrogen. m-Tolyl isocyanate (0.62 ml) was added dropwise. After stirring for 10 min the mixture was left standing in the fridge overnight. The reaction mixture was evaporated in vacuo and the residue partitioned between ethyl acetate (50 ml) and water (30 ml). The aqueous layer was separated and extracted with ethyl acetate (25 ml). The combined organic phases were dried (Na$_2$SO$_4$) and evaporated in vacuo. The residue was chromatographed on silica gel using a gradient of 0% to 50% ethyl acetate in dichloromethane as the eluant to afford a gum. This was further purified by chromatographing on silica gel using 20% ethyl acetate in dichloromethane as the eluant to afford a solid. This was triturated with diethyl ether to give the title compound (0.32 g). mp 248° C. (dec.). $^1$H NMR (360 MHz, CDCl$_3$) δ 0.88–1.03 (3H, m), 1.33 (3H, d, J=6.9 Hz), 1.42–1.90 (6H, m), 2.28 (3H, s), 3.42 (3H, s), 3.90–4.32 (2H, m), 5.27 (1H, d, J=8.0 Hz), 6.42–6.50 (1H, m), 6.81 (1H, d, J=7.0 Hz), 6.91 (1H, brs), 7.06–7.16 (2H, m), 7.21–7.28 (2H, m), 7.32 (1H, d, J=7.8 Hz), 7.42–7.52 (2H, m). MS (CI) m/e 434[MH]$^+$. Anal. Found C, 68.07; H, 7.12; N, 15.98. C$_{23}$H$_{31}$N$_5$O$_2$.0.35(H$_2$O) requires C, 68.27; H, 7.26; N, 15.92%.

EXAMPLE 7

N-[3(R,S)-2,3-Dihydro-1-methyl-5-(4-methylpiperidin-1-yl)-2-oxo-1H-1,4-benzodiazepin-3-yl]N'-[3-methylphenyl]urea a) 1,2-Dihydro-1-methyl-5-(4-methylpiperidin-1-yl)-3-oximido-3H-1,4-benzodiazepin-2-one Prepared as in Example 4, steps c) and d) from 1-methyl-1,2,3,4-tetrahydro-3H-1,4-benzodiazepin-2,5-dione (5 g) and 4-methylpiperidine (10.9 ml). mp 225°–228° C. $^1$H NMR (360 MHz, D$_6$-DMSO) δ 0.90–1.15 (4H, m), 1.20–1.36 (1H, m), 1.54–1.76 (3H, m), 2.77–3.01 (2H, m), 3.26 (3H, s), 3.69–4.24 (2H, m), 7.24–7.32 (1H, m), 7.38–7.43 (1H, m), 7.46–7.58 (2H, m), 9.93 and 10.16 (1H, 2×s). MS (CI) m/e 301 [MH]$^+$.

b) N-[3(R,S)-2,3-Dihydro-1-methyl-5-(4-methylpiperidin-1-yl)-2-oxo-1H-1,4-benzodiazepin-3-yl]N'-[3-methylphenyl]urea In the same way as in Example 6b) from 1,2-dihydro-1-methyl-5-(4-methylpiperidin-1-yl)-3-oximido-3H-1,4-benzodiazepin-2-one (0.6 g), the amine (0.57 g) was obtained. The title compound was then prepared from the crude amine and m-tolyl isocyanate (0.26 ml) as described in Example 6b) and recrystallised from methanol. mp 142° C. (dec.). $^1$H NMR (360 MHz, CDCl$_3$) δ 0.95 (3H, d, J=6.3 Hz), 1.06–1.19 (1H, m), 1.24–1.36 (1H, m), 1.46–1.60 (2H, m), 1.65–1.76 (1H, m), 2.28 (3H, s), 2.62–2.82 (2H, m), 3.41 (3H, s), 3.48–3.58 (1H, m), 3.90–3.98 (1H, m), 5.28 (1H, d, J=8.6 Hz), 6.54 (1H, d, J=7.9 Hz), 6.82 (1H, d, J=7.3 Hz), 6.95 (1H, s), 7.04–7.16 (2H, m), 7.21–7.32 (3H, m), 7.45–7.56 (2H, m). MS (CI) m/e 420 [MH]$^+$. Anal. Found C, 65.09; H, 6.79; N, 15.94. C$_{24}$H$_{29}$N$_5$O$_2$.1.25(H$_2$O) requires C, 65.21; H, 7.18; N, 15.84%.

EXAMPLE 8

Chiral separation of N-[3(R,S)-2,3-dihydro-1-methyl-5-(4-methylpiperidin-1-yl)-2-oxo-1H-1,4-benzodiazepin-3-yl] N'-[3-methylphenyl]urea N-[3(R,S)-2,3-Dihydro-1-methyl-5-(4-methylpiperidin-1-yl)-2-oxo-1H-1,4-benzodiazepin-3-yl]N'-[3-methylphenyl]urea (0.6 g) was dissolved in 1:24 methanol:dichloromethane (6 ml). The enantiomers were separated as described in Example 5. Peak A (250 mg). mp 178° C. (dec.). $^1$H NMR (360 MHz, CDCl$_3$) δ 0.96–1.08 (3H, m), 1.30–1.44 and 1.64–1.86 (4H, 2×m), 1.95–2.06 (1H, m), 2.28 (3H, s), 3.14–3.60 (5H, m), 3.62–3.76 (1H, m), 4.32–4.42 and 4.64–4.70 (1H, 2×m), 5.67–5.76 (1H, m), 6.80 (1H, d, J=7.4 Hz), 7.11 (1H, t, J=7.8 Hz), 7.16–7.34 (3H, m), 7.38–7.64 (3H, m), 7.72–7.82 (1H, m), 8.07 and 8.50 (1H, 2×brs), 11.85 and 11.96 (1H, 2×brs). MS (CI) m/e 420 [MH]$^+$. [α]$^{23}_D$ -247.7° (c=0.50, MeOH). Purity A:B= >99.5:0.5.

Peak B (270 mg). mp 180° C. (dec.). $^1$H NMR (360 MHz, CDCl$_3$) δ 0.96–1.08 (3H, m), 1.30–1.44 and 1.64–1.86 (4H, 2×m), 1.95–2.06 (1H, m), 2.28 (3H, s), 3.14–3.60 (5H, m), 3.62–3.76 (1H, m), 4.32–4.42 and 4.64–4.70 (1H, 2×m), 5.67–5.76 (1H, m), 6.80 (1H, d, J=7.4 Hz), 7.11 (1H, t, J=7.8 Hz), 7.16–7.34 (3H, m), 7.38–7.64 (3H, m), 7.72–7.82 (1H, m), 8.07 and 8.50 (1H, 2×brs), 11.85 and 11.96 (1H, 2×brs). MS (CI) m/e 420 [MH]$^+$. [α]$^{23}_D$ +244.3° (c=0.50, MeOH). Purity A:B=2.3:97.7.

EXAMPLE 9

N-[3(R,S)-2,3-Dihydro-5-(4,4-dimethylpiperidin-1-yl)-1-methyl-2-oxo-1H-1,4-benzodiazepin-3-yl]N'-[3-methylphenyl]urea The amine was prepared as in Example 6b), from 1,2-dihydro-5-(4,4-dimethylpiperidin-1-yl)-1-methyl-3-oximido-3H-1,4-benzodiazepin-2-one (7.5 g). The title compound was prepared from the crude amine and m-tolyl isocyanate (3.1 ml) as described in Example 6b). mp 135° C. (dec.). 1H NMR (360 MHz, CDCl$_3$) $\delta$0.95 (6H, s), 1.28–1.38 (2H, m), 1.44–1.51 (2H, m), 2.26 (3H, s), 3.15–3.24 (2H, m), 3.26–3.39 (2H, m), 3.43 (3H, s), 5.33 (1H, d, J=8.0 Hz), 6.65–6.72 (1H, m), 6.82 (1H, d, J=7.0 Hz), 7.06–7.19 (3H, m), 7.22–7.35 (3H, m), 7.50–7.57 (2H, m). MS (CI) m/e 434 [MH]$^+$. Anal. Found C, 66.76; H, 7.03; N, 15.60. C$_{25}$H$_{31}$N$_5$O$_2$.0.9(H$_2$O) requires C, 66.76; H, 7.03; N, 15.57%.

EXAMPLE 10

Chiral Separation of N-[3(R,S)-2,3-dihydro-5-(4,4-dimethylpiperidin-1-yl)-2-oxo-1H-1,4-benzodiaze pin-3-yl]N'-[3-methylphenyl]urea N-[3(R,S)-2,3-Dihydro-5-(4,4-dimethylpiperidin-1-yl)-1-methyl-2-oxo-1H-1,4-benzodiazepin-3yl]N'-[3-methylphenyl]urea (0.27 g) was dissolved in 2:3 methanol:dichloromethane (5 ml). The enantiomers were separated as described in Example 5.

Peak A (103 mg). mp 170° C. (dec.). $^1$H NMR (360 MHz, D$_6$-DMSO) $\delta$0.92–1.07 (6H, m), 1.27–1.40 (1H, m), 1.49–1.65 (3H, m), 2.23 (3H, s), 3.30–3.77 (7H, m), 5.30–5.38 (1H, m), 6.76 (1H, d, J=7.3 Hz), 7.08–7.19 (2H, m), 7.23 (1H, s), 7.32–7.39 (1H, m), 7.56 (1H, t, J=7.6 Hz), 7.71 (1H, d, J=8.1 Hz), 7.82–7.92 (2H, m), 9.50 (1H, brs), 10.57 (1H, brs). MS (CI) m/e 434 [MH]$^+$. Anal. Found C, 62.00; H, 7.09; N, 14.11. C$_{25}$H$_{31}$N$_5$O$_2$.HCl.0.8(H$_2$O) requires C, 61.99; H, 6,99; N, 14.46%. [$\alpha$]$^{22}_D$−264.9° (c=0.61, MeOH). Purity A:B=>99.5:0.5.

Peak B (89 mg). mp 172° C. (dec.). $^1$H NMR (360 MHz, D$_6$-DMSO) $\delta$0.92–1.05 (6H, m), 1.25–1.40 (1H, m), 1.45–1.65 (3H, m), 2.23 (3H, s), 3.16–3.76 (7H, m), 5.26–5.37 (1H, m), 6.76 (1H, d, J=7.2 Hz), 7.06–7.36 (4H, m), 7.50–7.60 (1H, m), 7.67–7.74 (1H, m), 7.78–7.94 (2H, m), 9.40 (1H, brs), 10.46 (1H, brs). MS (CI) m/e 434 [MH]$^+$. Anal. Found C, 61.83; H, 7.07; N, 14.03. C$_{25}$H$_{31}$N$_5$O$_2$.HCl.H$_2$O requires C, 61.53; H, 7.02; N, 14.35%. [$\alpha$]$^{22}_D$+216.6° (c=0.65, MeOH). Purity A:B=3.0:97.0.

EXAMPLE 11

N-[3(R,S)-2,3-Dihydro-5-(4-methoxypiperidin-1-yl)-1-methyl-2-oxo-1H-1,4-benzodiazepin-3-yl]N'-[3-methylphenyl]urea a) 1,2-Dihydro-5-(4-methoxypiperidin-1-yl)-3H-1-methyl-1,4-benzodiazepin-2-one Prepared as described in Example 4c), from 1-methyl-1,2,3,4-tetrahydro-3H-1,4-benzodiazepin-2,5-dione (4.5 g) and 4-methoxypiperidine hydrochloride (3.6 g). $^1$H NMR (360 MHz, CDCl$_3$) $\delta$1.43–1.86 (3H, m), 1.98–2.08 (1H, m), 2.91–3.18 (2H, m), 3.33–3.60 (9H, m), 3.63–3.75 (1H, m), 4.25–4.31 (1H, m), 7.20–7.32 (2H, m), 7.47–7.53 (2H, m). MS (CI) m/e 288 [MH]$^+$.

b) 1,2-Dihydro-5-(4-methoxypiperidin-1-yl)-1-methyl-3-oximido-3H-1,4-benzodiazepin-2-one Prepared as Example 4d), from 1,2-dihydro-5-(4-methoxypiperidin-1-yl)-methyl-3H-1,4-benzodiazepin-2-one (2.3 g) map 176° C. (dec.). $^1$H NMR (360 MHz, D$_6$-DMSO) $\delta$1.29–1.50 (1H, m), 1.53–1.65 (1H, m) 1.76–1.88 (1H, m), 1.90–2.04 (1H, m), 3.05–3.95 (11H, m), 7.25–7.32 (1H, m), 7.41–7.63 (3H, m), 9.97 and 10.21 (1H, 2×brs). MS (CI) m/e 317 [MH]$^+$.

c) N-[3(R,S)-2,3-Dihydro-5-(4methoxypiperidin-1-yl)-1-methyl-2-oxo-1H-1,4-benzodiazepin-3-yl]N'-[3-methylphenyl]urea By the method of Example 6b), from 1,2-dihydro-5-(4-methoxypiperidin-1-yl)-1-methyl-3-oximido-3H-1,4-benzodiazepin-2-one (1.4 g) was obtain the amine. The title compound was prepared from the crude amine and m-tolyl isocyanate (0.57 ml) as described in Example 6b). mp 145°–148° C. $^1$H NMR (360 MHz, CDCl$_3$), $\delta$1.45–1.58 (1H, m), 1.60–1.72 (1H, m), 1.74–1.80 (1H, m), 1.92–2.05 (1H, m), 2.28 (3H, s), 2.97–3.10 (2H, m), 3.30–3.55 (8H, m), 3.64–3.78 (1H, m), 5.33 (1H, d, J=8.0 Hz), 6.65–6.75 (1H, m), 6.82 (1H, d, J=6.7 Hz), 7.03–7.36 (6H, m), 7.49–7.58 (2H, m). MS (CI) m/e 436 [MH]$^+$. Anal. Found C, 62.94; H, 6.63; N, 15.40. C$_{24}$H$_{29}$N$_5$O$_3$. 1.25(H$_2$O) requires C, 62.93; N, 6.93; N, 15.29%.

EXAMPLE 12

(−)-N-[2,3,Dihydro-1-methyl-5-(4-methylpiperidin-1-yl)-2-oxo-1H-1,4-benzodiazepin-3-yl]N'-[indan-5-yl]urea hydrochloride The amine was prepared by the method of Example 6b), using 1,2-dihydro-1-methyl-5-(4-methylpiperidin-1-yl)-3-oximido-3H-1,4-benzodiazepin-2-one (5.7 g). To a solution of 5-aminoindane (2.53 g) in anhydrous tetrahydrofuran (120 ml), cooled to 0° C. under an atmosphere of nitrogen, was added triphosgene (1.88 g) in one portion. Triethylamine (5.3 ml) was added dropwise. After stirring at 0° C. for 20 min, a solution of the amine (5.4 g) in anhydrous tetrahydrofuran (20 ml) was added dropwise. The mixture was stirred at 0° C. for 10 min and then left to stand in the fridge overnight. The reaction mixture was evaporated in vacuo and the residue partitioned between ethyl acetate (100 ml) and water (50 ml). The aqueous layer was separated and extracted with ethyl acetate (50 ml). The combined organic phases were dried (NA$^2$SO$_4$) and evaporated in vacuo. The residue was triturated with dichloromethane to give N-[3(R,S)-2,3-dihydro-1-methyl-5-(4-methylpiperidin-1-yl)-2-oxo-1H-1,4-benzodiazepin-3-yl]N'-[indan-5-yl]urea (2.44 g).

The title compound was separated following the procedure of Example 5. mp 185° C. (dec.). $^1$H NMR (360 MHz, D$_6$-DMSO) $\delta$0.87–1.04 (3H, m), 1.20–1.88 (5H, m), 1.97 (2H, quin, J=7.4 Hz), 2.77 (4H, q, J=7.3 Hz), 3.08–3.62 (6H, m), 3.87–4.20 (1H, m), 5.26–5.38 (1H, m), 7.02–7.11 (2H, m), 7.20–7.33 (2H, m), 7.50–7.58 (1H, m), 7.65–7.72 (1H, m), 7.75–7.93 (2H, m), 9.40 (1H, brs), 10.52 (1H, brs). MS (CI) m/e 446 [MH]$^+$. Anal. Found C, 62.51; H, 6.93; N, 13.91. C$_{26}$H$_{31}$N$_5$O$_2$.HCl.H$_2$O requires C, 62.45; H, 6.85; N, 14.01%. [$\alpha$]$^{22}_D$-245.4° (c=0.62, MeOH). Purity A:B=99.0:1.0.

EXAMPLE 13

N-[3(R,S)-2,3-Dihydro-5-(cis-2,6-dimethylpiperidin-1-yl)-1-methyl-2-oxo-1H-1,4-benzodiazepin-3-yl]N'-[indan-5-yl]urea a) 1,2-Dihydro-5-(cis-2,6-dimethylpiperidin-1-yl)-1-methyl-3-(O-ethylaminocarbonyl)oximido-3H-1,4-benzodiazepin-2-one Prepared as described in Example 4e), from 1,2-dihydro-5-(cis-2,6-dimethylpiperidin-1-yl)-1-methyl-3-oximido-3H-1,4-benzodiazepin-2-one (1.15 g) and ethyl isocyanate (0.43 ml). $^1$H NMR (360 MHz, CDCl$_3$) $\delta$1.01 (3H, d, J=7.1 Hz), 1.12 (3H, t, J=7.2 Hz), 1.36 (3H, d, J=7.0 Hz), 1.37–1.94 (6H, m), 3.20–3.31 (2H, m), 3.44 and 3.46 (3H, 2×s), 4.14–4.23 (1H, m), 4.58–4.67 and 4.72–4.80 (1H, 2×m), 6.12–6.19 and 6.38–6.46 (1H, 2×m), 7.20–7.38 (3H, m), 7.43–7.50 (1H, m). MS (CI) m/e 386 (MH)⁺.

b) N-[3(R,S)-2,3-Dihydro-5-(cis-2,6-dimethylpiperidin-1-yl)-1-methyl-2-oxo-1H-1,4-benzodiazepin-3-yl]N'-[indan-5-yl]urea The amine was prepared as in Example 4 f), from 1,2-dihydro-5-(cis-2,6-dimethylpiperidin-1-yl)-1-methyl-3-(O-ethylaminocarbonyl)oximido-3H-1,4-benzodiazepin-2-one (1.41 g).

The title compound was then prepared from the crude amine (1.1 g) and 5-aminoindane (0.73 g) as described in Example 4f). mp 240° C. (dec.). $^1$H NMR (360 MHz, CDCl$_3$) δ0.84–0.94 (3H, m), 1.25 (3H, d, J=6.8 Hz), 1.40–1.84 (6H, m), 1.96 (2H, quin, J=7.4 Hz), 2.75 (4H, q, J=7.0 Hz), 3.33 (3H, s), 3.80–4.14 (2H, m), 4.93 (1H, d, J=8.6 Hz), 6.88 (1H, d, J=8.5 Hz), 7.03 (2H, s), 7.29 (1H, s), 7.33–7.39 (1H, m), 7.48 (1H, d, J=8.0 Hz), 7.54–7.64 (2H, m), 8.74 (1H, s). MS (CI) m/e 460 [MH]⁺. Anal. Found C, 69.83; H, 7.15; N, 14.82. C$_{27}$H$_{33}$N$_5$O$_2$.0.25(H$_2$O) requires C, 69.88; H, 7.28; N, 15.09%.

EXAMPLE 14

Chiral Separation of N-[3(R,S)-2,3-dihydro-5-(4-methoxypiperidin-1-yl)-1-methyl-2-oxo-1H-1,4-benzodiazepin-3-yl]N'-[3-methylphenyl]urea.

N-[3(R,S)-2,3-Dihydro-5-(4-methoxypiperidin-1-yl)-1-methyl-2-oxo-1H-1,4-benzodiazepin-3-yl]N'-[3-methylphenyl]urea (Example 11) (0.32 g) was dissolved in 4:1 chloroform:methanol (4 ml). The enantiomers were separated as described in Example 5.

Peak A (135 mg). mp 165° C. (dec.). 1H NMR (360 MHz, D$_6$-DMSO) δ1.42–1.60 (1H, m), 1.63–1.87 (2H, m), 1.94–2.08 (1H, m), 2.23 (3H, s), 3.14–3.86 (11H, m), 5.26–5.38 (1H, m), 6.76 (1H, d, J=7.0 Hz), 7.08–7.17 (2H, m), 7.22 (1H, brs), 7.28–7.38 (1H, m), 7.50–7.59 (1H, m), 7.70 (1H, d, J=8.5 Hz), 7.78–7.83 (1H, m), 9.39 (1H, brs), 10.54 (1H, brs). MS (CI) m/e 436 [MH]⁺. [α]$^{25}_D$–265.2° (c=0.16, MeOH). Purity A:B=>99.5:0.5.

Peak B (125 mg). mp 165° C. (dec.). $^1$H NMR (360 MHz, D$_6$-DMSO) δ1.42–1.60 (1H, m), 1.63–1.87 (2H, m), 1.94–2.08 (1H, m), 2.23 (3H, s), 3.14–3.86 (11H, m), 5.26–5.38 (1H, m), 6.76 (1H, d, J=7.0 Hz), 7.08–7.17 (2H, m), 7.22 (1H, brs), 7.28–7.38 (1H, m), 7.50–7.59 (1H, m), 7.70 (1H, d, J=8.5 Hz), 7.78–7.83 (1H, m), 9.41 (1H, brs), 10.54 (1H, brs). MS (CI) m/e 436 [MH]⁺. [α]$^{25}_D$+244.2° (c=0.18, MeOH). Purity A:B=1:99.

EXAMPLE 15

Chiral Separation of N-[3(R,S)-2,3-dihydro-5-(cis-2,6-dimethylpiperidin-1-yl)-1-methyl-2-oxo-1H-1,4-benzodiazepin-3-yl]N'-[indan-5-yl]urea.

N-[3(R,S)-2,3-Dihydro-5-(cis-2,6-dimethylpiperidin-1-yl)-1-methyl-2-oxo-1H-1,4-benzodiazepin-3-yl]N'-[indan-5-yl]urea (Example 13) (0.95 g) was dissolved in 3:1 chloroform:methanol (20 ml). The enantiomers were separated as described in Example 5.

Peak A (0.44 g). mp 160° C. (dec.). 1H NMR (360 MHz, D$_6$-DMSO) δ0.93–1.10 (3H, m), 1.28–2.08 (11H, m), 2.70–2.85 (4H, m), 3.34–3.54 (3H, m), 3.78–4.68 (2H, m), 5.28–5.44 (1H, m), 7.02–7.30 (4H, m), 7.64–7.96 (4H, m), 9.30 (1H, brs), 10.18 and 10.30 (1H, 2×brs). MS (CI) m/e 460 [MH]⁺. Anal. Found C, 65.32; H, 7.14; N, 13.73. C$_{27}$H$_{33}$N$_5$O$_2$. HCl requires C, 65.38; H, 6.91; N, 14.12%. [α]$^{25}_D$–194.4° (c=0.50, MeOH). Purity A:B>99.5:0.5.

Peak B (0.45 g). mp 159° C. (dec.). $^1$H NMR (360 MHz, D$_6$-DMSO) δ0.93–1.10 (3H, m), 1.28–2.08 (11H, m), 2.70–2.85 (4H, m), 3.34–3.54 (3H, m), 3.78–4.68 (2H, m), 5.28–5.44 (1H, m), 7.02–7.30 (4H, m), 7.64–7.96 (4H, m), 9.39 (1H, brs), 10.20 and 10.35 (1H, 2×brs). MS (CI) m/e 460 [MH]⁺. Anal. Found C, 65.14; H, 7.41; N, 13.52. C$_{27}$H$_{33}$N$_5$O$_2$.HCl.0.25(Et$_2$O)).0.15(H$_2$O) requires C, 65.01; H, 7.17; N, 13.54%. [α]$^{25}_D$+183.5° (c=0.50, MeOH). Purity A:B=0.7:99.3.

EXAMPLE 16

N-[3(R,S)-2,3-Dihydro-5-(cis-2,6-dimethylmorpholin-4-yl)-1-methyl-2-oxo-1H-1,4-benzodiazepin-3-yl]N'-[3-methylphenyl]urea a) 1,2-Dihydro-5-(cis-2,6-dimethylmorpholin-4-yl)-1-methyl-3H-1,4-benzodiazepin-2-one Prepared as described in Example 4c), from 1-methyl-1,2,3,4-tetrahydro-3H-1,4-benzodiazepin-2,5-dione (10 g) and cis-2,6-dimethylmorpholine (6.5ml). $^1$H NMR (2501 MHz, CDCl$_3$) δ1.10 (3H, d, J=7 Hz), 1.24 (3H, d, J=7 Hz), 2.40–2.76 (2H, m), 3.20–3.88 (8H, m), 4.29 (1H, d, J=12 Hz), 7.19–7.39 (2H, m), 7.47–7.60 (2H, m).

b) 1,2-Dihydro-5-(cis-2,6-dimethylmorpholin-4-yl)-1-methyl-3-oximido-3H-1,4-benzodiazepin-2-one Prepared as described in Example 4), from 1,2-dihydro-5-(cis-2,6-dimethylmorpholin-4-yl)-1-methyl-3H-1,4-benzodiazepin-2-one (4.8 g). $^1$H NMR (360 MHz, D$_6$-DMSO) δ1.80 (6H, brs), 2.42–2.64 (2H, m), 3.80–4.20 (7H, brm), 7.30 (1H, dd, J=7.0 and 7.0 Hz), 7.46–7.60 (3H, m), 10.10–10.42 (1H, 2×brs). MS (CI) m/e 317 [MH]⁺.

c) 1,2-Dihydro-5-(cis-2,6-dimethylmorpholin-4-yl)-1-methyl-3-(O-ethylaminocarbonyl)oximido-3H-1,4-benzodiazepin-2-one Prepared as described in Example 4e), from 1,2-dihydro-5-(cis-2,6-dimethylmorpholin-4-yl)-1-methyl-3-oximido-3H-1,4-benzodiazepin-2-one (1.5 g). $^1$H NMR (360 MHz, CDCl$_3$) δ1.09–1.26 (9H, m), 2.52–3.40 (2H, brm), 3.22–3.92 (8H, m), 4.36–4.44 and 4.70–4.92 (1H, brm), 6.39 (1H, m), 7.24–7.34 (3H, m), 7.53 (1H, dd, J=7.0 and 7.0 Hz). MS (CI) m/e 388 [MH]⁺.

d) N-[3(R,S)-2,3-Dihydro-5-(cis-2,6-dimethylmorpholin-4-yl-1-methyl-2-oxo-1H-1,4-benzodiazepin-3-yl]N'-[3-methylphenyl]urea To a solution of the product of part c) (1.52 g) in methanol (80 ml) was added 10% palladium on carbon (400 mg, 26% (w/w)). The mixture was hydrogenated at 40 psi for 2 h and then the catalyst was filtered off and washed with methanol. The solvent was evaporated in vacuo to give the amine (1.06 g).

To a stirred solution of the amine (1.06 g) in anhydrous tetrahydrofuran (10 ml) under an atmosphere of nitrogen, at 0° C., was added m-tolyl isocyanate (0.45 ml) dropwise. After stirring at 0° C. for 5 min the desired compound (1.45 g) was collected by filtration and recrystallised from petrol:ethyl acetate (1:1). mp 253°–255° C. $^1$H NMR (360 MHz, CDCl$_3$) δ1.11 (3H, d, J=6.2 Hz), 1.17 (3H, d, J=6.2 Hz), 2.29 (3H, s), 2.41–2.47 (1H, m), 2.59–2.66 (1H, m), 3.41–3.45 (4H, m), 3.62–3.80 (3H, m), 5.34 (1H, d, J=8.0 Hz), 6.69–6.73 (1H, m), 6.83 (1H, d, J=7.1 Hz), 7.08–7.16 (3H, m), 7.24–7.35 (3H, m), 7.52–7.57 (2H, m). MS (CI) m/e 436 [MH]⁺.

EXAMPLE 17

N-[3(R,S)-2,3-Dihydro-5-(4-methylpiperidin-1-yl)-2-oxo-1-propyl-1H-1,4-benzodiazepin-3-yl]N'-[3-methylphenyl]urea a) N-Propylisatoic anhydride To a stirred solution of isatoic anhydride (100 g) and propyl iodide (66 ml) in dimethylfomamide (600 ml) at 0° C., under nitrogen, was added sodium hydride (28 g of a 55% dispersion in mineral oil) portionwise. The mixture was allowed to warm to room temperature and stirred for 18 h. The solvent was then removed in vacuo and the residue partitioned between ethyl acetate (1000 ml) and water (500 ml). The organic phase was separated, washed with brine (2×500 ml), dried ($MgSO_4$) and evaporated. The residue was triturated with anhydrous diethyl ether to give the title compound (57 g). $^1$H NMR (360 MHz, $CDCl_3$) δ1.06 (3H, t, J=7.5 Hz), 1.75–1.86 (2H, m), 4.01–4.05 (2H, m), 7.17 (1H, d, J=8.5 Hz), 7.26–7.32 (1H, m), 7.73–7.78 (1H, m), 8.17 (1H, dd, J=7.9 and 1.7 Hz). MS (CI) m/e 205 [MH]$^+$.

b) 1-Propyl-1,2,3,4-tetrahydro-3H-1,4-benzodiazepin-2.5-dione

N-Propylisatoic anhydride (56 g) and glycine (20.5 g) were heated at reflux in glacial acetic acid (375 ml), under nitrogen, for 5 h. The solution was concentrated in vacuo and the residue partitioned between dichloromethane (1500 ml) and saturated sodium bicarbonate solution (1000 ml). The organic phase was separated, dried ($MgSO_4$) and evaporated to afford an orange gum. The gum was cooled to 0° C. then triturated with anhydrous diethyl ether to give the bis-lactam (47 g) as colourless needles. $^1$H NMR (360 MHz, $CDCl_3$) δ0.84 (3H, t, J=7.3 Hz), 1.46–1.66 (2H, m), 3.52–3.64 (1H, m), 3.70–3.85 (2H, m), 4.18–4.28 (1H, m), 7.22–7.36 (3H, m), 7.55 (1H, d of t, J=7.5 and 1.7 Hz), 7.90 (1H, dd, J=7.8 and 1.7 Hz). MS (CI) m/e 219 [MH]$^+$.

c) N-[3(R,S)-2,3-Dihydro-5-(4-methylpiperidin-1-yl)-2-oxo-1-propyl-1H-1,4-benzodiazepin-3-yl]N'-[3-methylphenyl]urea Prepared as described in Example 4, steps c)-f), from 1-propyl-1,2,3,4-tetrahydro-3H-1,4-benzodiazepin-2,5-dione (30 g) and 4-methylpiperidine (16.3 ml). mp 133°–136° C. $^1$H NMR (360 MHz, $CDCl_3$) δ0.79 (3H, t, J=7.4 Hz), 0.96 (3H, d, J=6.4 Hz), 1.10–1.75 (7H, m), 2.28 (3H, s), 2.76–3.02 (2H, m), 3.55–3.86 (2H, m), 3.91–4.04 (1H, m), 4.23–4.36 (1H, m), 5.35 (1H, d, J=8.2 Hz), 6.79–6.84 (2H, m), 7.11–7.14 (2H, m), 7.24–7.40 (4H, m), 7.51–7.59 (2H, m). MS (CI) m/e 448 [MH]$^+$.

EXAMPLE 18

Chiral separation of N-[3(R,S)-2,3-dihydro-5-(4-methylpiperidin-1-yl)-2-oxo-1-propyl-1H-1,4-benzodiazepin-3-yl]N'-[3-methylphenyl]urea N-[3(R,S)-2,3-Dihydro-5-(4-methylpiperidin-1-yl)-2-oxo-1-propyl-H-1,4-benzodiazepin-3-yl]N'-[3-methylphenyl]urea (1.74 g) was dissolved in 9:1 chloroform:methanol (11 ml). 440 µl of this solution was injected onto a dinitrobenzoyl leucine column (250×20 mm i.d., 5 µm) per min using 95:5:1 1-chlorobutane:methanol:acetic acid as the mobile phase. Using a flow rate of 20 ml/min and u.v. detection at 330 nm, the two enantiomers were efficiently separated and isolated as described in Example 5.

Peak A: (0.68 g). mp 167°–170° C. $^1$H NMR (360 MHz, $D_6$-DMSO) δ0.66–1.96 (13H, m), 2.22 (3H, s), 3.00–4.20 (9H, m), 5.30–5.34 (1H, m), 6.74–6.76 (1H, m), 7.08–7.22 (2H, m), 7.22 (1H, s), 7.24–7.40 (1H, m), 7.56–7.62 (1H, m), 7.78–7.98 (3H, m), 9.46–9.58 (1H, m), 10.52–10.64 (1H, m). MS (CI) m/e 448 [MH]$^+$. $[\alpha]^{22}_D$–211.3° (c=0.56, MeOH). Purity A:B=>99.5:0.5.

Peak B: (0.71 g) mp 164°–167° C. $^1$H NMR (360 MHz, $D_6$-DMSO) δ0.66–1.96 (13H, m), 2.22 (3H, s), 3.00–4.20 (9H, m), 5.30–5.34 (1H, m), 6.74–6.76 (1H, m), 7.08–7.22 (2H, m), 7.22 (1H, s), 7.24–7.40 (1H, m), 7.56–7.62 (1H, m), 7.78–7.98 (3H, m), 9.46–9.58 (1H, m), 10.52–10.64 (1H, m). MS (CI) m/e 448 [MH]$^+$. $[\alpha]^{22}_D$+201.8° (c=0.57, MeOH). Purity A:B=2:98.

EXAMPLE 19

N-[3(R,S)-2,3-Dihydro-1-methyl-2-oxo-5-(4-trifluoromethylpiperidin-1-yl)-1H-1,4-benzodiazepin-3-yl]N'-[3-methylphenyl]urea a) 4-Trifluoromethylpiperidine hydrochloride A solution of 2-chloro-4-trifluoromethylpyridine (11.6 g) in glacial acetic acid (70 ml), containing 10% palladium on carbon (2.4 g, 21% (w/w)) was hydrogenated at 40 psi for 4 h. Concentrated hydrochloric acid (20 ml) was added and hydrogenation continued for a further 1 h. The catalyst was filtered off and the filtrate evaporated in vacuo to afford 4-trifluoromethylpyridinium hydrochloride.

The pyridium hydrochloride was dissolved in ethanol (70 ml) and water (5ml), and hydrogenated at 40 psi at 60° C. in the presence of 5% rhodium on carbon (4.8 g, 41% (w/w)). After 4 h the catalyst was filtered off and the filtrate evaporated in vacuo. The residue was azeotroped with toluene (30 ml) and then triturated with anhydrous diethyl ether. $^1$H NMR (250 MHz, D6-DMSO) δ1.62–2.01 (4H, m), 2.56–3.00 (3H, m), 3.18–3.39 (2H, m), 9.00–9.60 (2H, 2×brs). MS (CI) m/e 154 [MH]$^+$.

b) 1,2-Dihydro-1-methyl-3-(O-ethylaminocarbonyl)oximido-5-(4-trifluoromethylpiperidin-1-yl)-3H-1,4-benzodiazepin-2-one Prepared as described in Example 4 steps c)-e), from 1-methyl-1,2,3,4-tetrahydro-3H-1,4-benzodiazepin-2,5-dione (11.1 g) and 4-trifluoromethylpiperidine hydrochloride (10.63 g). $^1$H NMR (360 MHz, $CDCl_3$) δ1.13 (3H, t, J=7.1 Hz), 1.70–.240 (5H, m), 2.80–3.04 (2H, br m), 3.22–3.30 (2H, m), 3.45 (3H, s), 3.50–4.94 (2H, brm), 6.00–6.10 and 6.35–6.39 (1H, 2×br s), 7.24–7.38 (3H, m), 7.53 (1H, d of t, J=7.2 and 1.5 Hz). MS (CI) m/e 426 [MH]$^+$.

c) N-[3(R,S)-2,3-Dihydro-1-methyl-2-oxo-5-(4-trifluoromethylpiperidin-1-yl)-1H-1,4-benzodiazepin-3-yl]N'-[3-methylphenyl]urea The amine was prepared as in Example 4f), from the product of part b). The title compound was then prepared from the amine and m-tolyl isocyanate (490 µl) as described in Example 16d). mp 248°–250° C. $^1$H NMR (360 MHz, $D_6$-DMSO) δ1.30–2.24 (8H, m), 2.40–3.00 (2H, brm), 3.04–4.20 (5H, brm), 5.22–5.40 (1H, brs), 6.75 (1H, d, J=7.2 Hz), 7.08–7.17 (2H, m), 7.22 (1H, s), 7.24–7.46 (1H, brm), 7.50–7.60 (1H, m), 7.68–7.72 (1H, m), 7.80–8.00 (2H, m), 9.46 (1H, brs), 10.72 (1H, brs). MS (CI) m/e 474 [MH]$^+$.

EXAMPLE 20

Chiral separation of N-[3(R,S)-2,3-dihydro-1-methyl-2-oxo-5-(4-trifluoromethylpiperidin-1-yl)-1H-1,4-benzodiazepin-3-yl]N'-[3-methylphenyl]urea N-[3(R,S)-2,3-Dihydro-1-methyl-2-oxo-5-(4-trifluoro methylpiperidin-1-yl)-1H-1,4-benzodiazepin-3-yl]N'-[3-methylphenyl]urea (1.44 g) was dissolved in 9:1 chloroform:methanol (20 ml). 1.5 ml of this solution was injected onto a dinitrobenzoyl leucine column (250×20 mm i.d., 5 µm) per run using 95:5:1 1-chlorobutane:methanol:acetic acid as the mobile phase. The two enantiomers were efficiently separated and isolated as described in Example 5.

Peak A (704 mg) mp 185°–188°. $^1$H NMR (360 MHz, D6-DMSO) δ1.30–2.24 (8H, m), 2.40–3.00 (2H, m), 3.04–4.20 (5H, brm), 5.22–5.40 (1H, brs), 6.75 (1H, d, J=7.2 Hz), 7.08–7.17 (2H, m), 7.22 (1H, s), 7.24–7.46 (1H, brm), 7.50–7.60 (1H, m), 7.68–7.72 (1H, m), 7.80–8.00 (2H, m), 9.46 (1H, brs), 10.72 (1H, brs). MS (CI) m/e 474 [MH]$^+$. $[\alpha]^{22}_D$–227.7° (c=0.53, MeOH). Purity A:B=>99.5:0.5.

Peak B (0.71 g) mp 185°–188° C. $^1$H NMR (360 MHz, CDCl$_3$) δ1.44–1.62 (1H, m), 1.66–1.98 (3H, m), 2.08–2.22 (1H, m), 2.29 (3H, s), 2.58–3.40 (2H, m), 3.43 (3H, s), 3.58–3.68 (1H, m), 4.01–4.09 (1H, m), 5.30 (1H, d, J=7.9 Hz), 6.59 (1H, d, J=7.8 Hz), 6.95 (1H, brs), 7.05–7.08 (1H, m), 7.14 (1H, dd, J=7.8 and 7.8 Hz), 7.23–7.34 (3H, m), 7.52–7.56 (2H, m). MS (CI) m/e 474 [MH]$^+$. $[\alpha]^{22}_D$+211° (c=0.52, MeOH). Purity A:B=2:98.

EXAMPLE 21

N-[3(R,S)-2,3-Dihydro-5-(2,2-dimethylpiperidin-1-yl)-1-methyl-2-oxo-1H-1,4,benzodiazepin-3-yl]N'-[3-methylphenyl]urea a) 6,6-Dimethylpiperidin-2-one To a solution of 2-2-dimethylcyclopentanone (2 g) in formic acid (97%, 27 ml) was added portionwise hydroxylamine-O-sulphonic acid (3.02 g) over a period of 10 min. The mixture was heated at reflux for 5 h. After cooling, ice was added and the mixture neutralised with sodium hydroxide solution (4M, ~200 ml) and then extracted with dichloromethane (4×50 ml). The combined organic layers were dried (Na$_2$SO$_4$) and the solvent evaporated in vacuo. The residue was chromatographed on silica gel using a gradient of 0 to 20% ethyl acetate in dichloromethane, followed by 10% methanol in dichloromethane as eluant, to obtain a colourless solid. This was triturated with hexane to afford the title compound (0.43 g). mp 128°–131° C. $^1$H NMR (360 MHz, CDCl$_3$) δ1.25 (6H, s), 1.64–1.68 (2H, m), 1.80–1.88 (2H, m), 2.31 (2H, t, J=6.6 Hz), 5.82 (1H, br s). MS (CI) m/e 128 [MH]$^+$.

b) 2,2-Dimethylpiperidine

To a solution of lithium aluminium hydride in diethyl ether (66 ml of a 1.0 m solution) under nitrogen at reflux, was added a suspension of 6,6-dimethylpiperidin-2-one (4.2 g) in anhydrous diethyl ether (120 ml) portionwise over a period of 15 min. The mixture was heated at reflux under nitrogen for 5 h, then cooled to 0° C. Water (2.5 ml) was added dropwise, followed by aqueous sodium hydroxide (2.5 ml of a 4N solution) and water (7.5 ml). The resultant granular solid was removed by filtration, the filtrate dried (Na$_2$SO$_4$) and evaporated. The pale yellow oil was distilled under reduced pressure to afford the title piperidine (2.7 g). bp 70° C./60 mmHg. $^1$H NMR (360 MHz, CDCl$_3$) δ1.13 (6H, s), 1.36–1.50 (4H, m), 1.53–1.62 (2H, m), 2.83–2.87 (2H, m). MS (CI) m/e 114 (MH)$^+$.

c) 1,2-Dihydro-5-(2,2-dimethylpiperidin-1-yl)-1-methyl-3-(O-ethylaminocarbonyl)oximido-3H-1,4-benzodiazepin-2-one Prepared as described in Example 4 steps c) to e), from 1-methyl-1,2,3,4-tetrahydro-3H-1,4-benzodiazepin-2,5-dione (4.54 g), and 2,2-dimethylpiperidine (2.7 g). $^1$H NMR (360 MHz, CDCl$_3$) δ1.20 and 1.25 (3H, 2xt, J=7.3 Hz), 1.43–1.44 (3H, m), 1.55–1.82 (9H, m), 2.93–3.04 (1H, m), 3.19–3.30 (3H, m), 3.43–3.46 (3H, m), 6.02–6.08 and 6.26–6.32 (1H, m), 7.18–7.34 (2H, m), 7.44–7.52 (2H, m). MS (CI) m/e 386 [MH]$^+$.

d) N-[3(R,S)-2,3-Dihydro-5-(2,2-dimethylpiperidin-1-yl)-1-methyl-2-oxo-1H-1,4-benzodiazepin-3-yl]N'-[3-methylphenyl]urea The amine was prepared as in Example 4f), from the product of part c) (2.3 g). The title compound was then prepared from the crude amine and m-tolyl isocyanate (0.78 ml) as described in Example 6b). mp 235° C. (dec.). $^1$H NMR (360 MHz, CDCl$_3$) δ1.42–1.66 (9H, m), 2.29 (3H, s), 2.80–2.98 (2H, m), 3.42 (3H, s), 5.20 (1H, d, J=7.9 Hz), 6.42–6.50 (1H, m), 6.70–6.86 (2H, m), 7.06–7.16 (2H, m), 7.18–7.28 (3H, m), 7.45–7.52 (1H, m), 7.69 (1H, dd, J=7.8 and 1.6 Hz). MS (CI) m/e 434 [MH]$^+$. Anal. Found: C, 69.13; H, 7.23; N, 16.08. C$_{25}$H$_{31}$N$_5$O$_2$ requires: C, 69.26; H, 7.21; N, 16.15%

EXAMPLE 22

Chiral separation of N-[3(R,S)-2,3-dihydro-5-(2,2-dimethylpiperidin-1-yl)-1-methyl-2-oxo-1H-1,4-benzodiazepin-3-yl]N'-[3-methylphenyl]urea N-[3(R,S)-2,3-Dihydro-5-(2,2-dimethylpiperidin-1-yl)-1-methyl-2-oxo-1H-1,4-benzodiazepin-3-yl]N'-[3-methylphenyl]urea (1.8 g) was dissolved in 9:1 chloroform:methanol (12 ml). 400 µl of this solution was injected onto a dinitrobenzoyl leucine column (250×20 mm i.d., 5 µm) per run using 90:10:1 1-chlorobutane:methanol:acetic acid as the mobile phase. The two enantiomers were efficiently separated and isolated as described in Example 5.

Peak A (0.8 g). mp 150° C. (dec.). $^1$H NMR (360 MHz, d$_6$-DMSO) δ1.17–1.80 (12H, m), 2.23 (3H, s), 2.72–3.82 (5H, m), 5.10–5.28 (1H, m), 6.74 (1H, d, J=7.0 Hz), 7.06–7.36 (4H, m), 7.42–7.58 (1H, m), 7.61–7.98 (3H, m), 9.42 (1H, brs). MS (CI) m/e 434 [M+1]$^+$. $[\alpha]^{22}_D$–423.1° (c=0.68, MeOH). Purity A:B=>99.5:0.5.

Peak B (0.8 g). mp 150° C. (dec.). $^1$H NMR (360 MHz, d$_6$-DMSO) δ1.12–1.83 (12H, m), 2.23 (3H, s), 2.83–3.70 (5H, m), 5.08–5.30 (1H, m), 6.74 (1H, d, J=6.9 Hz), 7.04–7.31 (4H, m), 7.40–7.57 (1H, m), 7.62–7.96 (3H, m), 9.37 (1H, brs). MS (CI) m/e 434 [MH]$^+$. $[\alpha]^{22}_D$+420.5° (c=0.67, MeOH). Purity A:B=1.3:98.7.

EXAMPLE 23

N-[3(R,S)-2,3-Dihydro-1-methyl-2-oxo-5-(cis-2,4,6-trimethylpiperidin-1-yl)-1H-1,4-benzodiazepin-3-yl]N'-[3-methylphenyl]urea a) 1,2-Dihydro-1-methyl-3-(O-ethylaminocarbonyl)oximido-5-(cis-2,4,6-trimethylpiperidin-1-yl)-3H-1,4-benzodiazepin-2-one Prepared as described in Example 4 steps c)-e) from 1-methyl-1,2,3,4-tetrahydro-3H-1,4-benzodiazepin-2,5-dione (5 g) and cis-2,4,6-trimethylpiperidine (11.7 g). $^1$H NMR (360 MHz, CDCl$_3$) δ0.92–1.50 (14H, m), 1.68–2.23 (3H, m), 3.16–3.30 (2H, m), 3.41–3.47 (3H, m), 3.82–3.88 and 4.07–4.18 (1H, m), 4.54–4.76 (1H, m), 6.13–6.20 and 6.32–6.45 (1H, m), 7.18–7.38 (3H, m), 7.42–7.50 (1H, m). MS (CI) m/e 400 [MH]$^+$.

b) N-[3(R,S)-2,3-Dihydro-1-methyl-2-oxo-5-(cis-2,4,6-trimethylpiperidin-1-yl)-1H-1,4-benzodiazepin-3-yl]N'-[3-methylphenyl]urea The amine was prepared as in Example 4f) from the product of part a). The title compound was then prepared from the crude amine and m-tolyl isocyanate (0.8 ml) as described in Example 6b) and recrystallised from ethyl acetate:dichloromethane (9:1). mp 223°–225° C. $^1$H NMR (360 MHz, CDCl$_3$) δ0.76–1.18 (11H, m), 1.55–1.90 (3H, m), 2.22 (3H, s), 3.29–3.38 (4H, m), 3.56–3.72 (1H, m), 4.97 (1H, d, J=8.3 Hz), 6.71 (1H, d, J=7.0 Hz), 7.05–7.13 (3H, m), 7.16 (1H, s), 7.35 (1H, t, J=7.0 Hz), 7.55 (1H, d, J=7.9 Hz), 7.61–7.65 (2H, m), 8.85 (1H, s). MS (CI) m/e 448

[MH]⁺. Anal. Found: C, 70.00; H, 7.49; N, 15.45. $C_{26}H_{33}N_5O_2$ requires: C, 69.77; H, 7.43; N, 15.65%.

EXAMPLE 24

Chiral separation of N-[3(R,S)-2,3-dihydro-1-methyl-2-oxo-5-(cis-2,4,6-trimethylpiperidin-1-yl)-1H-1,4-benzodiazepin-3-yl]N'-(3-methylphenyl)]urea N-[3(R,S)-2,3-Dihydro-1-methyl-2-oxo-5-(cis-2,4,6-trimethyl piperidin-1-yl)-1H-1,4-benzodiazepin-3-yl]N'-[3-methylphenyl]urea (1.25 g) was dissolved in 9:1 chloroform:methanol (20 ml). The enantiomers were separated as described in Example 5.

Peak A (0.59 g). mp 170° C. (dec.). ¹H NMR (360 MHz, D₆-DMSO) δ0.84–1.74 (11H, m), 1.80–2.32 (6H, m), 3.28–3.84 (4H, m), 4.14–4.48 (1H, m), 5.25–5.44 (1H, m), 6.75 (1H, d, J=7.1 Hz), 7.08–7.36 (4H, m), 7.50–7.62 (1H, m), 7.66–7.94 (3H, m), 9.45 (1H, brs), 10.16 (1H, brs). MS (CI) m/e 448 [MH]⁺. Anal. Found: C, 60.42; H, 7.02; N, 13.35. $C_{26}H_{33}N_5O_2.HCl.1.75 (H_2O)$ requires C, 60.57; H, 7.33; N, 13.58%. $[\alpha]^{22}_D.138.8°$ (c=0.64, MeOH). Purity A:B=>99.5:0.5.

Peak B (0.53 g). mp 170° C. (dec.). ¹H NMR (360 MHz, D₆-DMSO) δ0.84–1.73 (11H, m), 1.80–2.30 (6H, m), 3.32–3.84 (4H, m), 4.16–4.46 (1H, m), 5.24–5.46 (1H, m), 6.75 (1H, d, J=7.1 Hz), 7.07–7.18 (2H, m), 7.20–7.34 (2H, m), 7.50–7.63 (1H, m), 7.66–7.94 (3H, m), 9.45 (1H, brs), 10.14 (1H, brs). MS (CI) m/e 448 [MH]⁺. Anal. Found: C, 62.14; H, 7.10; N, 13.60. $C_{26}H_{33}N_5O_2.HCl.H_2O$ requires C, 62.20; H, 7.23; N, 13.95%. $[\alpha]^{22}_D+138.3°$ (c=0.65, MeOH). Purity A:B=<0.5:99.5.

EXAMPLE 25

N-[3(R,S)-2,3-Dihydro-5-(3,3-dimethylpiperidin-1-yl)-1-methyl-2-oxo-1H-1,4-benzodiazepin-3-yl]N'-[3-methyl phenyl]urea a) 1,2-Dihydro-5-(3,3-dimethylpiperidin-1-yl)-1-methyl-3-oximido-3H-1,4-benzodiazepin-2-one Prepared as described in Example 4, steps c) and d) from 1-methyl-1,2,3,4-tetrahydro-3H-1,4-benzodiazepin-2,5-dione (16.7 g) and 3,3-dimethylpiperidine (10.0 g). ¹H NMR (360 MHz, D₆-DMSO) δ0.69 (3H, s), 0.82 (3H, s), 1.28–1.45 (3H, m), 1.62–1.80 (1H, m), 2.75–3.00 (3H, m), 3.30 (3H, s), 3.50–3.60 (1H, m), 7.25–7.30 (1H, m), 7.40–7.60 (3H, m), 9.95 (1H, br s), 10.20 (1H, br s). TLC (10% MeOH/dichloromethane: silica) Rf=0.40.

b) N-[3(R,S)-2,3-Dihydro-5-(3,3-dimethylpiperidin-1-yl)-1-methyl-2-oxo-1H-1,4-benzodiazepin-3-yl]N'-[3-methylphenyl]urea 1,2-Dihydro-5-(3,3-dimethylpiperidin-1-yl)-1-methyl-3-(O-ethylaminocarbonyl)oximido-3H-1,4-benzodiazepin-2-one (11.4 g) was prepared as described in Example 4e) from the product of part a). The amine was prepared as in Example 4f) from 1,2-dihydro-5-(3,3-dimethylpiperidin-1-yl)-1-methyl-3-(O-ethylamino-carbonyl)oximido-3H-1,4-benzodiazepin-2-one (11.4 g). The title compound was then prepared from the crude amine (8.5 g) and m-tolyl isocyanate (4 ml) as described in Example 6b). mp 213°–215° C. ¹H NMR (360 MHz, CDCl₃) δ0.71 (3H, s), 0.85 (3H, s), 1.30–1.47 (3H, m), 1.64–1.80 (3H, m), 2.22 (3H, s), 2.75–2.82 (1H, m), 2.84–3.00 (2H, m), 3.31 (3H, s), 3.50–3.60 (1H, m), 4.95 (1H, d, J=8.4 Hz), 6.70 (1H, d, J=6.9 Hz), 6.99–7.00 (1H, m), 7.02–7.20 (3H, m), 7.34–7.40 (1H, m), 7.50–7.70 (3H, m), 8.80 (1H, m).

EXAMPLE 26

Chiral separation of N-[3(R,S)-2,3-dihydro-5-(3,3-dimethylpiperidin-1-yl)-1-methyl-2-oxo-1H-1,4-benzodiazepin-3-yl]N'-[3-methylphenyl]urea (–)-N-[2,3-dihydro-(3,3-dimethylpiperidin-1-yl)-1-methyl-2-oxo-1H-1,4-benzodiazepin-3-yl]N'-[3-methylphenyl] urea was prepared from the racemate analogously to Example 5. ¹H NMR (360 MHz, D₆-DMSO) δ0.56 (3H, s), 0.81 (3H, s), 1.40–1.90 (4H, m), 2.24 (3H, s), 3.17 (1H, d, J=11.8 Hz), 3.22–3.60 (2H, m), 3.41 (3H, s), 4.00–4.10 (1H, m), 5.41 (1H, d, J=6.7 Hz), 6.77 (1H, d, J =8.2 Hz), 7.08–7.18 (3H, m), 7.23 (1H, s), 7.34 (1H, d, J=6.7 Hz), 7.58 (1H, t, J=7.3 Hz), 7.79 (1H, d, J=7.6 Hz), 7.78–7.95 (2H, m), 9.26 (1H, s), 10.50 (1H, m). MS (CI) m/e 434 [MH]⁺. Purity A:B 99.5:0.5. $[\alpha]^{25}_D–86.3°$ (C=0.75, CH₂Cl₂).

EXAMPLE 27

N-[3(R,S)-2,3-Dihydro-5-(4,4,dimethylpiperidin-1-yl)-2-oxo-1-(2,2,2-trifluoroethyl)-1H-1,4-benzodiazepin-3-yl]N'-(3-methylphenyl) urea a) Methyl 2-[N-(2-bromoacetyl)-N-(2,2,2-trifluoroethyl)] aminobenzoate A solution of methyl anthranilate (98.3 g) and trifluoroethyl trichloromethanesulphonate (91.5 g) in m-xylene (200 ml) was heated at reflux for 3 h under nitrogen. The reaction mixture was allowed to cool overnight, then filtered from a white solid, washing well with diethyl ether. The combined filtrates were evaporated in vacuo and the residual oil purified by flash chromatography (silica gel, 10% diethyl ether/hexane) to give methyl 2-[N-(2,2,2-trifluoroethyl)] aminobenzoate, contaminated with trifluoroethyl trichloromethanesulphonate. To a solution of this mixture (35.8 g) in dichloromethane (150 ml), cooled to 1° C. under nitrogen, was added dropwise bromoacetyl bromide (10.1 ml), keeping the temperature below +3° C. The reaction mixture was stirred at 0°±3° C. for 12 min, then 4N NaOH solution (33.4 ml) was added dropwise over 18 min. The cooling bath was removed and the reaction mixture was stirred at room temperature for 4 h. More bromoacetyl bromide (1.6 ml) was added dropwise and the mixture was stirred for a further 6 h. After leaving to stand overnight, the organic layer was separated, washed with 10% citric add (30 ml), brine (30 ml), saturated potassium carbonate solution (30 ml) and brine (30 ml), dried (Na₂SO₄) and evaporated in vacuo to leave a yellow oil. This was purified by flash chromatography (silica gel, 20–25% EtOAc/petroleum ether) to afford the title compound (27.4 g). ¹H NMR (CDCl₃) δ3.58 (1H, d, J=11.4 Hz), 3.64 (1H, d, J=11.3 Hz), 3.83 (1H, m), 3.90 (3H, s), 4.79 (1H, m), 7.49 (1H, d, J=7.8 Hz), 7.57 (1H, t of d, J=7.6 and 1.3 Hz), 7.68 (1H, t of d, J=7.6 and 1.7 Hz), 8.09 (1H, dd, J=7.8 and 1.6 Hz). MS (CI+, NH₃) m/e 373/371 (M+NH₄)⁺.

b) 1,2,3,4-Tetrahydro-1-(2,2,2-trifluoroethyl)-3H-1,4-benzodiazepin-2,5-dione

Ammonia gas was bubbled into a solution of the product of part a) (27.3 g) in anhydrous methanol (150 ml) for 4 h, keeping the temperature at +4°±9° C. The reaction mixture was allowed to stand open overnight then nitrogen was bubbled through the solution for 1 h. The solvent was removed in vacuo and the residue stirred with 5% MeOH/CH₂Cl₂. The solid was filtered off, washed well with more 5% MeOH/CH₂Cl₂, and the combined filtrates were purified by flash chromatography (silica gel, 3–5% MeOH/CH₂Cl₂) to give the title compound (15.2 g). ¹H NMR (CDCl₃) δ3.87 (2H, m), 4.19 (1H, m), 5.03 (1H, m), 6.84 (1H, br s), 7.29

(1H, d, J=8.3 Hz), 7.42 (1H, t of d, J=7.6 and 0.8 Hz), 7.60 (1H, t of d, J=7.6 and 1.6 Hz), 7.93 (1H, dd, J=7.8 and 1.6 Hz). MS (CI+, $NH_3$) m/e 259 $[MH]^+$.

c) 1,2-Dihydro-5-(4,4-dimethylpiperidin-1-yl)-3-(O-ethylaminocarbonyl)oximido-1-(2,2,2-trifluoroethyl)-3H-1,4-benzodiazepin-2-one Prepared by the procedure of Example 4, steps c)-e) from the product of part b) (18.0 g) and 4,4-dimethylpiperidine (3.51 g). $^1$H NMR ($CDCl_3$) δ0.97 and 1.05 (6H, 2×br s), 1.10 and 1.13 (3H, 2×t, J=7.3 Hz), 1.16–1.26 (4H, m), 3.25 (2H, m), 3.39–4.11 (5H, m), 5.24–5.42 (1H, m), 6.16 and 6.33 (1H, 2×br t), 7.31–7.56 (4H, m). MS (CI$^+$, $NH_3$) m/e 454 $[MH]^+$.

d) N-[3(R,S)-2,3-Dihydro-5-(4,4-dimethylpiperidin-1-yl)-2-oxo-1-(2,2,2-trifluoroethyl)-1H-1,4-benzodiazepin-3-yl]N'-(3-methylphenyl) urea Following the procedure of Example 4f), the product of part c) (450 mg) was hydrogenated to give 3-amino-1,2-dihydro-5-(4,4-dimethylpiperidin- 1-yl)-1-(2,2,2-trifluoroethyl)-3H-1,4-benzodiazepin-2-one (313 mg). This was dissolved in anhydrous tetrahydrofuran (6 ml) under nitrogen and cooled with an ice/water bath before adding m-tolyl isocyanate (0.110 ml) dropwise. The mixture was stirred for 40 min before removing the cooling bath and stirring for a further hour. The solvent was removed in vacuo and the residue triturated with diethyl ether (10 ml) to afford the title compound (347 mg); mp 236°–239° C. $^1$H NMR ($CDCl_3$) δ0.96 (6H, s), 1.30–1.50 (4H, m), 2.29 (3H, s), 3.30 (4H, m), 4.08 (1H, m), 5.23 (1H, m), 5.38 (1H, d, J=8.2 Hz), 6.46 (1H, br d, J=7.9 Hz), 6.84–6.88 (2H, m), 7.08–7.17 (2H, m), 7.21 (1H, s), 7.34–7.37 (2H, m), 7.53–7.58 (2H, m). MS (CI+, $NH_3$) m/e 502 $[MH]^+$. Anal. Found: C, 61.21; H, 5.88; N, 13.19% $C_{26}H_{30}F_3N_5O_2$.0.6.$H_2O$.0.1 $C_4H_8O$ requires: C, 61.03; H, 6.21; N, 13.48%.

EXAMPLE 28

Chiral separation of N-[3(R,S)-2,3-dihydro-5-(4,4-dimethylpiperidin-1-yl)-2-oxo-1-(2,2,2-trifluoroethyl)-1H-1,4-benzodiazepin-3-yl]N'-[3-methylphenyl]urea A solution of N-[3(R,S)-2,3-dihydro-5-(4,4-dimethylpiperidin-1-yl)-2-oxo-1-(2,2,2-trifluoroethyl)-1H-1,4-bromodiazepin-3-yl]N'-[3-methylphenyl]urea (330 mg) in 50% $CHCl_3$/EtOH (5 ml) was injected in 0.5 ml volumes onto a dinitrobenzoyl leucine column (250×20.4 mm i.d., 5 μm), eluting with 50% ethanol/hexane at 20 ml/min. The fractions containing each enantiomer were separately evaporated in vacuo, the residues were redissolved in filtered dichloromethane (10 ml) and ethereal hydrogen chloride (2 ml) was added. The solvents were then removed in vacuo and the residues triturated with diethyl ether (5 ml) to give:

Peak A. HCl salt (134 mg); mp 153°–158° C.; $^1$H NMR ($d_6$-DMSO) at 353K: δ0.98 (6H, s), 1.26–1.51 (4H, m), 2.23 (3H, s), 3.41–3.63 (4H, br m), 4.73 (1H, m), 5.15 (1H, m), 5.35 (1H, m), 6.75 (1H, d, J=7.1 Hz), 7.06–7.20 (4H, m), 7.59 (1H, m), 7.78–7.85 (3H, m), 9.16 (1H, br s). MS (CI$^+$, $NH_3$) m/e 502 $[MH]^+$. $[α]^{25}_D$=−195.5° (c=0.2, MeOH). Purity A:B=>99.5:0.5. Anal. Found: C, 55.83; H, 6.04; N, 11.93%. $C_{26}H_{30}F_3N_5O_2$.HCl.1.42 $H_2O$ 0.06 $C_4H_{10}O$ requires C, 55.48; H, 6.11; N, 12.33%.

Peak B. HCl salt (128 mg); mp 145°–151° C.; $^1$H NMR ($d_6$-DMSO) at 353K same as for Peak A. MS (CI$^+$, $NH_3$) m/e 502 $[MH]^+$. $[α]^{25}_D$=+204° (c=0.2, MeOH). ee=99%. Anal. Found: C, 56.67; H, 5.86; N, 12.29%. $C_{26}H_{30}F_3N_5O_2$.HCl0.8 $H_2O$: requires C, 56.53; H, 5.95; N, 12.68%.

EXAMPLE 29

N-[3(R,S)-2,3-Dihydro-5(4,4-dimethylpiperidin-1-yl)-1-ethyl-2-oxo-1H-1,4-benzodiazepin-3-yl]N'-[3-methyl phenyl]urea a) 1,2-Dihydro-5-(4,4-dimethylpiperidin-1-yl)-1-ethyl-3-(O-ethylaminocarbonyl)oximido-3H-1,4-benzodiazepin-2-one Prepared as described in Example 4, steps c) to e) from 1-ethyl-1,2,3,4-tetrahydro-3H-1,4-benzodiazepin-2,5-dione (18 g) and 4,4-dimethylpiperidine (10 g). $^1$H NMR (360MHz, $d_6$-DMSO) δ0.9–1.20 (16H, br m), 2.94–3.03 (2H, m), 3.1–3.96 (5H, br m), 4.26 (1H, m), 7.2–7.7 (5H, m).

b) N-[3(R,S)-2,3-Dihydro-5-(4,4-dimethylpiperidin-1-yl)-1-ethyl-2-oxo-5-(4,4-dimethylpiperidin-1-yl)-1H-1,4-benzodiazepin-3-yl]N'-[3-methyl phenyl]urea The amine was prepared as in Example 4f) from the product of part a) (5.2 g). The title compound was then prepared from the amine and m-tolyl isocyanate (1.6 ml) as described in Example 16d) and recrystallised from petroleum ether.

EXAMPLE 30

Chiral separation of N-[3(R,S)-2,3-dihydro-5-(4,4-dimethylpiperidin-1-yl)-1-ethyl-2-oxo-1H-1,4-benzodiazepin-3-yl]N'-[3-methylphenyl]urea N-[3(R,S)-2,3-Dihydro-5-(4,4-dimethylpiperidin-1-yl)-1-ethyl-2-oxo-1H-1,4-benzodiazepin-3-yl]N'-[3-methylphenyl]urea (2.4 g) was dissolved in 9:1 chloroform:methanol (20 ml). 1 ml of this solution was injected onto a dinitrobenzoyl leucine column (250×20 mm i.d., 5 μM) per run using 96:3:1 chlorobutane: methanol:acetic acid as the mobile phase. Using a flow rate of 20 ml/min and u.v. detection at 330 nm, the two enantiomers were efficiently separated. The fractions containing enantiomer A were combined and evaporated under reduced pressure. The residue was partitioned between ethyl acetate (50 ml) and potassium carbonate solution. The organic phases were separated, dried ($MgSO_4$), filtered and evaporated under reduced pressure to give a foam.

Peak A was purified using the Gilson Prep HPLC using 3:2 acetonitrile/water (containing 0.1% TFA) as mobile phase. The solution containing the desired product was evaporated under reduced pressure to remove the acetonitrile. The aqueous solution was basified with sodium carbonate and extracted with ethyl acetate (3×100 ml). The ethyl acetate extracts were combined, dried ($MgSO_4$), filtered and evaporated to give a foam (0.45 g). The foam was recrystallised from diethyl ether (0.28 g). mp 211°–213° C. Found: C, 69.82; H, 7.24; N, 15.60. $C_{26}H_{33}N_5O_2$ requires C, 69.77; H, 7.43; N, 15.65. $^1$H NMR (360 MHz, $CDCl_3$) δ0.95 (6H, s), 1.09 (3H, t), 1.31 (2H, m), 1.47 (2H, m), 2.28 (3H, s), 3.2 (4H, br m), 3.68 (1H, m), 4.33 (1H, m), 5.30 (1H, d), 6.74 (1H, d), 6.80 (1H, d), 7.07–7.37 (6H, m), 7.52 (2H, m).

EXAMPLE 31

N-[3(R,S)-5-(3-Azabicyclo[3,2,2]nonan-3-yl)-2,3-dihydro-1-methyl-2-oxo-1H-1,4-benzodiazepin-3-yl]-N'-[3-methylphenyl]urea Method A a) 5-(3-Azabicyclo[3,2,2]nonan-3-yl)-1,3-dihydro-2H-1-methyl-3-oximido-1,4-benzodiazepin-2-one Prepared analogously to Example 4, steps c) and d) from 1-methyl-1,2,3,4-tetrahydro-3H-1,4-benzodiazepin-2,5-dione (10.0 g) and 3-azabicyclo[3.2.2]nonane (6.89 g). mp 220°–222° C. $^1$H NMR (360 MHz, $CDCl_3$) δ1.30–2.30

(10H, m), 3.32–3.40 (1H, m), 3.45 (3H, s), 3.47–3.54 (1H, m), 3.74–3.80 (1H, m), 4.66–4.73 (1H, m), 7.20–7.35 (3H, m), 7.49 (1H, ddd, $J_1=J_2=7$ Hz, $J_3=1$ Hz). Found: C, 66.31; H, 6.93; N, 17.07. $C_{18}H_{22}N_4O_2$ requires C, 66.24; H, 6.79; N, 17.17%.

b) 3(R,S)-Amino-5-(3-azabicyclo[3,2,2]nonan-3-yl)-1,3-dihydro-1-methyl-2H-1,4-benzodiazepin-2-one The foregoing oxime (6.68 g) was hydrogenated over 5% rhodium on carbon (6.7 g) in methanol (670 ml) at 40 psi and 60° C. for 6.5 hours. The mixture was filtered then evaporated to give the crude amine which was used immediately in the next step.

c) N-[3(R,S)-5-(3-Azabicyclo[3,2,2]nonan-3-yl)-2,3-dihydro-1-methyl-2-oxo-1H-1,4-benzodiazepin-3-yl]-N'-[3-methylphenyl]urea m-Tolyl isocyanate (3.17 ml) was added to an ice cold solution of the foregoing amine (6.4 g) in anhydrous tetrahydrofuran (70 ml) then left standing at 4° C. for 16 hours. The solution was evaporated and the residue partitioned between potassium carbonate solution (100 ml) and dichloromethane (200 ml). The organic layer was separated and the aqueous re-extracted with dichloromethane (5×100 ml). The combined organics were dried (sodium sulphate) then evaporated and the crude product crystallised from dichloromethane to afford the title compound (1.55 g). mp>242° C. (dec.). $^1$H NMR (360 MHz, $CDCl_3$) δ1.54–2.04 (10H, m), 2.29 (3H, s), 3.26–3.40 (2H, m), 3.42 (3H, s), 3.52–3.60 (2H, m), 5.28 (1H, d, J=8 Hz), 6.44 (1H, d, J=8 Hz), 6.80–6.84 (2H, m), 7.07–7.16 (2H, m), 7.22–7.33 (3H, m), 7.47–7.55 (2H, m). Found: C, 63.39; H, 6.65; N,14.15. $C_{26}H_{31}N_5O_2 \cdot 2H_2O \cdot 0.15CH_2Cl_2$ requires C, 63.54H, 7.20; N, 14.17%.

Method B a) 5-(3-Azabicyclo[3,2,2]nonan-3-yl)-1,3-dihydro-2H-1-methyl-3-(O-(ethylaminocarbonyl)oximido)-1,4-benzodiazepin-2-one 5-(3-Azabicyclo[3,2,2]nonan-3-yl)-1,3-dihydro-2H-1-methyl-3-oximido-1,4-benzodiazepin-2-one (5.17 g) and ethylisocyanate (1.9 ml) were heated at 60° C. in anhydrous tetrahydrofuran (200 ml) for 18 hours. The solvent was evaporated and the residue was purified by column chromatography on silica using dichloromethane _1% methanol/dichloromethane to afford a cream foam (5.53 g, 90%, mixture of E/Z isomers). mp 168° C. $^1$H NMR (360 MHz, $CDCl_3$) δ1.10 and 1.12 (3H, each t, J=7 Hz), 1.24–1.96 (9H, m), 2.16–2.28 (1H, m), 3.12–3.36 (3H, m). 3.38–3.52 (1H, m) overlapped with 3.44 and 3.45 (3H, each s), 3.58–3.70 (1H, m), 4.56–4.78 (1H, m), 6.13–6.22 and 6.36–6.44 (1H, each m), 7.18–7.52 (4H, m).

b) 3(R,S)-Amino-5-(3-azabicyclo[3,2,2]nonan-3-yl)-1,3-dihydro-1-methyl-2H-1,4-benzodiazepin-2-one 5-(3-Azabicyclo[3,2,2]nonan-3-yl)-1,3-dihydro-2H-1-methyl-3-(O(ethylaminocarbonyl)oximido)-1,4-benzodiazepin-2-one (5.4 g) was hydrogenated at 40 psi in methanol (500 ml) over 10% palladium on carbon (1.8 g) for 3 hours at room temperature. The mixture was filtered then evaporated to dryness to afford the title amine (4.45 g)

c) N-[3(R,S)-5-(3-Azabicyclo[3,2,2]nonan-3-yl)-2,3-dihydro-1-methyl-2-oxo-1H-1,4-benzodiazepin-3-yl]-N'-[3-methylphenyl]urea The foregoing amine (4.45 g) in anhydrous tetrahydrofuran (15 ml) was treated with m-tolylisocyanate (1.9 ml). After standing for 10 minutes the precipitate was collected to afford the title compound free base (4.90 g) which had the same chromatographic and spectroscopic characteristics as the product obtained using Method A.

EXAMPLE 32

N-[3(R,S)-2,3-Dihydro-5-((1S,4S)-5-methyl-2,5-diazabicyclo-[2,2,1]heptan-2-yl)-2-oxo-1-propyl-1H-1,4-benzodiazepin-3-yl]-N'-[3-methylphenyl]urea a) 1,3-Dihydro-5-((1S,4S)-5-methyl-2,5-diazabicyclo-[2,2,1]heptan-2-yl)-2H-1-propyl-1,4-benzodiazepin-2-one Prepared analogously to Example 4c) from 1-propyl-1,2,3,4-tetrahydro-3H-1,4-benzodiazepin-2,5-dione (5.0 g) and (1S,4S)-2-methyl-2,5-diazabicyclo[2.2.1]heptane dihydrobromide (17.3 g), J. Org. Chem. 1990, 55, 1684–1687).

b) 1,3-Dihydro-5-((1S,4S)-5-methyl-2,5-diazabicyclo[2,2,1]heptan-2-yl)-2H-3-oximido-1-propyl-1,4-benzodiazepin-2-one Potassium t-butoxide (3.6 g) was added in portions to a stirred, cooled (−20° C.) suspension of 1,3-dihydro-5-((1S,4S)-5-methyl-2,5-diazabicyclo[2,2,1]heptan-2-yl-2H-1-propyl-1,4-benzodiazepin-2-one (2.0 g) in anhydrous toluene (250 ml) under a nitrogen atmosphere. After stirring at −20° C. for 30 minutes isopentylnitrite (1.9 ml) was added and the reaction mixture was stirred at −20° C. for 1 hour then at room temperature for 3 days. The mixture was re-cooled to −20° C. and further potassium t-butoxide (1.8 g) and isopentylnitrite (1 ml) were added. The mixture was stirred at −20° C. for 1 hour then at room temperature for 1 day. The reaction mixture was treated with solid carbon dioxide then evaporated to dryness. The residue was purified by column chromatography on alumina using dichloromethane—10% methanol/dichloromethane (containing 1% ammonia) to afford the oxime (0.60 g). MS, m/z=341 for $M^+$.

c) 3(R,S)-Amino-1,3-dihydro-5-((1S,4S)-5-methyl-2,5-diazabicyclo-[2,2,1]heptan-2-yl)-2H-1-propyl-1,4-benzodiazepin-2-one Trifluoroacetic acid (1.36 ml) and activated zinc powder (Fieser and Fieser, 1967, Volume 1, 1276, 1.14 g) were added to a stirred solution of the foregoing oxime (0.6 g) in glacial acetic acid (70 ml) at 40° C. then the mixture was stirred at this temperature for 6 hours. The reaction mixture was cooled, filtered then evaporated to dryness to give the crude amine trifluoroacetate.

d) N-[3(R,S)-2,3-Dihydro-5-((1S,4S)-5-methyl-2,5-diazabicyclo[2.2.1]heptan-2-yl)-2-oxo-1-propyl-1H-1,4-benzodiazepin-3-yl]-N'-[3-methylphenyl]urea Triethylamine (0.3 ml) was added to a stirred suspension of the foregoing amine trifluoroacetate in anhydrous tetrahydrofuran (30 ml). The reaction mixture was then treated with m-tolylisocyanate (0.3 ml) and the reaction mixture was stirred at room temperature for 2 hours. The reaction mixture was evaporated to dryness then the residue was partitioned between ethyl acetate (50 ml) and 1M citric acid (50 ml). The organic layer was extracted with a further portion of 1M citric acid (50 ml) and the combined aqueous was washed with ethyl acetate (3×50 ml) then basified to pH>9 with sodium bicarbonate and extracted with ethyl acetate (3×50 ml). The combined organics were dried (sodium sulphate) then evaporated to dryness to give a solid which was purified by column chromatography on silica using dichloromethane—20% methanol/dichloromethane (containing 1% ammonia). The resulting solid was recrystallised from ethanol/water to afford the title compound (25 mg) as a 1:1 mixture of diastereomers. mp 126°–128° C. MS, $CI^+$, m/z= 461 for $(M+H)^+$. Found: C, 65.07; H, 7.08; N, 16.94. $C_{26}H_{32}N_6O_2 \cdot 1.25H_2O$ requires C, 64.64; H, 7.20; N, 17.39%.

EXAMPLE 33

(−)-N-[5-(3-Azabicyclo[3,2,2]nonan-3-yl)-2,3-dihydro-1-methyl-2-oxo-1H-1,4-benzodiazepin-3-yl]-N'-[3-methyl phenyl]urea Hydrochloride The racemic compound (Example 31, 1.5 g) was separated into its enantiomers using semi-preparative chiral HPLC on a Pirkle dinitrobenzoylleucine column (5µ) [(250×21.4)mm] eluting with 3% methanol in 1chlorobutane (including 1% acetic acid). Flow rate 20 ml/minute, U.V. detection at 290 nm. Analysis was performed on an analytical Pirkle dinitrobenzoylleucine column (5µ) [(250×4.6)mm] eluting with 5% methanol in 1-chlorobutane (including 1% acetic acid). Flow rate 1 ml /minute, U.V. detection at 250 nm.

The free base was liberated and obtained as a colourless solid (680 mg). The hydrochloride salt had mp 188°–190° C. (dec.) (ethyl acetate/acetone (10:1). Rf 0.55 in dichloromethane/methanol (9:1) on silica plates. MS, CI$^+$, m/z=446 for (M+H)$^+$. $[\alpha]^{23° C.}_D$=−216° (c=0.2, methanol). Found: C, 63.75; H, 6.99; N, 13.98. $C_{26}H_{31}N_5O_2 \cdot HCl0.5H_2O$ requires C, 63.60; H, 6.77; N, 14.26%. HPLC: (Pirkle dinitrobenzoylleucine column, 5% methanol in 1-chlorobutane (including 1% acetic acid)): >99% ee ($T_t$, =5.6 minutes). HPLC: (Spherisorb 5 µm Phenyl column [(250×4.6)mm], 50% acetonitrile/50% of 0.2% triethylamine in water and 50 mM potassium phosphate, pH=3): >99% chemically pure.

EXAMPLE 34

(+)-N-[5-(3-Azabicyclo[3,2,2]nonan-3-yl)-2,3-dihydro-1-methyl-2-oxo-1H-1,4-benzodiazepin-3-yl]-N'-[3-methyl phenyl]urea Hydrochloride The title compound was obtained (660 mg) using the procedure described in Example 33. The hydrochloride salt had mp 189°–191° C. (dec.) (ethyl acetate/acetone (10:1)). Rf 0.55 in dichloromethane/methanol (9:1) on silica plates. MS, CI$^+$, m/z=446 for (M+H)$^+$. $[\alpha]^{23° C.}_D$=+222° (c=0.2, methanol). Found: C, 63.59; H, 7.05; N, 13.86. $C_{26}H_{31}N_5O_2 \cdot HCl \cdot 0.5H_2O$ requires C, 63.60; H, 6.77; N, 14.26%. HPLC: (Pirkle dinitrobenzoylleucine column, 5% methanol in 1-chlorobutane (including 1% acetic acid)): 99% ee ($R_t$=8.24 minutes). HPLC: (Spherisorb 5 µm Phenyl column [(250×4.6)mm], 50% acetonitrile/50% of 0.2% triethylamine in water and 50 mM potassium phosphate, pH=3): >99% chemically pure.

EXAMPLE 35

N-[3(R,S)-5-(3-Azabicyclo[3,2,2]nonan-3-yl)-2,3-dihydro-1-methyl-2-oxo-1H-1,4-benzodiazepin-3-yl]-N'-[3-fluorophenyl]urea The title compound was obtained (450 mg) from 3-fluorophenyl isocyanate and 3(R,S)-amino-5-(3-azabicyclo [3,2,2]nonan-3-yl)-1,3-dihydro-1-methyl-2H-1,4-benzodiazepin-2-one as described in Example 31, Method A. mp 196°–197° C. (dichloromethane/diethyl ether). MS, CI$^+$, m/z=450 for (M+H)$^+$. $^1$H NMR (360 MHz, CDCl$_3$) δ1.54–1.90 (8H, m), 1.95–2.02 (2H, m), 3.26–3.40 (2H, m), 3.43 (3H, s), 3.52–3.62 (2H, m), 5.28 (1H, d, J=8 Hz), 6.62–6.67 (2H, m), 6.98 (1H, dd, J$_1$=1 Hz, J$_2$=8 Hz), 7.10–7.55 (7H, m). Found: C, 67.23; H, 6.12; N, 15.46. $C_{25}H_{28}FN_5O_2$ requires C, 66.80; H, 6.28; N, 15.58%.

EXAMPLE 36

(−)-N-[5-(3-Azabicyclo[3,2,2]nonan-3-yl)-2,3-dihydro-1-methyl-2-oxo-1H-1,4-benzodiazepin-3-yl]-N'-[3-fluorophenyl]urea Hydrochloride The racemic compound (Example 35, 320 mg) was separated into its enantiomers using semi-preparative HPLC on a Pirkle dinitrobenzoylleucine column (5µ) [(250×21.4)mm] eluting with 5% methanol in 1-chlorobutane (including 1% acetic acid).

The free base was liberated and obtained as a colourless solid (140 mg). The hydrochloride salt had mp 208°–210° C. (acetone/ethyl acetate (1:1)). $[\alpha]^{24° C.}_D$=−235° (c=0.2, methanol). $^1$H NMR (360 MHz, D$_2$O) δ1.24–1.98 (9H, m), 2.28–2.36 (1H, m), 3.50 (3H, s), 3.61 (1H, d, J=15 Hz), 3.70 (1H, d, J=15 Hz), 3.76–3.84 (1H, m), 3.96–4.04 (1H, m), 5.58 (1H, s), 6.88 (1H, ddd, J$_1$=1 Hz, J$_2$=J$_3$=8 Hz), 7.07 (1H, d, J=8 Hz), 7.21 (1H, ddd, J$_1$=J$_2$=1 Hz, J$_3$=8 Hz), 7.33 (1H, ddd, J$_1$=J$_2$=J$_3$=8 Hz), 7.58 (1H, dd, J$_1$=J$_2$=8 Hz), 7.65 (1H, d, J=8 Hz), 7.75 (1H, d, J=8 Hz), 7.86 (1H, dd, J$_1$=J$_2$=8 Hz). Found: C, 60.84; H, 6.15; N, 13.32. $C_{25}H_{28}FN_5O_2 \cdot HCl \cdot 0.5CH_3O \cdot 0.5HH_2COCH_3$ requires C, 60.74; H, 6.35; N, 13.36%

EXAMPLE 37

(+)-N-[5-(3-Azabicyclo[3,2,2]nonan-3-yl)-2,3-dihydro-1-methyl-2-oxo-1H-1,4-benzodiazepin-3-yl]-N'-[3-fluorophenyl]urea Hydrochloride The title compound was obtained (115 mg) using the procedure described in Example 36. The hydrochloride salt had mp 207°–209° C. (acetone/ethyl acetate (1:1)). $[\alpha]^{24° C.}_D$=+240° (c=0.2, methanol). Found: C, 60.87; H, 6.23; N, 13.44. $C_{25}H_{28}FN_5O_2 \cdot HCl \cdot 0.5H_2O \cdot 0.5CH_3COCH_3$ requires C, 60.74; H, 6.35; N, 13.36%.

EXAMPLE 38

N-[3(R,S)-5-(3-Azabicyclo[3,2,1]octan-3-yl)-2,3-dihydro-1-methyl-2-oxo-1H-1,4-benzodiazepin-3-yl]-N'-[3-methyl phenyl]urea a) 5-(3-Azabicyclo[3,2,1]octan-3-yl)-1,3-dihydro-2H-1-methyl-3-oximido-1,4-benzodiazepin-2-one The title compound was obtained from 1-methyl-1,2,3,4-tetrahydro-3H-1,4-benzodiazepin-2,5-dione and 3-azabicyclo[3,2,1]octane (J. Pharm. Sci. 1968, 57, 1785–1787) as described in Example 4, steps c) and d). mp 249°–252° C. (ethyl acetate/diethyl ether). MS, CI$^+$, m/z=313 for (M+H)$^+$. Found: C, 62.28; H, 6.41; N, 16.54. $C_{17}H_{20}N_4O_2 \cdot H_2O$ requires C, 61.80; H, 6.71; N, 16.95%.

b) N-[3(R,S)-5-(3-Azabicyclo[3,2,1]octan-3-yl)-2,3-dihydro-1-methyl-2-oxo-1H-1,4-benzodiazepin-3-yl]-N'-[3-methylphenyl]urea The title compound was obtained (1.75 g) from the foregoing oxime as described in Example 31, Method A. mp 237°–239° C. MS, CI$^+$, m/z=432 for (M+H)$^+$. $^1$H NMR (360 MHz, CDCl$_3$) δ1.46–1.49 (6H, m), 1.90–2.24 (2H, m), 2.28 (3H, s), 2.74–2.82 (1H, m), 3.06–3.12 (1H, m), 3.40–3.50 (2H, m), 3.42 (3H, s), 5.35 (1H, d, J=8 Hz), 6.66–6.78 (1H, m), 6.81 (1H, d, J=8 Hz), 7.06–7.58 (8H, m). Found: C, 69.38; H, 6.79; N, 15.92. $C_{25}H_{29}N_5O_2$ requires C, 69.58; H, 6.77; N, 16.23%.

EXAMPLE 39

(−)-N-[5-(3-Azabicyclo[3,2,1]octan-3-yl)-2,3-dihydro-1-methyl-2-oxo-1H-1,4-benzodiazepin-3-yl]-N'-[3-methyl phenyl]urea Hydrochloride The rifle compound free base was obtained (580 mg) from the racemate (Example 38, 1.4 g) using the procedure described in Example 36. The hydrochloride salt had mp 218°–220° C. (acetone/ethyl acetate (1:1)). $[\alpha]^{23° C.}_D$=−215.5° (c=0.2, methanol). MS, CI$^+$, m/z=432 for (M+H)$^+$.

Found: C, 62.90; H, 6.46; N, 14.59. $C_{25}H_{29}N_5O_2$·HCl·0.5H$_2$O requires C, 62.95; H, 6.55; N, 14.68%.

EXAMPLE 40

(+)-N-[5-(3-Azabicyclo[3,2,1]octan-3-yl)-2,3-dihydro-1-methyl-2-oxo-1H-1,4-benzodiazepin-3-yl]-N'-[3-methyl phenyl]urea Hydrochloride The title compound free base was obtained (610 mg) from the racemate (Example 38, 1.4 g) using the procedure described in Example 36. The hydrochloride salt had mp 190° C. (dec.) MS, CI$^+$, m/z=432 for (M+H)$^+$. $[\alpha]^{23°\ C}_D$=+182° (c=0.2, methanol). Found: C, 62.77; H, 6.66; N, 14.07. $C_{25}H_{29}N_5O_2$·HCl·0.6H$_2$ 0.0.1CH$_3$CO$_2$CH$_2$CH$_3$ requires C, 62.56; H, 6.61; N, 14.36%.

EXAMPLE 41

(−)-N-[5-(3-Azabicyclo[3,2,2]nonan-3-yl)-2,3-dihydro-1-methyl-2-oxo-1H-1,4-benzodiazepin-3-yl ]-N'-[5-indanyl] urea a) α-amino-N-(5-(3-azabicyclo[3,2,2]nonan-3-yl)-2,3-dihydro-1-methyl-2-oxo-1H-1,4-benzodiazepin-3-yl) benzenepropanamide To a stirred solution of 3(R,S)-amino-5-(3-azabicyclo [3.2.2]nonan-3-yl)-1,3-dihydro-1-methyl-2H-1,4-benzodiazepin-2-one (2.22 g) in anhydrous dimethylformamide (25 ml) were added BOC-D-phenylalanine (2.07 g), 1-hydroxybenzotriazole (1.02 g), 1-(3-dimethylaminopropyl)-3-ethylcarbodiimide hydrochloride (1.49 g) and triethylamine (5 ml). After stirring at room temperature for 30 mintues, the reaction mixtures was left standing at 4° C. for 16 hours. The solvent was evaporated and the residue partitioned between ethyl acetate and 10% potassium carbonate solution. The organic layer was dried (sodium sulphate), evaporated to dryness, and the resulting oil purified by column chromatography on silica using dichloromethane-methanol/dichloromethane (1:99 ). The product obtained (2.7 g) was treated at 4° C. with ethyl acetate (15 ml), saturated with hydrogen chloride gas and stirred at room temperature for 40 minutes. The solution was cooled down to 4° C. and basified with saturated potassium hydrogen carbonate solution, the organic layer was separated and the aqueous re-extracted with ethyl acetate (30 ml). The combined organics were dried (sodium sulphate) and evaporated to dryness. The resulting oil was purified by column chromatography on silica using dichloromethane to ammonia/methanol/dichloromethane (0.2: 2:98) (gradient elution) to afford diastereomer A (0.38 g) HPLC (Spherisorb ODS2 column, 70% acetonitrile/30% of 0.2% triethylamine in water, pH to 3 with orthophosphoric acid): R$_t$6.8 minutes, and diastereomer B (0.51 g, 23%), Rf 0.37 in methanol/dichloromethane (1:9) on silica plates, HPLC (same conditions as in diastereomer A): R$_t$8.4 minutes.

b) (−)-3-Amino-5-(3-Azabicyclo[3,2,2]nonan-3-yl)-1,3-dihydro-1-methyl-2H-benzodiazepin-2-one Trifluoroacetate Phenyl isothiocyanate (120 μl) was added to a stirred solution of the foregoing diastereomeric amide A (380 mg) in anhydrous dichloromethane (10 ml) then heated at 40° C. (oil bath temperature) for 3 hours. The reaction mixture was evaporated and the residue purified by column chromatography on silica using dichloromethane methanol/dichloromethane (5:95), to afford the thiourea (440 mg). Anhydrous trifluoroacetic acid (16.8 ml) was added to the solid thiourea (430 mg) and the solution stirred at room temperature for 50 minutes. The mixture was evaporated to dryness and the yellow oil azeotroped with toluene. The residue was partitioned between water and diethyl ether, then the aqueous was freeze dried and azeotroped with toluene to afford the homochiral amine trifluoroacetate (218 mg). Rf 0.30 in methanol/dichloromethane (1:9) on silica plates, $[\alpha]^{23°\ C}_D$= −20.5° (c=0.2,methanol).

c) (−)-N-[5-(3-Azabicyclo[3,2,2]nonan-3-yl)-2,3-dihydro-1-methyl-2-oxo-1H-1,4-benzodiazepin-3,yl]-N'-[5-indanyl]urea A stirred, cooled (0° C.) solution of 5-aminoindan (81 mg) in anhydrous tetrahydrofuran (15 ml) was treated with triphosgene (60.4 mg) and triethylamine (250 μl). After stirring at 0° C. for 15 minutes a solution of (−)-3-amino-5-(3-azabicyclo[3.2.2]nonan-3-yl)-1,3-dihydro-1-methyl-2H-benzodiazepin-2-one trifluoroacetate (218 mg) in anhydrous tetrahydrofuran (15 ml) was added. After stirring at 0° C. for 10 minutes the reaction mixture was left standing at 4° C. for 2 days. The reaction mixture was evaporated to dryness and the residue partitioned between saturated potassium carbonate solution and ethyl acetate. The organic layer was dried (sodium sulphate) then evaporated and the residue purified by column chromatography on silica using dichloromethane 2% methanol in dichloromethane (gradient elution). The title compound was obtained as a colourless solid (145 mg, 60%). mp 256° C. $[\alpha]^{22°\ C}_D$=−124° (c=0.1, methanol). $^1$H NMR (360 MHz, DMSO-d$_6$) δ1.5–1.66 (6H, m), 1.76–1.87 (2H, m), 1.9–2.04 (4H, m), 2.76 (4H, dd, J$_1$=J$_2$=6.5 Hz), 3.23–3.36 (2H, m), 3.32 (3H, s), 3.6–3.7 (2H, m), 4.96 (1H, d, J=7 Hz), 6.79 (1H, d, J=7 Hz), 7.0–7.64 (7H, m), 8.78 (1H, s). Found: C, 71.59; H, 6.82; N, 14.73. $C_{28}H_{33}N_5O_2$ requires C, 71.31; H, 7.05; N, 14.85%.

EXAMPLE 42

N-[3(R,S)-5-(3-Azabicyclo[3,2,2]nonan-3-yl)-2,3-dihydro-1-methyl-2-oxo-1H-1,4-benzodiazepin-3-yl]-N'-[3-trifluoromethyl-phenyl]urea The title compound was obtained (690 mg) from 3(R,S)-amino-5-(3-azabicyclo[3,2,2]nonan-3-yl)-1,3-dihydro-1-methyl-2H-1,4-benzodiazepin-2-one and 3-trifluoromethylphenyl isocyanate as described in Example 31, Method A. mp 152°–154° C. (dichloromethane/diethyl ether (2:1)). MS, CI$^+$, m/z=500 for (M+H)$^+$. Found: C, 60,58; H, 5.96; N, 12.91. $C_{26}H_{28}F_3N_5O_2$·H$_2$O requires C, 60.34; H, 5.84; N, 13.50%.

EXAMPLE 43

N-[3(R,S)-2,3-Dihydro-5-(8-methyl-3,8-diazabicyclo[3,2,1]octan-3-yl)-2-oxo-1-propyl-1H-1,4-benzodiazepin-3-yl]-N'-[3-methylphenyl]urea Prepared analogously to Example 32 from 1-propyl-1,2,3,4-tetrahydro-3H-1,4-benzodiazepin-2,5-dione and 8-methyl-3,8-diazabicyclo[3,2,1]octane (J. Med. Chem. 1974, 17, 481–487). mp 247°–250° C. MS, CI$^+$, m/z=474 (M+H)$^+$. $^1$H NMR (360 MHz, DMSOd$_6$) δ0.70 (3H, t, J=7 Hz), 1.24 (1H, m), 1.39 (1H, m), 1.57 (1H, m), 1.79 (1H, m), 1.92 (1H, m), 2.15 (3H, s), 2.21 (3H, s), 2.62 (1H, m), 3.0 (4H, m), 3.62 (1H, m), 4,42 (1H, m), 4.93 (1H, d, J=8 Hz), 6.71 (1H, d, J=7 Hz), 6.98 (1H, d, J=8 Hz), 7.06 (3H, m), 7.59 (4H, m), 9.80 (1H, s). Found: C, 67.99; H, 6.95; N, 17.54. $C_{27}H_{34}N_6O_2$ requires C, 67.68; H, 7.26; N, 17.19%.

EXAMPLE 44

N-(3(R,S)-5-(3-Azabicyclo[3,2,2]nonan-3-yl)-2,3 -dihydro-1-methyl-2-oxo 1H-1,4-benzodiazepin-3-yl]-N'-[3-fluoro-4-methylphenyl]urea Prepared as described in Example 31, Method B. mp 254–255° C. Found: C, 65.87; H, 6.36; N, 14.54. $C_{26}H_{30}FN_5O_2.0.5H_2O$ requires C, 66.08; H, 6.61; N, 14.82%.

EXAMPLE 45

(−)-N-[5-(3-Azabicyclo[3,2,2]nonan-3-yl)-2,3-dihydro-1-methyl-2-oxo-1H-1,4-benzodiazepin-3-yl]-N'-[3-fluoro-4-methylphenyl]urea Hydrochloride The racemic compound (Example 44, 1.5 g) was separated into its enantiomers using semi-preparative HPLC on a Pirkle dinitrobenzoylleucine column (5μ) [(250×21.4)mm] eluting with 3% methanol in 1-chlorobutane (including 1% acetic acid). 20 ml/minute, λ=305 nm.

The fractions from peak A were evaporated to dryness and the free base liberated and obtained as a colourless foam (660 mg). The hydrochloride salt had mp 235°–236° C. (acetone/ethyl acetate). $[\alpha]^{23°\ C.}_D = -242°$ (c=0.2, methanol). $^1$H NMR (360 MHz, DMSOd$_6$) δ1.50–1.80 (10H, m), 2.12 (3H, d, J=2 Hz), 3.10–3.38 (1H, m), 3.41 (3H, s), 3.44–3.58 (2H, m), 3.70–4.00 (1H, m), 5.28–5.36 (1H, broad d), 6.90–7.86 (8H, m), 9.46 (1H, broad s). Found: C, 61.65; H, 6.20; N, 13.49. $C_{26}H_{30}FN_5O_2.HCl.0.5H_2O$ requires C, 61.35; H, 6.33; N, 13.75%.

EXAMPLE 46

(+)-N-[5-(3-Azabicyclo[3,2,2]nonan-3-yl)-2,3-dihydro-1-methyl-2-oxo-1H-1,4-benzodiazepin-3-yl]-N'-[3-fluoro-4-methylphenyl]urea Hydrochloride The title compound was obtained using the procedure described in Example 45. The fractions from peak B were evaporated to dryness and the free base liberated and obtained as a colourless foam (560 mg). The hydrochloride salt had mp 232°–234° C. (acetone/ethyl acetate). $[\alpha]^{23°\ C.}_D = +275°$ (c=0.2, methanol). Found: C, 61.54; H, 6.30; N, 13.23. $C_{26}H_{30}FN_5O_2.HCl.0.5H_2O.0.1CH_3CO_2CH_2CH_3$ requires C, 61.23; H, 6.38; N, 15.52%.

EXAMPLE 47

N-[3(R,S)-5-(3-Azabicyclo[3,2,2]nonan-3-yl)-2,3-dihydro-1-methyl-2-oxo-1H-1,4-benzodiazepin-3-yl]-N'-[3-iodophenyl]urea The title compound was obtained from 3(R,S)-amino-5-(3-azabicyclo[3,2,2]nonan-3-yl)-1,3-dihydro-1-methyl-2H-1,4-benzodiazepin-2-one (Example 31, Method B) and m-iodoaniline as described in Example 41. mp>176° C. (chloroform). MS, CI$^+$, m/z=558 for (M+H)$^+$. Found: C, 52.02; H, 5.00; N, 11.86. $C_{25}H_{28}IN_5O_2.H_2O$ requires C, 52.18; H, 5.25; N, 12.17%.

EXAMPLE 48

(−)-N-[5-(3-Azabicyclo[3,2,2]nonan-3-yl)-2,3-dihydro-1-methyl-2-oxo-1H-1,4-benzodiazepin-3-yl]-N'-[3-iodophenyl]urea The racemic compound was separated into its enantiomers using semi-preparative HPLC on a Pirkle dinitrobenzoylleucine column (5μ) [(250×21.4)mm] eluting with 4% methanol in 1-chlorobutane (including 1% acetic acid). 20 ml/minute, λ=305 nm.

The free base was liberated then recrystallised from ethyl acetate to afford a colourless solid (600 mg). mp 219°–221° C. $[\alpha]^{23°\ C.}_D = -132°$ (c=0.2, methanol). Found: C, 54.23; H, 5.03; N, 12.54. $C_{25}H_{28}IN_5O_2$ requires C, 53.87; H, 5.06; N, 12.56%.

EXAMPLE 49

(+)-N-[5-(3-Azabicyclo[3,2,2]nonan-3-yl)-2,3-dihydro-1-methyl-2-oxo-1H-1,4-benzodiazepin-3-yl]-N'-[3-iodophenyl]urea The title compound was obtained using the procedure described in Example 48. mp 220°–222° C. $[\alpha]^{23°\ C.}_D = +132°$ (c=0.2, methanol). Found: C, 54.31; H, 4.99; N, 12.28. $C_{25}H_{28}IN_5O_2$ requires C, 53.87; H, 5.06; N, 12.56%.

EXAMPLE 50

N-[3(R,S)-5-(3-Azabicyclo[3,2,2]nonan-3-yl)-2,3-dihydro-1-methyl-2-oxo-1H-1,4-benzodiazepin-3-yl]-N'-[phenyl]urea The title compound was prepared using the procedure described in Example 31 but replacing m-tolylisocyanate with phenyl isocyanate. mp 214°–215° C. (tetrahydrofuran). MS, CI$^+$, m/z=432 for (M+H)$^+$. Found: C, 69.78; H, 7.29; N, 14.62. $C_{25}H_{29}N_5O_2.0.5\ C_4H_8O$ requires C, 69.35; H, 7.11; N, 14.98%.

EXAMPLE 51

N-[3(R,S)-5-(2-Azabicyclo[2,2,2]octan-2-yl)-2,3-dihydro-1-methyl-2-oxo-1H-1,4-benzodiazepin-3-yl]-N'-[methylphenyl]urea a) 2-Azabicyclo[2,2,2]octane.

Anhydrous diethyl ether (150 ml) was added to a stirred solution of 1M lithium album hydride in diethyl ether (57 ml). Powdered 3-isoquinuclidinone (9 g, *Organic Synthesis*, Coll. Vol. V, 670 ) was added in portions over 15 minutes then the reaction mixture was heated at reflux for 5 hours. The mixture was cooled, quenched with saturated sodium chloride solution (5 ml) then stirred for 30 minutes. Diethyl ether (150 ml) was added then the reaction mixture was filtered, dried (potassium carbonate), evaporated to approximately 10 ml volume then treated with n-hexane (20 ml) and aged at −20° C. for 1 hour. 2-Azabicyclo[2,2,2]octane was isolated (4.80 g) as a colourless solid, mp 175°–180° C. $^1$H NMR (360MHz, CDCl$_3$) δ1.50–1.95 (9H, m), 2.84 (1H, s), 3.00 (2H, s), 3.38 (1H, broad s).

b) 5-(2-Azabicyclo[2,2,2]octan-2-yl)-1,3-dihydro-2H-1-methyl-1,4-benzodiazepin-2-one The title compound was prepared from 1-methyl-1,2,3,4-tetrahydro-3H-1,4-benzodiazepin-2,5-dione and 2-azabicyclo[2,2,2]octane as described in Example 31. mp 140°–142° C. (diethyl ether/n-hexane). MS, CI$^+$, m/z=284 for (M+H)$^+$. Found: C, 70.62; H, 7.27; N, 14.41. $C_{17}H_{21}N_3O.0.25H_2O$ requires C, 70.93; H, 7.53; N, 14.60%.

c) 5-(2-Azabicyclo[2,2,2]octan-2-yl)-1,3-dihydro-2H-1-methyl-3-oximido-1,4-benzodiazepin-2-one The title compound was obtained from the foregoing benzodiazepine as described in Example 31. mp 264°–266° C. MS, CI$^+$, m/z=313 for (M+H)$^+$. Found: C, 63.68; H, 6.44; N, 17.01. $C_{17}H_{20}N_4O_2.0.5H_2O$ requires C, 63.53; H, 6.59; N, 17.43%.

d) N-[3(R,S)-5-(2-Azabicyclo[2,2,2]octan-2-yl)-2,3-dihydro-1-methyl-2-oxo-1H-1,4-benzodiazepin-3-yl]-N'-[3-methylphenyl]urea The title compound was prepared from the foregoing oxime as described in Example 31, Method B. mp 242°–243° C. (dec) (ethyl acetate). MS, CI$^+$, m/z=432 for (M+H)$^+$. Found: C, 69.95; H, 6.77; N, 16.25. $C_{25}H_{29}N_5O_2$ requires C, 69.58; H, 6.77; N, 16.23%.

EXAMPLE 52

N-[3(R,S)-5-(3-Azabicyclo[3,2,2]nonan-3-yl)-2,3-dihydro-1-methyl-2-oxo-1H-1,4-benzodiazepin-3-yl)-N'-[4-fluoro-3-methylphenyl]urea A stirred, cooled (4° C.) solution of 3(R,S)-amino-5-(3-azabicyclo[3,2,2]nonan-3-yl)-1,3-dihydro-1-methyl-2H-1,4-benzodiazepin-2-one (1.20 g) in anhydrous tetrahydrofuran (15ml) was treated with triphosgene (388 mg) and triethylamine (1.6 ml). After 10 minutes 4-fluoro-3-methylaniline (576 mg) was added. The cooling bath was removed and the reaction mixture was stirred at room temperature for 4 hours then evaporated to dryness. The residue was partitioned between chloroform (50 ml) and water (50 ml). The organic layer was separated, washed with water (30 ml), dried (potassium carbonate) then evaporated to dryness. The solid obtained was recrystallised from hot ethyl acetate to afford the title compound (1.10 g, 63%). mp 160°–162° C. $^1$H NMR (360 MHz, CDCl$_3$) $\delta$1.56–1.90 (8H, m), 1.94–2.02 (2H, m), 2.19 (3H, d, J=2 Hz), 3.24–3.40 (2H, m), 3.41 (3H, s), 3.50–3.60 (2H, m), 5.28 (1H, d, J=8 Hz), 6.57 (1H, d, J=8 Hz), 6.85 (1H, dd, J$_1$=J$_2$=9 Hz), 7.00–7.05 (1H, m), 7.17 (1H, s), 7.21–7.32 (3H, m), 7.47–7.54 (2H, m). Found: C, 65.27; H, 6.58; N, 14.45. C$_{26}$H$_{30}$FN$_5$O$_2$.0.75H$_2$O requires C, 65.46; H, 6.66; N, 14.68%.

EXAMPLE 53

(−)-N-[5-(3-Azabicyclo[3,2,2]nonan-3-yl)-2,3-dihydro-1-methyl-2-oxo-1H-1,4-benzodiazepin-3-yl]-N'-[4-fluoro-3-methylphenyl]urea Hydrochloride The racemic compound (Example 52, 620 mg) was separated into its enantiomers using semi-preparative HPLC on a Pirkle dinitrobenzoylleucine column (5µ) [(250×21.4)mm] eluting with 5% methanol in 1-chlorobutane (including 1% acetic acid). 20 ml/minute, λ=305 nm.

The fractions from peak A were evaporated to dryness and the free base liberated (255 mg). The hydrochloride salt had mp 221°–223° C. (acetonitrile/ethyl acetate). [α]$^{23°}$ $^C$$_D$=−248° (c=0.2, methanol). MS, CI$^+$, m/z =464 for (M+H)$^+$ of free base. Found: C, 61.41; H, 6.22; N, 13.46. C$_{26}$H$_{30}$FN$_5$O$_2$.HCl1.0.5H$_2$O requires C, 61.35; H, 6.34; N, 13.76%.

EXAMPLE 54

(+)-N-[5-(3-Azabicyclo[3,2,2]nonan-3-yl)-2,3-dihydro-1-methyl-2-oxo-1H-1,4-benzodiazepin-3-yl]-N'-[4-fluoro-3-methylphenyl]urea Hydrochloride Obtained using the procedure described in Example 53. mp 221°–223° C. (acetonitrile/ethyl acetate). [α]$^{23°}$ $^C$$_D$=+240° (c=0.2, methanol). Found: C, 61.73; H, 6.20; N, 13.60. C$_{26}$H$_{30}$FN$_5$O$_2$.HCl.0.5H$_2$O requires C, 61.35; H, 6.34; N, 13.76%.

EXAMPLE 55

(−)-N-[5-(3-Azabicyclo[3,2,2]nonan-3-yl)-2,3-dihydro-1-methyl]-2-oxo-1H-1,4-benzodiazepin-3-yl]-N'-[3-trifluoromethylphenyl]urea Hydrochloride The racemic compound (Example 42, 400 mg) was separated into its enantiomers as described in Example 53. mp 215°–217° C. (acetonitrile/ethyl acetate). [α]$^{23°}$ $^C$$_D$=−216° (c=0.2, methanol). MS, CI$^+$, m/z=500 for (M+H)$^+$ of free base. Found: C, 57.76; H, 5.18; N, 12.79. C$_{26}$H$_{28}$F$_3$N$_5$O$_2$.HCl .0.25H$_2$O requires C, 57.78; H, 5.50; N, 12.96%.

EXAMPLE 56

(+)-N-[5-(3-Azabicyclo[3,2,2]nonan-3-yl)-2,3-dihydro-1-methyl-2-oxo-1H-1,4-benzodiazepin-3-yl]-N'-[3-trifluoromethylphenyl]urea Hydrochloride Obtained using the procedure described in Example 53. mp 209°–212° C. (acetonitrile/ethyl acetate). [α]$^{23°}$ $^C$$_D$=+212° (c=0.2, methanol). Found: C, 53.25; H, 5.32; N, 11.86. C$_{25}$H$_{28}$F$_3$N$_5$O$_2$.HCl.3H$_2$O requires C, 52.93; H, 5.88; N, 11.87%.

EXAMPLE 57

N-[3(R,S)-2,3-Dihydro-1-methyl-5-(cis-octahydroisoindol-2-yl)-2-oxo-1H-1,4-benzodiazepin-3-yl]-N'-[3-methylphenyl]urea a) Cis-Octahydroisoindole Cis-4-cyclohexene-1,2-dicarboximide (10.9 g) was hydrogenated over 10% palladium on carbon (1 g) in absolute ethanol (420 ml) at 50 psi for 10 minutes. The mixture was filtered then evaporated to give cis-cyclohexane-1,2-dicarboximide (10.6 g). To anhydrous diethyl ether (200 ml) was cannulated under nitrogen a 1M diethyl ether solution (200 ml) of lithium aluminium hydride. To the foregoing solution, under reflux, was added cis-cyclohexane-1,2-dicarboximide (10.6 g) portionwise over 10 minutes. The reaction mixture was heated to reflux for 3 hours. After cooling to 0° C., water (7 ml) was added followed by 4N sodium hydroxide (7.6 ml) and water (23 ml). The white suspension was stirred whilst warming to room temperature. The solid was removed by filtration then the filtrate dried (sodium sulphate) and evaporated to give a cream oil.

b) 1,3-Dihydro-1-methyl-5-(cis-octahydroisoindol-2-yl)-2H-1,4-benzodiazepin-2-one A solution of phosphorus pentachloride (6.15 g) in dichloromethane (250 ml) was added dropwise over 30 minutes to a stirred solution of 1-methyl-1,2,3,4-tetrahydro-3H-1,4-benzodiazepin-2,5-dione (4.56 g) in dichloromethane (150 ml). The solution was stirred at room temperature for 2 hours, the solvent evaporated in vacuo and the residue azeotroped with toluene. The dark solid was re-dissolved in dichloromethane (200 ml), cooled to 4° C. and a solution of crude cis-octahydroisoindole (3 g) and triethylamine (6.6 ml) in dichloromethane (100 ml) was added over 30 minutes. The cooling bath was removed and the reaction mixture was stirred for 2 hours, then washed sequentially with 10% potassium carbonate and brine (twice). The organic layer was separated, treated with potassium carbonate, silica (Kieselgel) and decolourizing charcoal. The mixture was filtered then evaporated to dryness and purified by column chromatography on silica using dichloromethane→10% methanol/dichloromethane (containing 1% ammonia) to afford the title compound (3.3 g). mp>128° C. (dec.). $^1$H NMR (360 MHz, CDCl$_3$) $\delta$1.16–1.72 (8H, m), 2.04–2.18 (1H, m), 2.3–2.43 (1H, m), 2.9–3.2 (2H, m), 3.36 (3H, s), 3.54 (1H, d, J=12 Hz), 3.5–3.76 (2H, m), 4.23 (1H, d, J=12 Hz), 7.19–7.32 (2H, m), 7.44–7.52 (2H, m).

c) 1,3-Dihydro-1-methyl-5-(cis-octahydroisoindol-2-yl)-2H-3-oximido-1,4-benzodiazepin-2-one Potassium t-butoxide (2.94 g) was added in portions to a stirred, cooled (−25° C.) solution of 1,3-dihydro-1-methyl-5-(cis-octahydroisoindol-2-yl)-2H-1,4-benzodiazepin-2-one (3.2 g) in anhydrous toluene (110 ml) under a nitrogen atmosphere. After stirring at −25° C. for 50 minutes isopentylnitrite (1.6 ml) was added. The reaction minute was stirred at −25° C. for 6 hours, then isopentylnitrite (0.8 ml) was added followed sequentially by potassium t-butoxide (300 mg) after 18 hours, isopentylnitrite (0.4 ml) afar a further 30 minutes and finally isopentylnitrite (1.6 ml) after a further 5 hours. The mixture was then stirred at −25° C. overnight. Whilst warming to room temperature the reaction mixture was treated with water (30 ml) containing citric acid (2,3 g) and diethyl ether (40 ml) then stirred for 1 hour. The precipitate was collected to afford the oxime (2.3 g). mp 236°–238° C. $^1$H NMR (360 MHz, CDCl$_3$) δ1.08–1.84 (8H, m), 2.12–2.56 (2H, m), 3.0–4.0 (4H, m), 3.41 and 3.45 (3H, each s), 7.18–7.64 (4H, m).

d) 1,3-Dihydro-1-methyl-5-(cis-octahydroisoindol-2-yl)-2H-3-(O-(ethylaminocarbonyl)oximido)-1,4-benzodiazepin-2-one The foregoing oxime (2.3 g), ethylisocyanate (2.8 ml) and triethylamine (1 ml) were heated at 65° C. in anhydrous tetrahydrofuran (150 ml) for 18 hours. The solvent was evaporated and the residue was purified by column chromatography on silica using dichloromethane→3% methanol/dichloromethane to afford a white foam (2.8 g, mixture of E/Z isomers). mp 175°–180° C. $^1$H NMR (360 MHz, CDCl$_3$) δ1.08–1.78 (8H, m), 1.13 (3H, t, J=7 Hz), 2.06–2.37 (2H, m), 2.90–3.12 (1H, m), 3.25 (2H, q, J=7 Hz), 3.44 and 3.45 (3H, each s), 3.53–3.80 (3H, m), 6.20–6.30 and 6.36–6.46 (1H, each m), 7.20–7.55 (4H, m).

e) 3(R,S)-Amino-1,3-dihydro-1-methyl-5-(cis-octahydroisoindol-2-yl)-2H-1,4-benzodiazepin-2-one The product of part a) (2.4 g) was hydrogenated at 45 psi in methanol (160 ml) over 10% palladium on carbon (1 g) for 3 hours at room temperature. The mixture was filtered then evaporated to dryness to afford the title amine (2 g).

f) N-[3(R,S)-2,3-Dihydro-1-methyl-5-(cis-octahydroisoindol-2-yl)-2-oxo-1H-1,4-benzodiazepin-3-yl]-N'-[3-methylphenyl]urea The foregoing amine (2 g) in anhydrous tetrahydrofuran (5 ml) was treated with m-tolylisocyanate (0.72 ml). After standing for 5 minutes 1 drop of dichloromethane was added. After ageing at 4° C. for 18 hours the precipitate was collected to afford the title compound as a free base (2.2 g). mp>156° C. (dec.). $^1$H NMR (360 MHz, DMSO) δ1.12–1.64 (8 H, m), 1.96–2.09 (1H, m), 2.21 (3H, s), 2.30–2.36 (1H, m), 2.74–3.1 (1H, m), 3.27–3.37 (1H, m), 3.31 (3H, s), 3.45–3.62 (2H, m), 4.94 (1H, d, J=8 Hz), 6.68–7.67 (8 H, m), 6.91 (1H, d, J=8 Hz), 8.79 (1H, s). Found: C, 65.40; H, 6.70; N, 14.83. C$_{26}$H$_{31}$N$_5$O$_2$.1.7H$_2$O requires C, 65.57; H, 7.28; N, 14.70%.

EXAMPLE 58

(−)-N-[2,3-Dihydro-1-methyl-5-(cis-octahydroisoindol-2-yl)-2-oxo-1H-1,4-benzodiazepin-3-yl]-N'-[3-methylphenyl] urea hydrochloride The racemic compound (Example 57, 1 g) was separated into its enantiomers using semi-preparative chiral HPLC on a Pirkle dinitrobenzoylleucine column (5μ) [(250×21.4)mm] eluting with ethanol/hexane (1:1), flow rate 20 ml/minute, U.V. detection at 310 mm.

The hydrochloride salt (350 mg) had mp>190° C. (dec.). MS, CI$^+$, m/z=446 for (M+H)$^+$. [α]$^{25\ C.}_D$=−107.5° (c=0.2, methanol). Found: C, 61.65; H, 6.96; N, 13.33. C$_{26}$H$_{31}$N$_5$O$_2$.HCl.1.5H$_2$O.0.1C$_4$H$_8$O requires C, 61.42; H, 6.99; N, 13.57%. HPLC (spherisorb ODS2, 70% acetonitrile/30% of 0.2% triethylamine in water and orthophosphoric acid to pH=3): 98.5% chemically pure.

EXAMPLE 59

(+)-N-[2,3-Dihydro-1-methyl-5-(cis-octahydroisoindol-2-yl)-2-oxo-1H-1,4-benzodiazepin-3-yl]N'[-3-methylphenyl] urea hydrochloride The title compound was obtained (360 mg) using the procedure described in Example 58. The hydrochloride salt had mp>190° C. (dec.). MS, CI$^+$, m/z=446 for (M+H)$^+$. [α]$^{25\ C.}_D$=109° (c=0.2, methanol). Found: C, 62.10; H, 7.02; N, 13.50. C$_{26}$H$_{31}$N$_5$O$_2$.HCl.1.2H$_2$O requires C, 62.00; H, 6.88; N, 13.90%. HPLC (spherisorb ODS2, 70% acetonitrile/30% of 0.2% triethylamine in water and orthophosphoric acid to pH=3):>99% chemically pure.

EXAMPLE 60

N-[3(R,S)-5-(N-Cyclohexyl-N-methylamino)-2,3-dihydro-2-oxo-1-propyl-1H-1,4-benzodiazepin-3-yl]-N'-[3-methylphenyl]urea a) 5-(N-Cyclohexyl-N-methylamino)-2-oxo-1-propyl-1,4-benzodiazepine Prepared analogously to Example 1a) from 1-propyl-1,2,3,4-tetrahydro-3H-1,4-benzodiazepin-2,5-dione (10.0 g) and N-methylcyclohexylamine (15.6 g) and purified by flash chromatography, eluted with 2% methanol/0.5% 0.88 ammonia solution/dichloromethane then 5% methanol/0.5% 0.88 ammonia solution/dichloromethane. $^1$H NMR (DMSO) δ0.68 (3H, t, J=7.3 Hz), 1.84–2.04 (3H, m), 2.72 (3H, s), 3.40 (1H, d, J=12.2 Hz), 3.54 (1H, m), 3.88 (1H, d, J=12.2 Hz), 4.22 (1H, m), 7.34 (1H, m), 7.50 (1H, d, J=7.43 Hz), 7.60 (2H, m)..

b) 5-(N-Cyclohexyl-N-methylamino)-3-oximino-2-oxo-1-propyl-1,4-benzodiazepine

Prepared analogously to Example 1b) from product from step (a) (5 g). The product was purified using flash silica chromatography, eluting with 0.5%. 0.88 ammonium solution/2% methanol/dichloromethane followed by chromatography on an alumina column, eluting with 2% methanol/dichloromethane followed by 5% methanol/dichloromethane. $^1$H NMR (DMSO) δ0.52–2.06 (16H, m), 2.60–2.92 (3H, m), 3.60 (1H, m), 4.26 (1H, m), 7.22–7.66 (14H, m), 9.84 and 10.02 (1H, 2×s).

c) N-[3(R,S)-5-(N-Cyclohexyl-N-methylamino)-2,3-dihydro-2-oxo-1-propyl-1H-1,4-benzodiazepin-3-yl]-N'-[3-methylphenyl]urea The product from step b) (2.31 g) was dissolved in acetic acid (40 ml), with activated zinc (8.83 g) and trifluoroacetic acid (5.2 ml). The reaction was heated at 40° C. for 8 h with vigorous stirring, then cooled to room temperature, filtered through hiflo, and washed through with acetic acid (2×20 ml). The solvent was removed in vacuo, the resulting oil was azeotroped with toluene and dried under high vacuum for 30 min to give a yellow foam. The foam was redissolved in tetrahydrofuran (50 ml), and triethylamine (1.0 ml) was added followed by m-tolylisocyanate (0.87 ml). The reaction was stirred at room temperature for 2 h then concentrated under vacuum. The residue was redissolved in dichloromethane (100 ml), washed with saturated sodium hydrogen carbonate solution (100 ml), separated and the aqueous phase was reextracted with dichloromethane (2×25 ml). The combined organic layers were washed with brine (50 ml), dried (sodium sulphate) and the solvent was removed in vacuo to give a solid which was purified by flash column chromatography with 0.5% 0.88 ammonia solution/dichloromethane as the eluant on a Lobar column. Mp=118° C. (uncorr); $^1$H NMR (DMSO) δ0.70 (3H, t, J=7.4 Hz), 0.90–1.90 (13H, m), 2.23 (3H, s), 2.68 (3H, s), 3.64 (1H, m), 4.26 (1H, m), 4.90 (1H, d, J=8.4 Hz), 6.71 (1H, d, J=8.0 Hz), 6.92 (1H, d, J=8.6 Hz), 7.12 (2H, m), 7.16 (1H, s), 7.38 (1H, m), 7.51 (1H, d, J=7.5 Hz), 7.64 (2H, m); MS (CI) m/e 462 [MH]$^+$. Anal. Found C, 66.38; H, 7.72; N, 14.07. C$_{27}$H$_{35}$N$_5$O$_2$.1.5H$_2$O requires C, 66.37; H, 7.84; N, 14.33%.

EXAMPLE 61

(−)-5-(N-Cyclohexyl-N-methylamino)-2,3-dihydro-2-oxo-1-propyl-1H-1,4-benzodiazepin-3-yl-N'[3-methylphenyl]urea The racemate (430 mg) of Example 60 was separated using preparative chiral HPLC with a dinitrobenzoyl leucine column (250×20 mm i.d. 5 μm) using 94:5:1 1-chlorobutane:methanol:acetic acid as the mobile phase (with a flow rate of 20 ml/min and UV detection at 330 nM). The two enantiomers were efficiently separated into Peak A (eluted first) and peak B (eluted second).

Peak A was evaporated in vacuo, and was partitioned between dichloromethane and sodium carbonate solution. The organic phases were dried ($MgSO_4$), evaporated in vacuo and the residue obtained was triturated with diethyl ether and the resulting solid was collected by filtration to give: Peak A (127 mg). Mp=121°–123° C.; $^1$H NMR (360 MHz, $D_6$-DMSO) δ0.69 (3H, t, J=7.4 Hz), 0.9–1.90 (13H, m), 2.21 (3H, s), 2.66 (3H, s), 3.64 (1H, m), 4.25 (1H, m), 4.89 (1H, d, J=8.4 Hz), 6.70 (1H, d, J=8.0 Hz), 6.94 (1H, d, J=7.5 Hz), 7.00 (2H, m), 7.16 (1H, s), 7.37 (1H, m), 7.50 (1H, d, J=7.5 Hz), 7.65 (2H, m), 8.80 (1H, s); MS (CI) m/e 462 [MH]$^+$. Anal. Found. C, 68.38; H, 7.74; N, 14.29. $C_{27}H_{35}N_5O_2$.0.85 $H_2O$ requires C, 68.00; H, 7.76; N, 14.69. $[α]^{22}_D$−114° (C=0.1, MeOH). Purity A:B=>99%.

EXAMPLE 62

(+) 5-(N-Cyclohexyl-N-methylamino)-2,3-dihydro-2-oxo-1-propyl-1H-1,4-benzodiazepin-3-y1-N'-[3-methylphenyl]urea Peak B from Example 61 was treated in the same way as Peak A Example 61. Mp=126°–127° C.; $^1$H NMR (360 MHz, $D_6$-DMSO) δ0.69 (3H, t, J=7.4 Hz), 0.9–1.90 (13H, m), 2.21 (3H, s), 2.66 (3H, s), 3.62 (1H, m), 4.25 (1H, m), 4.89 (1H, d, J=8,4 Hz), 6.70 (1H, d, J=8.0 Hz), 6.94 (1H, d, J=7.5 Hz), 7.00 (2H, m), 7.17 (1H, s), 7.38 (1H, m), 7.50 (1H, d, J=7.5 Hz), 7.65 (2H, m), 8.80 (1H, s); MS (CI) m/e 462 [MH]$^+$. Anal. Found. C, 69.93; H, 7.54; N, 14.62. $C_{27}H_{35}N_5O_2$.0.2 $H_2O$ requires C, 69.71; H, 7.67; N, 15.05%. $[α]^{22}_D$+108° (C=0.1, MeOH). Purity B:A=>96:4.

EXAMPLE 63

N-[3(R,S)-5-(N-Cyclohexyl-N-methylamino)-2,3-dihydro-1-methyl-2-oxo-1H-1,4-benzodiazepin-3-yl]-N'-[3-methylphenyl]urea Prepared as for Example 60 parts a, b, and c, from 1-methyl-1,2,3,4-tetrahydro-3H-1,4-benzodiazepin-2,5-dione and recrystallised from methanol, water. Mp 145°–147° C. $^1$H NMR (360 MHz, $D_6$-DMSO) δ0.99 (10H, m), 2.21 (3H, s), 2.65 (3H, s), 3.31 (4H, m), 4.92 (1H, d, J=8.4 Hz), 6.70 (1H, d, J=8.0 Hz), 6.93 (1H, d, J=7.5 Hz), 7.09 (2H, m), 7.17 (1H, s), 7.36 (1H, m), 7.49–7.69 (3H, m), 8.80 (1H, s); MS (CI) m/e 434 [MH]$^+$. Anal. Found. C, 67.22; H, 7.23; N, 15.29. $C_{25}H_{31}N_5O_2$.0.75$H_2O$ requires C, 67.17; H, 7.33; N, 15.67%.

EXAMPLE 64

(−)5-(N-Cyclohexyl-N-methylamine)-2,3-dihydro-2-oxo-1-methyl-1H-1,4-benzodiazepin-3-yl-N'-[3-methylphenyl]urea. Hydrochloride Separated from the racemate of Example 63 by chiral HPLC as for Example 61. Peak A free base was dissolved in dichloromethane. Ethereal hydrogen chloride was added and after 5 minutes the solvent was removed in vacuo. The resulting oil was crystallised from dichloromethane/ether. Mp 193°–195° C. $^1$H (360 MHz, $D_6$-DMSO, trifluoroacetic acid) δ0.95–1.95 (10H, m), 2.23 (3H, s), 3.12 (3H, s), 3.43 (4H, m), 5.39 (1H, m), 6.76 (1H, d, J=7.2 Hz), 7.11–7.90 (7H, m). MS (CI) m/e 434 [MH]$^+$. Anal. Found. C, 60.45; H, 7.02; N, 14.05. $C_{25}H_{31}N_5O_2$.HCl.1.5$H_2O$ requires C, 60.41; H, 7.02; N, 14.35%. $[α]^{22}_D$−195° (c=0.1, MeOH). Purity A:B=>99%.

EXAMPLE 65

(+)5-(N-Cyclohexyl-N-methylamino)-2,3-dihydro-2-oxo-1-methyl-1H-1,4-benzodiazepin-3-yl-N'[3-methylphenyl]urea. Hydrochloride Separated from the racemate of Example 63 by chiral HPLC as for Example 61. Peak B (eluted second) was treated as in Example 64 to yield the desired hydrochloride (90 mg). Mp 194°–196° C. $^1$H NMR (360 MHz, $D_6$-DMSO+trifluoroacetic acid) δ0.95–1.95 (10H, m), 2.24 (3H, s), 3.12 (3H, s), 3.43 (4H, m), 5.39 (1H, m), 6.76 (1H, d, J=7.5 Hz), 7.06–7.86 (7H, m), 9.20 (1H, s); MS (CI) m/e 434 [MH]$^+$. Anal. Found. C, 58.28; H, 6.82; N, .13.47. $C_{25}H_{31}N_5O_2$.HCl2.35$H_2O$ requires C, 58.61; H, 7.22; N, 13.67%. $[α]^{22}_D$+154° (C=0.1, MeOH). Purity B:A=>95%.

EXAMPLE 66

N-[3(R,S)-5-(N-Cycloheptyl-N-methylamino)-2,3-dihydro-1-methyl-2-oxo-1H-1,4-benzodiazepin-3-yl]-N'-[3-methylphenyl]urea Prepared analogously to Example 60 from N-methylcycloheptylamine. Mp=135° C. (uncorr); $^1$H NMR (DMSO) δ1.10 (1H, m), 1.20–1.50 (7H, m), 1.50–1.84 (4H, m), 1.91 (1H, m), 2.22 (3H, s), 2.63 (3H, s), 3.31 (3H, s), 4.94 (1H, d, J=8.0 Hz), 6.70 (1H, d, J=6.9 Hz), 6.94 (1H, d, J=8.4 Hz), 7.09 (2H, m), 7.17 (1H, s), 7.37 (1H, t, J=6.9 Hz), 7.51 (1H, dd, J=7.8 and 1.3 Hz), 7.62 (2H, m), 8.82 (1H, s); MS (CI) m/e 448 [MH]$^+$. Anal. Found. C, 70.02; H, 7.41; N, 15.60. $C_{26}H_{33}N_5O_2$ requires C, 69.77; H, 7.43; N, 15.65%.

EXAMPLE 67

(−)-5-(N-Cycloheptyl-N-methylamino)-2,3-dihydro-1-methyl-2-oxo-1H-1,4-benzodiazepin-3-yl-N'-[3-methylphenyl]urea, Hydrochloride a) The racemate (700 mg) of Example 66 was separated using preparative chiral HPLC with a dinitrobenzoylleucine column (250×20 mm i.d, 5 μM) using 89:10:1 1-chlorobutane:methanol:acetic acid as the mobile phase, with a flow rate of 20 ml/minute and u.v. detection of 330 nM.

Peak A was evaporated in vacuo and redissolved in the minimum of dichloromethane. The hydrochloride salt has formed by adding a saturated solution of hydrogen chloride in ether (5 ml). The resulting solution was triturated with ether, filtered and dried under high vacuum. Mp. 172°=174° C.; $^1$H NMR (360 MHz, $D_6$-DMSO, V.T. α353K) δ1.04–2.12 (13H, m), 2.24 (3H, s), 3.04 (3H, s), 3.38 (3H, s), 5.32 (1H, d, J=7.6 Hz), 6.72 (1H, d, J=7.6 Hz), 7.04–7.26 (4H, m) 7.52 (1H, t, J=7.6 Hz), 7.70 (2H, m), 7.82 (1H, t, J=7.3 Hz), 9.24 (1H, s(b)); MS (CI) m/e 448 [MH]$^+$. Anal. Found. C, 62.44; H, 7.29; N, 13.71, $C_{26}H_{33}N_5O_2$.HCl requires C, 62.20; H, 7.23; N, 13.95. $[α]^{22}_D$=−210° (c=1 mgm$^{-1}$, MeOH). Purity A:B>99%.

EXAMPLE 68

(+)-5-(N-Cycloheptyl-N-methylamino)-2,3-dihydro-1-methyl-2-oxo-1H-1,4-benzodiazepin-3-yl-N'-[3-methylphenyl]urea. Hydrochloride Peak B from Example 67 was treated in the same way as peak A to give the required product. Mp 173°–175° C.; $^1$H NMR (360 MHz, D$_6$-DMSO, V.T. α353K) δ1.06–2.14 (13H, m), 2.24 (3H, s), 3.05 (3H, s), 3.38 (3H, s), 5.33 (2H, d, J=7.6 Hz), 6.74 (1H, d, J=7.2 Hz) 7.04–7.26 (4H, m), 7.54 (1H, t, J=7.5 Hz), 7.63–7.74 (2H, m), 7.82 (1H, t, J=7.5 Hz), 9.25 (1H, s(b)); MS (CI) m/e 448 [MH]$^+$. Anal. Found. C, 62.36; H, 7.26; N, 13.53. C$_{26}$H$_{33}$N$_5$O$_2$.HCl requires C, 62.20; H, 7.23; N, 13.95. [α]$^{22}_D$=+172° (c=1 mgm/$^{-1}$, MeOH). Purity B:A=96.2%

EXAMPLE 69

N-[3(R,S)-5-(N-Cycloheptyl-N-methylamino)-2,3-dihydro-1-methyl-2-oxo-1H-1,4-benzodiazepin-3-yl]-N'-[5-indanyl] urea a) (±)-N-[3-amino-5-(N-cycloheptyl-N-methylamino-2,3-dihydro-1-methyl-2-oxo-1H-1,4-benzodiazepine. (TFA salt)

To a solution of 5-(N-cycloheptyl-N-methylamino)-1-methyl-3-oximino-2-oxo-1,4-benzodiazepine (1.00 g,) in acetic acid (40 ml) was added activated zinc (3.99 g) and trifluoroacetic acid (3.48 g). The reaction was stirred at 40° C. for 30 minutes, cooled to room temperature, filtered through hiflo, and washed with acetic acid (2×20 ml). The solvent was removed in vacuo, and the resulting oil was azeotroped with toluene and dried under high vacuum.

b) N-[3(R,S)-5-(N-Cycloheptyl-N-[methylamino)-2,3-dihydro-1-methyl-2-oxo-1H-1,4-benzodiazepin-3-yl]-N'-[5indanyl]urea 5-aminoindane (0,41 g) was dissolved in tetrahydrofuran (50 ml) and cooled (0° C.) under nitrogen. Triphosgene (0.31 g) was added and the reaction stirred vigorously (2 minutes). Triethylamine (0.92 g) was added and the reaction stirred for a further 30 minutes.

A solution of the product from part a) and triethylamine (sufficient to take solution to pH9) in tetrahydrofuran (25 ml) was added dropwise and the reaction allowed to stir overnight. The solvent was removed in vacuo, and the reaction mixture redissolved in dichloromethane (100 ml). This solution was washed with saturated sodium bicarbonate solution (50 ml), reextracted with dichloromethane (3×25 ml) and the combined organics washed with brine (50 ml). The solution was dried over sodium sulphate and the solvent removed in vacuo to give an oil that was purified by column chromatography with 0.2% 0.88 ammonia solution/dichloromethane then by 0.2% 0.88 ammonia solution/2% methanol/dichloromethane as the eluent. The product was recrystallised from ethyl acetate/60–80 petrol. Mp 183°–185° C. $^1$H NMR (360 MHz, D$_6$-DMSO, V.T. α353K) δ0.80–1.80 (11H, m), 1.86–2.04 (3H, m), 2.65 (3H, s), 2.74 (4H, q, J=7.0 Hz), 3.30 (3H, s), 3.59 (1H, m), 4.94 (1H, d, J=7.1 Hz), 6.74 (1H, d, J=8.4 Hz), 7.02 (2H, m), 7.22 (1H, s), 7.34 (1H, t, J=8.4 Hz), 7.48 (1H, m), 7.52 (1H, m), 7.60 (1H, m), 8.60 (1H, s). MS (CI) m/e 474 [MH]$^+$. Anal. Found. C, 71.69; H, 7.86; N, 14.14. C$_{28}$H$_{35}$N$_5$O$_2$.0.3C$_6$H$_4$ requires C, 71.66; N, 7.91; N, 14.02%

EXAMPLE 70

(−)-5-(N-Cycloheptyl-N-methylamino)-2,3-dihydro-1-methyl-2-oxo-1H-1,4-benzodiazepin-3-yl-N'-[5-indanyl]urea. Hydrochloride a) The racemate of Example 69 (600 mg) was separated using preparative chiral HPLC with a dinitrobenzoylleucine column (250×20 mm i.d, 5 μm) using 70% ethanol in hexane as eluent at a flow rate of 20 ml/min and u.v. detection at 330 nM.

Peak A was concentrated in vacuo and redissolved in dichloromethane (~2 ml). A saturated solution of hydrogen chloride in dry diethyl ether (5 ml) was added and the resulting suspension was triturated with more diethyl ether (20 ml). The product was collected by filtration. Mp 181°–187° C. dec; $^1$H NMR (360 Mhz, DMSO) δ1.20–2.12 (14H, m), 2.76 (4H, q, J=7.0 Hz), 2.93–3.12 (3H, 2s, CH$_3$ restricted rotation), 3.42 (3H, s), 3.62 and 4.18 (1H, 2m), 5.36 (1H, m), 7.05–7.90 (8H, m), 9.48–9.53 (1H, 2s). 10.17 and 10.32 (1H, 2br s); MS (CI) m/e 474 [MH]$^+$. Anal. Found C, 62.83; H, 7.19; N, 13.07. C$_{28}$H$_{35}$N$_5$O$_2$.HCl.1.5H$_2$O requires C, 62.61; H, 7.32; N, 13.04%. [α]$^{22}_D$−175° (c=0.1, MeOH). Purity A:B>99%.

EXAMPLE 71

(+)-[5-(N-Cycloheptyl-N-methylamino)-2,3-dihydro-1ethyl-2-oxo-1H-1,4-benzodiazepin-3-yl ]-N'-[5-indanyl ]urea Hydrochloride Prepared analogously to Example 70. m.p. 181°–187° C. dec; $^1$H NMR (360 MHz, DMSO) δ1.20–2.19 (14H, m), 2.76 (4H, q, J=7.0 Hz), 2.93 and 3.12 (3H, 2s, CH$_3$ restricted rotation), 3.42 (3H, s), 3.62 and 4.18 (1H, 2 m), 5.36 (1H, m). 7.05–7.90 (8H, m), 9.40 and 9.42 (1H, 2s), 10.10 and 10.26 (1H, 2br s); MS (CI) m/e 474 [MH]$^+$. Anal. Found C, 62.83; H, 7.20; N, 13.06. C$_{28}$H$_{35}$N$_{52}$.HCl.1.5H$_2$O requires C, 62.61; H, 7.32; N, 13.04%. α$^{22}_D$+197° (c=0.1, MeOH). Purity B:A>99%.

EXAMPLE 72

N-[3(R,S)-5-(N-Benzyl-N-methylamino)-2,3-dihydro-1-methyl-2-oxo-1H-1,4-benzodiazepin-3-yl]-N'-[3-methylphenyl]urea To a solution of 5-(N-benzyl-N-methylamino)-3-oximino-2-oxo-1-methyl-1,4-benzodiazepine (prepared as for Example 1 parts a and b, from 1-methyl-1,2,3,4-tetrahydro-3H-1,4-benzodiazepin-2,5-dione and N-methylbenzylamine) in methanol was added rhodium on carbon (600 mg) and the resultant mixture was hydrogenated at 50 psi at 60° C. for 5 h. The reaction mixture was allowed to cool, filtered and concentrated in vacuo. The residue was dissolved in tetrahydrofuran, cooled to 0° C. and m-tolylisocyanate added. This mixture was stirred at room temperature for 12 hours, solvent removed in vacuo and the residue purified by flash column chromatography with 0.5% 0.88 ammonia solution, methanol and dichloromethane as the eluent, to yield the product which was recrystallised from dichloromethane, ethyl acetate (1:1). Mp 172°–174° C. $^1$H NMR (360 MHz, D$_6$-DMSO) δ2.21 (3H, s), 2.74 (3H, s), 4.26 and 4.55 (2H, dd, J=15.8 Hz), 5.00 (1H, d, J=8.4 Hz), 6.70 (1H, d, J=8.0 Hz), 6.96–7.76 (12H, m), 8.81 (1H, s); MS (CI) m/e 442 (MH)$^+$. Anal. Found C, 70.86; H, 6.39; N, 15.85% C$_{26}$H$_{27}$N$_5$O$_2$ requires C, 70.73; H, 6.16; N, 15.86%.

EXAMPLE 73

N-[3(R,S)-5-(N-(4-N-Methylpiperidinyl)-N-methylamino)-2,3-dihydro-1-methyl-2-oxo-1H-1,4-benzodiazepin-3-yl]-N'-[3-methylphenyl]urea Prepared analogously to Example 60 from 1-methyl-1,2,3,4-tetrahydro-3H-1,4-benzodiazepin-2,5-dione and N-methyl-(4-methylamino)piperidine. Mp=146° C. (uncorr); $^1$H NMR (DMSO) δ1.24 (1H, m), 1.60–1.90 (6H, m), 2.12 (3H, s) 2.21 (3H, s), 2.65 (3H, s), 2.75 (1H, m), 2.82 (1H, m), 3.32 (all, s), 4.92 (1H, d, J=8.4 Hz), 6.70 (1H, d, J=7.1 Hz), 6.95 (1H, d, J=8.4 Hz), 7.09 (2H, m), 7.17 (1H, s), 7.38 (1H, m), 7.51 (1H, dd, J=1.4+7.8 Hz), 7.62 (2H, m), 8.82 (1H, s); MS (CI) m/e 449 [MH]⁺. Anal. Found: C, 63.37; H, 7.04; N, 17.46. $C_{25}H_{32}N_6O_2 \cdot 1.3H_2O$ requires C, 63.62; H, 7.39; N, 17.81%.

EXAMPLE 74

N-[3(R,S)-5-(N-Cyclohexylmethyl-N-methylamino)-2,3-dihydro-2-oxo-1-propyl-1H.1,4-benzodiazepin-3-yl]-N'-[3-methylphenyl]urea Prepared as described in Example 60 from N-methylcyclohexylamine and 1-methyl-1,2,3,4-tetrahydro-3H-1,4-benzodiazepin-2,5-dione; mp 218°–225° C. ¹H NMR (DMSO) δ0.31 (1H, m), 0.66 (1H, m), 0.96–1.54 (9H, m), 2.21 (3H, s), 2.81 (3H, s), 2.92 (1H, m), 3.16 (1H, m), 3.30 (3H, s), 4.94 (1H, d, J=8.4 Hz), 6.70 (1H, d, J=7.0 Hz), 6.91 (1H, d, J=8.4 Hz), 7.05–7.65 (7H, m), 8.81 (1H, s); MS (CI) m/e 448 [MH]⁺. Anal. Found C, 65.59; H, 7.44; N, 15.46. $C_{26}H_{33}N_5O_2$ requires C, 69.77; H, 7.47; N, 15.65%.

EXAMPLE 75

N-[3(R,S)-5-(N,N-Di-ⁿpropylamino)-2,3-dihydro-1-methyl-2-oxo-1H-1,4-benzodiazepin-3-yl]-N-[3-methyl phenyl]urea Prepared as for Example 60, using di-n-propylamine in place of N-methylcyclohexylamine and recrystallized from ethyl acetate and hexane. Mp 164°–166° C. ¹H NMR (360 MHz, D₆-DMSO-TFA) δ0.60 (3H, t, J=7.3 Hz), 0.99 (3H, t, J=7.4 Hz), 1.57 (2H, m), 1.73 (2H, m), 2.25 (3H, s), 3.43 (5H, m), 3.88 (2H, m), 5.40 (1H, d, J=6.3 Hz), 6.78 (1H, d, J=7.1 Hz), 7.35–7.70 (8H, m), 9.30 (1H, s) MS (CI) m/e 422 [MH]⁺. Anal. Found: C, 68.33; H, 7.44; N, 16.27%. $C_{24}H_{31}N_5O_2$ requires C, 68.38; H, 7.41; N, 16.61%.

EXAMPLE 76

N-[3(R,S)-5-(N-Cyclopentyl-N-ethylamino)-2,3-dihydro-1-methyl-2-oxo-1H-1,4-benzodiazepin-3-yl]-N'-[3-methylphenyl]urea Prepared as for Example 72, but using N-ethylcyclopentylamine in place of N-methylbenzylamine and recrystallized from ethyl acetate hexane. Mp=252°–255° C., ¹H NMR (360 MHz, D₆-DMSO) δ0.70–1.60 (11H, m), 2.21 (3H, s), 2.91–3.90 (6H, m), 5.37 (1H, d, J=8.4 Hz), 6.72 (1H, d, J=8.0 Hz), 6.92 (1H, d, J=7.5 Hz, 7.10 (2H, m), 7.29–7.63 (5H, m), 10.24 (1H, s). Anal. Found: C, 69.70; H, 7.21; N, 15.41%. $C_{25}H_{31}N_5O_2 \cdot 0.15C_6H_{14}$ requires C, 69.68; H, 7.47; N, 15.69%.

EXAMPLE 77

N-[3(R,S)-5-(N-(4,4-Dimethylcyclohexyl)-N-methylamino)-2,3-dihydro-1-methyl-2-oxo-1H-1,4-benzodiazepin yl-3yl]-N'-[3-methylphenyl]urea a) N-Methyl-4,4-dimethylcyclohexylamine To a solution of 4,4-dimethylcyclohexanone (25.2 g) in dry methanol under an atmosphere of nitrogen was added methylamine hydrochloride (13.2 g) and 3 Åmol sieves (1 g). The reaction mixture was stirred for 1 hr then sodium cyanoborohydride (12.7 g) added portionwise. The mixture was stirred for 17 hrs. A saturated solution of hydrogen chloride in methanol (200 ml) was added and the reaction mixture stirred for 1 hr the filtered through hyflo and concentrated in vacuo. The residue was partitioned between 1N sodium hydroxide (300 ml) and dichloromethane (200 ml). The layers were separated and the aqueous re-extracted with dichloromethane (2×200 ml). The combined organics were washed with saturated sodium hydrogen concentrated in vacuo. The residue was distilled under reduced pressure. Bpt 40°–45° C. at 0.1 mmHg. ¹H NMR (CDCl₃) δ0.92 (6H, s), 1.10–1.30 (5H, m), 1.30–1.50 (2H, m), 1.66–1.72 (2H, m), 2.26 (1H, m), 2.42 (3H, s).

b) 5-(N-(4,4-Dimethylcyclohexyl)-N-methylamino)-3-oximino-1-methyl-2-oxo-1,4-benzodiazepine Prepared as described in Example 1, stops a) and b) from 1-methyl-1,2,3,4-tetrahydro-3H-1,4-benzodiazepin-2,5-dione and N-methyl-4,4-dimethylcyclohexylamine.

c) N-[3(R,S)-5-(N-(4,4-Dimethylcyclohexyl)-N-methylamino)-2,3-dihydro-1-methyl-2-oxo-1H-1,4-benzodiazepin-3-yl]-N'-[3-methylphenyl]urea The product from stop b) (800 mg) was dissolved in dry tetrahydrofuran under an atmosphere of nitrogen and ethyl isocyanate (0.37 ml) added. The reaction mixture was heated at 60° C. for 12 h with stirring, then cooled to room temperature and concentrated in vacuo. The residue was purified by flash column chromatography on silica elution with 1→3% methanol/0.5% 0.88 ammonia solution in dichloromethane. The product was dissolved in methanol (20 ml) and palladium on activated charcoal (400 mg) was added. The reaction was hydrogenated at 40 psi for 2 hrs then filtered through a glass fibre filter and concentrated in vacuo without heating. The product was dissolved in dry tetrahydrofuran (2 ml) and m-tolylisocyanate (212 µl) added. After 20 mins diethyl ether (10 ml) was added and the product collected by filtration and recrystallised from ethyl acetate. mp=172° C. (uncorr). ¹H NMR (DMSO) δ0.82 (3H, s), 0.88 (3H, s), 0.90–1.20 (3H, m), 1.20–1.42 (2H, m), 1.56–2.84 (3H, m), 2.21 (3H, s), 2.69 (3H, s), 3.31 (3H, s), 4.92 (1H, d, J=8.4 Hz), 6.70 (1H, d, J=8.8 Hz), 6.94 (1H, d, J=8.4 Hz), 7.10 (2H, m), 7.17 (1H, s), 7.36 (1H, m), 7.50 (1H, dd, J=1.3 & 7.7 Hz), 7.60 (2H, m), 8.80 (1H, s); MS (CI) m/e 462 [MH]⁺. Anal. Found: C, 69.48; H, 7.69; N, 15.18. $C_{27}H_{35}N_5O_2 \cdot 0.2H_2O$ requires C, 69.71; H, 7.67; N, 15.05%.

EXAMPLE 78

N-[3(R,S)-5-(N-Cyclohexyl-N-ethylamino)-2,3-dihydro-1-methyl-2-oxo-1H-1,4-benzodiazepin-3-yl]-N'-3-methylphenyl]urea Prepared as for Example 60 using N-ethylcyclohexylamine in place of N-methylcyclohexylamine and recrystallized from ethyl acetate. Mp=206°–207° C. ¹H NMR (360 MHz, D₆-DMSO) δ0.83 (3H, m), 0.83–1.9 (10H, m), 2.2 (3H, s), 3.0 (1H, m), 3.3 (4H, m), 4.9 (1H, d, J=8.9 Hz), 6.7 (1H, d, J=6.5 Hz), 6.9–7.6 (8H, Aromatics), 8.8 (1H, s). MS (CI) m/e 448 (MH)⁺. Anal. Found: C, 69.79; H, 7.6; N, 14.82%. $C_{26}H_{33}N_5O_2$ requires C, 70.04; H, 7.49; N, 15.18%.

EXAMPLE 79

N-[3(R,S)-5-(N-Cyclohexyl-N-propylamino)-2,3-dihydro-1-methyl-2-oxo-1H-benzodiazepin-3-yl]-N'-[3-methylphenyl]urea Prepared as described in Example 60 from 1-methyl-1,2,3,4-tetrahydro-3H-1,4-benzodiazepin-1,5-dione and N-propylcyclohexylamine. Mp=146° C. (uncorr); ¹H NMR (360 MHz, DMSO) δ0.77 (3H, s), 0.86–1.18 (3H, m), 1.20–1.56 (6H, m), 1.56–1.80 (2H, m), 1.88 (1H, m), 2.12 (3H, s), 2.82 (1H, m), 3.31 (3H, s), 3.43 (1H, m), 4.93 (1H, d, J=8.3 Hz), 6.70 (1H, d, J=6.9 Hz), 6.89 (1H, d, J=8.3 Hz), 7.10 (2H, m), 7.18 (1H, s), 7.38 (1H, m), 7.48 (1H, dd, J=1.3 & 7.9 Hz), 7.61 (2H, m), 8.12 (1H, s); MS (CI) me 462 [MH]⁺.

EXAMPLE 80

N-[3(R,S)-5-(N-Benzyl-N-cyclohexylamino)-2,3-dihydro-1-methyl-2-oxo-1H-1,4-benzodiazepin-3-yl]-N'-[3-methylphenyl]urea a: N-Benzylcyclohexylamine To a stirred solution of cyclohexylamine (9.34 g) in methanol (300 ml) was added benzaldehyde (10.0 g) followed by activated 3 Å molecular sieves. After 1 h, sodium cyanoborohydride (7.13 g) was added followed by the dropwise addition of acetic acid (9.2 ml), and the reaction was stirred overnight. The reaction mixture was filtered through hiflo, the solvent removed in vacuo and the resulting white solid was heated under reflux in 5M potassium hydroxide solution for 30 mins. The product was extracted into dichloromethane (3×100 ml) and the combined organic layers were washed with brine (100 ml), dried over sodium sulphate and the solvent was removed in vacuo to give a clear oil. The product was purified by column chromatography (eluting with ethyl acetate) then distillation; bpt=137° C. at 1.0 mbarr. $^1$H NMR (360 MHz, $D_6$-DMSO) δ0.94–1.24 (5H, m), 1.48–1.88 (5H, m), 2.32 (1H, m), 2.32 (1H, m), 3.10 (2H, s(b)), 3.72 (2H, s), 7.14–7.40 (5H, m).

b) N-[3(R,S)-5-N-Benzyl-N-cyclohexylamino)-2,3-dihydro-1-methyl-2-oxo-1H-1,4-benzodiazepin-3-yl]-N'-[-3-methylphenyl]urea Prepared as for Example 60 from 1-methyl-1,2,3,4-tetrahydro-3H-1,4-benzodiazepin-2,5-dione and N-benzylcyclohexylamine and recrystallised from ethyl acetate/60–80 petrol. mp=178°–179° C., $^1$H NMR (360 MHz, $D_6$-DMSO, VT α353K) δ0.92–1.94 (10H, m), 2.21 (3H, s), 3.16 (3H, s), 3.66 (1H, m), 4.22 (1H, d, J=16 Hz), 4.70 (1H, d, J=16 Hz), 4.92 (1H, d, J=8.3 Hz), 6.72 (2H, m), 7.02–7.24 (8H, m), 7.32 (1H, m), 7.44 (1H, m), 7.56 (2H, m), 8.62 (1H, s); MS (CI) m/e=510 [MH]$^+$; Anal. Found: C, 73.08; H, 6.85; N, 13.74. $C_{31}H_{35}N_5O_2$ requires C, 73.06; H, 6.92; N, 13.74%.

EXAMPLE 81

N-[3(R,S)-5(N-Cyclohexylamino)-2,3-dihydro-1-methyl-2-oxo-1H-1,4-benzodiazepin-3-yl]-N'-[3-methylphenyl]urea To a stirred solution of the product of Example 80 (0.50 g) in methanol (40 ml) under nitrogen was added ammonium formate (0.31 g) followed by 10% palladium on carbon (0.50 g). The reaction mixture was heated under reflux for 2 h then cooled to room temperature, filtered, washed with methanol (3×20 ml) and the solvent removed in vacuo. The product was redissolved in dichloromethane (200 ml), washed with brine (100 ml), dried over sodium sulphate and the solvent removed in vacuo to give a white solid. Recrystallised from ethyl acetate/60–80 petrol. mp=153°–155° C.; $^1$H NMR (360 MHz, $D_6$-DMSO) δ0.88 (1H, m), 1.06–1.34 (4H, m), 1.88–2.00 (5H, m), 2.22 (3H, s), 3.28 (3H, s), 3.58 (1H, m), 4.88 (1H, d, J=8.6 Hz), 6.54 (1H, d, J=7.7 Hz), 6.68 (1H, d, J=6.9 Hz), 6.86 (HI, d, J=8.6 Hz), 7.08 (2H, m), 7.14 (1H, s), 7.34 (1H, t, J=7.8 Hz), 7.60 (2H, m), 8.77 (1H, s); MS (CI); m/e=420 [MH]$^+$. Anal. Found: C, 65.77; H, 6.97; N, 15.98. $C_{24}H_{29}H_5O_2.H_2O$ requires C, 65.77; H, 7.14; N, 16.01%.

EXAMPLE 82

N-[3(R,S)-5-(N-Cyclohexyl-N-methylamino)-2,3-dihydro-1-methyl-2-oxo-1H-1,4-benzodiazepin-3-yl]-N'-[5-indanyl]urea Prepared as for Example 77c) and Example 69b) using 5-aminoindane. Mp=232°–234° C. $^1$H NMR (360 MHz, $D_6$-DMSO) δ1.01–1.98 (16H, m), 2.65 (3H, m), 2.76 (H, m), 4.92 (H, d, J=8.46 Hz), 6.88 (H, d, J=8.46 Hz), 7.23–7.65 (7H, m), 8.65 (H, s). MS (CI) m/3 461 [MH$^+$]. Anal Found: C, 68.78; H, 7.34; N, 13.26%. $C_{27}H_{33}N_5O_2.0.7EtOAc.0.7H_2$) requires C, 68.48; H, 7.71; N, 13.39%.

EXAMPLE 83

N-[3(R,S)-5-(N-Cyclooctyl-N-methylamino)-2,3-dihydro-1-methyl-2-oxo-1H-1,4-benzodiazepin-3-yl]-N'-[3-methylphenyl]urea Prepared as for Example 77 using N-methyl cyclooctylamine in place of N-methyl-4,4-dimethylcyclohexylamine. mp=221°–222° C. $^1$H NMR (360 MHz, $D_6$-DMSO) δ1.1–1.6 (14H, m), 2.2 (3H, s), 2.66 (3H, s), 3.3 (3H, s), 4.96 (1H, d, J=1.18 Hz), 6.7 (1H, d, J=6.6 Hz), 6.9–7.6 (8H, m), 8.8 (1H, s).

EXAMPLE 84

N-[3(R,S)-2,3-Dihydro-5-(2-(N,N-dimethylamino)ethylamino)-1-methyl-2-oxo-1H-1,4-benzodiazepin-3-yl]-N'-[3-methylphenyl]urea dihydrochloride a) 1,2-Dihydro-5-(2-(N,N-dimethylamino)ethylamino)-1-methyl-3H-1,4-benzodiazepin-2-one A solution of phosphorous pentachloride (8.10 g) in anhydrous dichloromethane (350 ml) was added dropwise to a stirred suspension of 1-methyl-1,2,3,4-tetrahydro-3H-1,4-benzodiazepin-2,5-dione (6.0 g) in anhydrous dichloromethane (150 ml). After stirring for 3 h the solvent was evaporated, the residue re-dissolved in dichloromethane (200 ml), cooled to 4° C. and treated dropwise with a solution of N,N-dimethylaminoethylamine (8.8 g) in anhydrous dichloromethane (100 ml). The cooling bath was removed and the reaction mixture was stirred at room temperature for 2 h. The reaction mixture was evaporated to dryness and the residue purified by column chromatography on neutral alumina (Grade 3) using dichloromethane/methanol (30:1) to (20:1) (gradient elution). MS, CI$^+$, m/z=262 for (M+H)$^+$. $^1$H NMR (CDCl$_3$) δ2.24 (6H, s), 2.46–2.60 (2H, m), 3.36 (s) and 3.32–3.47 (total 5H, m), 3.61 (1H, d, J=12 Hz), 4.20 (1H, d, J=12 Hz), 5.20 (1H, broad res.), 7.20–7.32 (2H, m), 7.46–7.59 (2H, m).

b) 1,2-Dihydro-5-(2-(N,N-dimethylamino)ethyl-(t-butyloxycarbonyl)amino)-1-methyl-3H-1,4-benzodiazepin-2-one Di-5-butyldicarbonate (4.33 g) was added in portions to a stirred, cooled (4° C.) solution of the foregoing benzodiazepine (4.70 g) in dichloromethane (40 ml). After addition the cooling bath was removed and the reaction mixture stirred at room temperature for 16 h. The reaction mixture was evaporated to dryness and the residue purified by column chromatography on neutral alumina (Grade 3) using dichloromethane/methanol (50:1). Mp<35° C. MS, CI$^+$, m/z=361 for (M+H)$^+$. $^1$H NMR (CDCl$_3$) δ1.22 (9H, s), 2.45 (6H, s), 2.68–2.76 (1H, m), 2.79–2.87 (1H, m), 3.53 (3H, s), 3.72 (1H, d, J=11 Hz), 4.02–4.09 (1H, m), 4.24–4.32 (1H, m), 4.65 (1H, d, J=11 Hz), 7.35 (1H, dd, $J_1$=$J_2$=8 Hz), 7.41 (1H, d, J=8 Hz), 7.65 (1H, ddd, $J_1$=2 Hz, $J_2$=$J_3$=8 Hz), 7.79 (1H, dd, $J_1$=2 Hz, $J_2$=8 Hz).

c) 1,2-Dihydro-5-(2-(N,N-dimethylamino)ethyl-(t-butyloxycarbonyl)amino)-1-methyl-3-oximido-3H-1,4-benzodiazepin-2-one Potassium t-butoxide (3.18 g) was added in portions to a stirred, cooled (−20° C.) solution of the foregoing benzodiazepine (3.75 g) in anhydrous toluene (75 ml) under a nitrogen atmosphere. After 15 minutes isopentylnitrite (1.53 ml) was added and the reaction mixture was stirred at −20° C. for 1.5 h. Powdered carbon dioxide (1.6 g) was added in portions and the mixture was stirred for 10 minutes then evaporated to dryness. The residue was purified by column chromatography on neutral alumina (grade 3) using dichloromethane/methanol (30:1) to (10:1) (gradient elution) to afford the oxime (2.50 g). mp 105°–109° C. $^1$H NMR (360 MHz, DMSO-d$_6$) δ1.02 (9H, s), 2.18 and 2.20 (6H, each s), 2.41–2.51 (1H, m), 2.82–2.88 (1H, m), 3.29 and 3.32 (3H, each s), 3.93–3.97 (2H, m), 7.29–7.65 (4H, m), 10.10 and 10.97 (1H, each broad s).

d) 3(R,S)-Amino-1,2-dihydro-5-(2-(N,N-dimethylamino) ethyl-(t-butyloxycarbonyl)amino)-1-methyl-3H-1,4-benzodiazepin-2-one The foregoing oxime (0.50 g) was hydrogenated over 5% rhodium on carbon (0.40 g) in ethanol (50 ml) at 40 psi and 60° C. for 4 h. The reaction mixture was filtered then evaporated to dryness to give the amine (0.462 g). R$_f$ 0.18 in dichloromethane/methanol (5:1) on silica plates. $^1$H NMR (CDCl$_3$) δ1.07 (9H, s), 1.90–2.30 (2H, broad resonance), 2.29 (6H, s), 2.55–2.70 (2H, m), 3.43 (3H, s), 3.87–3.94 (1H, m), 4.10–4.18 (1H, m), 4.29 (1H, s), 7.19–7.29 (2H, m), 7.48–7.66 (2H, m).

e) N-[3(R,S)-2,3-Dihydro-5-(2-(N,N-dimethylamino)ethyl-(t-butyloxycarbonyl)amino)-1-methyl-2-oxo-1H-1,4-benzodiazepin-3-yl]-N'-[3-methylphenyl]urea A stirred, cooled (4° C.) suspension of the foregoing amine (0.45 g) in anhydrous tetrahydrofuran (10 ml) was treated with m-tolylisocyanate (0.145 ml). The cooling bath was removed and the solution was stirred at room temperature for 30 minutes. The reaction mixture was evaporated to dryness and the residue purified by column chromatography on neutral alumina (grade 3) using dichloromethane/methanol (30:1) to afford the title compound which was recrystallised from ethyl acetate/n-hexane (1:5) (0.48 g). mp=112°–115° C. MS, CI$^+$, m/z=509 for (M+H)$^+$. Anal. Found: C, 63.82; H, 7.07; N, 15.80. C$_{27}$H$_{36}$N$_6$O$_4$.0.1C$_6$H$_{14}$ requires C, 64.09; H, 7.28; N, 16.24%.

f) N-[3(R,S)-2,3-Dihydro-5-(2-(N,N-dimethylamino)ethylamino)-1-methyl-2-oxo-1H-1,4-benzodiazepin-3-yl]-N'-[3-methylphenyl]urea dihydrochloride A stirred, cooled (4° C.) solution of the foregoing benzodiazepine (0.18 g) in ethyl acetate (5 ml) was treated with ethyl acetate (20 ml), pre-saturated with hydrogen chloride gas. The solution was stirred at 4° C. for 1 h followed by 1 h at room temperature, then evaporated to dryness. The product was recrystallised from propan-2-ol/diethyl ether (0.10 g). mp 189°–192° C. MS, CI$^+$, m/z=409 for (M+H)$^+$. $^1$H NMR (D$_2$O) δ2.30 (3H, s), 2.98 (6H, s), 3.48 (3H, s), 3.53–3.57 (2H, m), 3.79–3.97 (2H, m), 5.56 (1H, s), 7.02 (1H, d, J=7.5 Hz), 7.14–7.16 (2H, m), 7.27 (1H, dd, J$_1$=J$_2$=7.5 Hz), 7.55 (1H, dd, J$_1$=J$_2$=8 Hz), 7.62 (1H, d, J=7.5 Hz), 7.86–7.91 (2H, m). Anal. Found: C, 53.89; H, 6.38; N, 16.89. C$_{22}$H$_{28}$N$_6$O$_2$.2HCl.0.6H$_2$O requires C, 53.68; H, 6.39; N, 17.07%.

EXAMPLE 85

N-[3(R,S)-2,3-Dihydro-5-(N-(2-N-morpholinoethyl)-N-methylamino)-1-methyl-2-oxo-1H-1,4-benzodiazepin-3-yl]-N'-[3-methylphenyl]urea Prepared in the same way as Example 77 except using N-methyl-(2-aminoethyl)morpholine. Mp=174° C. (uncorr); $^1$H NMR (DMSO) δ2.10–2.38 (9H, m), 2.43 (1H, m), 2.82 (3H, s), 3.12 (1H, m), 3.32 (3H, s), 3.48 (4H, m), 4.92 (1H, d, J=8.4 Hz), 6.70 (1H, d, J=7.1 Hz), 6.96 (1H, d, J=8.4 Hz), 7.08 (2H, m), 7.17 (1H, s), 7.37 (1H, m), 7.57 (2H, m), 7.63 (1H, m), 8.81 (1H, s); MS (CI) m/e 465 [MH]$^+$. Anal. Found: C, 64.54; H, 6.66; N, 18.04. C$_{25}$H$_{32}$N$_6$O$_3$ requires. C, 64.64; H, 6.94; N, 18.09%.

EXAMPLE 86

N-[3(R,S)-5-(N-Cycloheptyl)-N-methylamino)-2,3-dihydro-1-methyl-2-oxo-1H-1,4-benzodiazepin-3-yl]-N'-[3-(5-methylpyridine)]urea a) 5-(N-Cycloheptyl-N-methylamino)-1-methyl-2-oxo-1,4-benzodiazepine Prepared analogously to Example 1a) from 1-methyl-1,2,3,4-tetrahydro-3H-1,4-benzodiazepin-2,5-dione and N-methyl cycloheptylamine. $^1$H NMR (250 MHz, CDCl$_3$) δ1.0–1.90 (12H, m), 1.96 (1H, m), 2.78 (3H, s), 3.36 (3H, s), 3.48 (1H, d, J=12.2 Hz), 4.23 (1H, d, J=12.2 Hz), 7.24 (2H, m), 7.48 (2H, m).

b) 5-(N-cycloheptyl-N-methylamino)-1-methyl-3-oximino-2-oxo-1,4-benzodiazepine

Prepared analogously to Example 1b).

c) N-[3(R,S)-5-(N-Cycloheptyl)-N-methylamino)-2,3-dihydro-1-methyl-2-oxo-1H-1,4-benzodiazepin-3-yl]-N'-[3-(5-methylpyridine)]urea To the product of part b) (1.9 g) in acetic acid (50 ml) was added trifluoroacetic acid (4.5 ml) and zinc (3.8 g) and the reaction mixture was heated to 40° C. with rapid stirring for 2 hrs. The reaction mixture was cooled to room temperature, filtered through hyflo, evaporated and azeotroped with toluene. The residue was dissolved in dry tetrahydrofuran (10 ml) and added to a solution of 3-amino-5-methyl pyridine (0.63 g), triphosgene (0.57 g) and triethylamine (2.2 ml) in dry tetrahydrofuran (30 ml) and the reaction was allowed to stir at room temperature for 17 hrs. The reaction mixture was concentrated in vacuo and the residue purified by flash column chromatography elution with 0→5% MeOH/0.5% 0.88 ammonia solution/dichloromethane followed by purification on HPLC elution with 0→5% MeOH/0.5% 0.88 ammonia solution/dichloromethane. Product recrystallised from ethyl acetate. mpt=235° C. (uncorr). $^1$H NMR DMSO δ1.18 (1H, m), 1.40 (6H, m), 1.90 (1H, m), 2.21 (3H, s), 2.63 (3H, s), 3.32 (3H, s), 4.93 (1H, d, J=8.3 Hz), 7.07 (1H, d, J=8.3 Hz), 7.37 (1H, m), 7.50 (1H, dd, J=1.4 and 7.8 Hz), 7.61 (3H, m), 7.96 (1H, s), 8.29 (1H, d, J=2.2 Hz), 9.02 (1H, s). MS (CI) m/e 449 [MH]$^+$. Anal. Found C, 66.67; H, 7.19; N, 18.63. C$_{25}$H$_{32}$N$_6$O$_2$ requires C, 66.94; H, 7.19; N, 18.74%.

EXAMPLE 87

3(R,S)-N-(5-(3-Azabicyclo[3,2,2]nonan-3-yl)-2,3-dihydro-1-methyl-2-oxo-1H-1,4-benzodiazepin-3-yl)-1H-indole-2-carboxamide a) 5(3-Azabicyclo[3,2,2]nonan-3-yl)-1,2-dihydro-3H-1-methyl-3-(O-(ethylaminocarbonyl)oximido)-1,4-benzodiazepin-2-one The product of Example 31a) (17.5 g), ethyl isocyanate (7.3 ml) and triethylamine (4.6 ml) were heated at 65° C., with stirring, in anhydrous tetrahydrofuran (900 ml) for 4 hours. The solvent was evaporated and the residue was purified by column chromatography on silica using dichloromethane →2% methanol/dichloromethane (gradient). (20.8 g). mp 168° C.

b) 3(R,S)-Amino-5-(3-azabicyclo[3,2,2-nonan-3-yl)-1,2-dihydro-3H-1-methyl-1,4-benzodiazepin-2-one The foregoing oxime derivative (11.0 g) was hydrogenated in methanol (1L) over 10% palladium on carbon (4.5 g) at 45 psi and ambient temperature for 3 hours. The mixture was filtered and the solvent was evaporated to give the amine as a foam (8.0 g). mp 160°–163° C. (ethyl acetate). Found: C, 68.82; H, 7.67; N, 17.69. C$_{18}$H$_{24}$N$_4$O requires C, 69.20; H, 7.74; N, 17.93%.

c) 3(R,S)-N-(5-(3-Azabicyclo[3,2,2]nonan-3-yl)-2,3-dihydro-1-methyl-2-oxo-1H-1,4-benzodiazepin-3-yl)-1H-indole-2-carboxamide A solution of the foregoing amine (1.50 g) in dimethylformamide (10 ml) was treated with indole-2-carboxylic acid (852 mg), 1-hydroxybenzotriazole (714 mg), 1-(3-dimethyl aminopropyl)-3-ethyl-carbodiimide hydrochloride (1.01 g) and triethylamine (1.4 ml). After stirring for 18 hours at room temperature the solid obtained was collected then triturated with methanol to afford the title compound (1.60 g). mp 210°–214° C. (chloroform/diethyl ether). MS, CI$^+$, m/z=456 for (M+H)$^+$. $^1$H NMR (360 MHz, CDCl$_3$) δ1.44–1.95 (2H, m), 1.95–2.08 (2H, m), 3.26–3.42 (2H, m), 3.44 (3H, s), 3.56–3.70 (2H, m), 5.46 (1H, d, J=8 Hz), 7.06–7.74 (10H, m), 9.22 (1H, broad resonance). Found: C, 69.11; H, 6.34; N, 14.74. $C_{27}H_{29}N_5O_2 \cdot 0.66H_2O$ requires C, 69.36; H, 6.54; N, 14.98%.

EXAMPLE 88

(−)-N-(5-(3-Azabicyclo[3,2,2]nonan-3-yl)-2,3-dihydro-1-methyl-2-oxo-1H-1,4-benzodiazepin-3-yl)-1H-indole-2-carboxamide hydrochloride The racemic compound (Example 87, 1.60 g) was separated into its enantiomers using preparative chiral HPLC on a Pirkle dinitrobenzoylleucine column (5μ) [(250×21.4)mm] eluting with 2% methanol in 1-chlorobutane (including 1% acetic acid). Flow rate 20 ml/minute, U.V. detection at 305 nm. Analysis was performed on an analytical Pirkle dinitrobenzoylleucine column (5μ) [(250×4.6)mm] eluting with 5% methanol in 1-chlorobutane (including 1% acetic add). Flow rate 1.5 ml/minute, U.V. detection at 250 nm.

The free base was liberated and obtained as a colourless solid (780 mg). The hydrochloride salt had mp 280°–282° C. (chloroform). MS, CI$^+$, m/z=456for (M+H)$^+$. $[\alpha]^{23°\ C.}_D = -253°$ (c=0.2, methanol). HPLC:>99% ee. Found: C, 65.86; H, 6.15; N, 14.44; Cl6.87. $C_{27}H_{29}N_5O_2 \cdot HCl$ requires C, 65.91; H, 6.14; N, 14.23; Cl7.20%.

EXAMPLE 89

(+)-N-(5-(3-Azabicyclo[3,2,2]nonan-3-yl)-2,3-ihydro-1-methyl-2-oxo-1H-1,4-benzodiazepin-3-yl)-1H-indole-2-carboxamide dihydrochloride The title compound was obtained (800 mg) using the procedure described in Example 88. The dihydrochloride salt had mp 279°–280° C. (chloroform). MS, CI$^+$, m/z=456 for (M+H)$^+$. $[\alpha]^{23°\ C.}_D = +222°$ (c=0.2, methanol). HPLC: 93% ee. Found: C, 59.73; H, 5.60; N, 12.55; Cl,15.34. $C_{27}H_{29}N_5O_2 \cdot 2.4HCl$ requires C, 59.72; H, 5.83; N, 12.90; Cl, 15.67%.

EXAMPLE 90

3(R,S)-N-(2,3-Dihydro-5-(homopiperidin-1-yl)-1-(2-methylpropyl)-2-oxo-1H-1,4-benzodiazepin-3-yl)-1H-indole-2-carboxamide a) 1,2-Dihydro-3H-5-(homopiperidin-1-yl)-1-(2-methylpropyl)-1,4-benzodiazepin-2-one The title compound was prepared from 1-(2-methylpropyl)-1,2,3,4-tetrahydro-3H-1,4-benzodiazepin-2,5-dione, phosphorus pentachloride and homopiperidine. mp>210° C. (dec.). Found: C, 71.88; H, 8.70; N, 12.95. $C_{19}H_{27}N_3O \cdot 0.25H_2O$ requires C, 71.78; H, 8.72; N, 13.22%.

b) 1,2-Dihydro-3H-5-(homopiperidin-1-yl)-1-(2-methylpropyl)-3-oximido-1,4-benzodiazepin-2-one The title compound was prepared from the foregoing benzodiazepine, potassium t-butoxide and isopentylnitrite in toluene.

c) 3(R,S)-Amino-1,2-dihydro-3H-5-(homopiperidin-1-yl)-1-(2-methylpropyl)-1,4-benzodiazepin-2-one The title compound was prepared from the foregoing oxime using previously described procedures.

d) 3(R,S)-N-(2,3-Dihydro-5-(homopiperidin-1-yl)-1-(2-methylpropyl)-2-oxo-1H-1,4-benzodiazepin-3-yl)-1H-indole-2-carboxamide The title compound was obtained from the foregoing amine, indole-2-carboxylic acid, 1-hydroxybenzotriazole, 1-(3-dimethylaminopropyl)-3-ethyl-carbodiimide hydrochloride and triethylamine in dimethylformamide. mp>264° C. Found: C, 71.47; H, 7.02; N, 15.14. $C_{28}H_{33}N_5O_2$ requires C, 71.31; H, 7.05; N, 14.85%.

EXAMPLE 91

(−)-N-[2,3-Dihydro-5-(homopiperidin-1-yl)-1-(2-methylpropyl)-2-oxo-1H-1,4-benzodiazepin-3-yl)-1H-indole-2-carboxamide The racemate of Example 90 was separated into its enantiomers using a semi-preparative dinitrobenzoylleucine Pirkle column (5μ) [(250×20)mm] eluting with 3% methanol in 1-chlorobutane (including 1% acetic acid). The free base was liberated and obtained as a colourless solid. mp 243°–246° C. $[\alpha]^{23°\ C.}_D = -17°$ (c=0.2, methanol). Found: C, 71.56; H, 6.97; N, 14.80. $C_{28}H_{33}N_5O_2$ requires C, 71.31; H, 7.05; N, 14.85%.

EXAMPLE 92

(+)-N-(2,3-Dihydro-5-(homopiperidin-1-yl)-1-(2-methylpropyl)-2-oxo-1H-1,4-benzodiazepin-3-yl)-1H-indole-2-carboxamide Obtained as for Example 91. mp 240°–241° C. $[\alpha]^{23°\ C.}_D = +15°$ (c=0.2, methanol). Found: C, 65.91; H, 6.77; N, 13.36. $C_{28}H_{33}N_5O_2 \cdot 2H_2O$ requires C, 66.25; H, 7.35; N, 13.80%.

EXAMPLE 93

3(R,S)-N-(2,3-Dihydro-5-(homopiperidin-1-yl)-1-(2-methylpropyl)-2-oxo-1H-1,4-benzodiazepin-3-yl)-(2S)-indoline-2-carboxamide Prepared analogously to Example 87 from 3(R,S)-amino-1,2-dihydro-3H-5-(homopiperidin-1-yl)-1-(2-methylpropyl)1,4-benzodiazepin-2-one and (S)-(−)-indoline-2-carboxylic acid. mp 105°–106° C. Found: C, 70.26; H, 7.24; N, 14.14. $C_{28}H_{35}N_5O_2 \cdot 0.4H_2O$ requires C, 69.94; H, 7.51; N, 14.57%.

EXAMPLE 94

3(R,S)-N-(2,3-Dihydro-5-(homopiperidin-1-yl)-1-(2-methylpropyl)-2-oxo-1H-1,4-benzodiazepin-3-yl)-1H-indole-3-acetamide Prepared analogously to Example 87 from (R,S)-amino-1,2-dihydro-3H-5-(homopiperidin-1-yl)-1-(2-methylpropyl)-1,4-benzodiazepin-2-one and indole-3-acetic acid. mp 178°–180° C. Found: C, 72.11; H, 7.10; N, 14.45. $C_{29}H_{35}N_5O_2$ requires C, 71.72; H, 7.26; N, 14.42%.

EXAMPLE 95

3(R,S)-N-(2,3-Dihydro-5-(4-methylpiperidin-1-yl)-1-(2-methylpropyl)-2-oxo-1H-1,4-benzodiazepin-3-yl)-1H-indole-2-carboxamide a) 1,2-Dihydro-3H-5-(4-methylpiperidin-1-yl)-1-(2-methylpropyl)-1,4-benzodiazepin-2-one Prepared from 1-(2-methylpropyl)-1,2,3,4-tetrahydro-3H-1,4-benzodiazepin-2,5-dione, phosphorus pentachloride and 4-methylpiperidine. Rf 0.76 in dichloromethane/methanol (9:1) on silica plates. MS, CI$^+$, m/z=314 [M+H]$^+$.

b) 1,2-Dihydro-3H-5-(4-methylpiperidin-1-yl)-3-oximido-1,4-benzodiazepin-2-one

Prepared from the foregoing benzodiazepine, potassium t-butoxide and isopentylnitrite in toluene. mp 188°–191° C. (ethyl acetate/n-hexane). MS, CI$^+$, m/z=343 [M+H]$^+$. $^1$H NMR (360 MHz, CDCl$_3$) δ0.81–1.10 and 1.20–2.00 (14H, each m), 2.80–3.00 (1H, m), 3.10–3.35 (1H, m), 3.34 (1H, dd, J$_1$=6 Hz, J$_2$=14 Hz), 3.60–3.90 (2H, m), 4.34 (1H, dd, J$_1$=9 Hz, J$_2$=14 Hz), 4.44–5.00 (1H, m), 7.12–7.48 (4H, m).

c) 1,2-Dihydro-3-(O-(ethylaminocarbonyl)-oximido)-3H-5-(4-methylpiperidin-1-yl)-1-(2-methylpropyl)-1,4-benzodiazepin-2-one The foregoing oxime (800 mg) was treated with triethylamine (0.2 ml) and ethyl isocyanate (0.37 ml) in anhydrous tetrahydrofuran (80 ml) then heated at reflux for 4 hours. The reaction mixture was cooled, evaporated to dryness to give a cream foam (960 mg). mp 75°–79° C. MS, CI$^+$, m/z 414 for [M+H]$^+$.

d) 3(R,S)-Amino-1,2-dihydro-3H-5-(4-methylpiperidin-1-yl)-1-(2-methylpropyl)-1,4-benzodiazepin-2-one The foregoing carbamate-oxime (960 mg) was hydrogenated at 45 psi over 10% palladium on charcoal (960 mg) in ethyl acetate (120 ml) for 5 hours. The reaction mixture was filtered, then evaporated to dryness to give the amine (725 mg). Rf 0.28 in dichloromethane/methanol (9:1) on silica plates.

e) 3(R,S)-N-(2,3-Dihydro-5-(4-methylpiperidin-1-yl)-1-(2-methylpropyl)-2-oxo-1H-1,4-benzodiazepin-3-yl)-1H-indole-2-carboxamide A stirred solution of the foregoing amine (725 mg) in dimethylformamide (10 ml) was treated with 1-(3-dimethylaminopropyl)-3-ethyl-carbodiimide hydrochloride (497 mg), 1-hydroxybenzotriazole (35 mg), indole-2-carboxylic acid (419 mg) then finally triethylamine (0.72 ml). The reaction mixture was stirred at ambient temperature for 18 hours, treated with water (30 ml), and the resulting solid collected by filtration. The solid was purified through a short silica column using dichloromethane/methanol (20:1) then recrystallised from ethyl acetate/n-hexane (455 mg). mp 248°–249° C. MS, CI$^+$, m/z=472 [M+H]$^+$. Found: C, 71.79; H, 7.01; N, 14.58. C$_{28}$H$_{33}$N$_5$O$_2$ requires C, 71.31; H, 7.05; N, 14.85%.

EXAMPLE 96

N-[3(R,S)-2,3-Dihydro-1-methyl-5-(4-methylpiperidin-1-yl)-2-oxo-1H-1,4-benzodiazepin-3-yl]N'-[3-(N-methyl-N'-piperazinyl)phenyl]urea a) 1,2-Dihydro-1-methyl-5-(4-methylpiperidin-1-yl)-3-O-ethylaminocarbonyl)oximido-3H-1,4-benzodiazepin-2-one Prepared analogously to Example 17e from 1,2-dihydro-1-methyl-5-(4-methylpiperidin-1-yl)-3-oximido-3H-1,4-benzodiazepin-2-one (Example 7b, 0.5 g). $^1$H NMR (360 MHz, CDCl$_3$) δ1.00 (3H, brs), 1.13 (3H, t, J=7.2 Hz), 1.22–1.42 (2H, m), 1.54–1.90(3H, m), 2.78–3.30 (4H, m), 3.44 (3H, s), 3.56–3.78 (1H, m), 4.54–4.86 (1H, m), 6.37–6.45 (1H, m), 7.21–7.38 (3H, m), 7.46–7.54 (1H, m).

b) 3-(N-Methyl-N'-piperazinyl)-1-nitrobenzene

A mixture of N-methylbis (2-chloroethyl)amine hydrochloride (9.8 g) and 3-nitroaniline (7.0 g) in 1-butanol (100 ml) was heated at reflux for 60 h then cooled to room temperature. Sodium carbonate (2.8 g) was then added and the mixture heated at reflux for a further 18 h, then cooled to 0° C. and filtered. The solid was collected, washed with anhydrous ether then partitioned between dichloromethane (200 ml) and sodium hydroxide solution (1M, 150 ml). The organic layer was separated and the aqueous phase washed once more with dichloromethane (200 ml). The combined organic layers were dried (K$_2$CO$_3$) and evaporated in vacuo. The resultant residue was chromatographed on silica gel, using dichloromethane:methanol (96:4) as the eluant, to afford an orange oil. The oil crystallised on standing and the resultant solid was triturated with petrol (60/80) to give the desired piperazine (5.64 g). $^1$H NMR (360 MHz, CDCl$_3$) δ2.37 (3H, s), 2.58 (4H, t, J=5 Hz), 3.30 (4H, t, J=5 Hz), 7.18 (1H, dd, J=9 and 3 Hz), 7.35 (1H, t, J=8 Hz), 7.64 (1H, dd, J=9 and 2 Hz), 7.71 (1H, d, J=2 Hz). MS (CI, NH$_3$) 222 (M+1).

c) 1-Amino-3-(N-methyl-N'-piperazinyl)benzene

A solution of 3-(N-methyl-N-piperazinyl)-1-nitrobenzene (1.17 g) in ethanol (40 ml) was hydrogenated at 25 psi for 20 min in the presence of a palladium on carbon catalyst (200 mg, 17% (w/w)). The catalyst was filtered off and the solvent evaporated in vacuo. The residue was chromatographed on silica gel, using a gradient elution of petrol:ether (1:1 ) followed by dichloromethane:methanol (95:5) to give a colourless oil, which was azeotroped with toluene (20 ml) then left at 0° C. overnight. After this time the oil had crystallized, and after trituration with petrol (60/80) the desired aniline (0.86 g) was isolated as a white solid. $^1$H NMR (360 MHz, CDCl$_3$) δ2.34 (3H, s), 2.55 (4H, t, J=5 Hz), 3.18 (4H, t, J=5 Hz), 3.60 (2H, brs), 6.20 (1H, dd, J=8 and 2 Hz), 6.25 (1H, t, J=2 Hz), 6.36 (1H, dd, J=8 and 2 Hz), 7.04 (1H, t, J=8 Hz). MS (CI, NH$_3$) 192 (M+1).

d) N-[3(R,S)-2,3-Dihydro-1-methyl-5-(4-methylpiperidin-1-yl)-2-oxo-1H-1,4-benzodiazepin-3-yl]N'-[3-(N-methyl-N'-piperazinyl)phenyl]urea To a solution of the product of part a) (0.62 g) in methanol (30 ml) was added 10% palladium on carbon (0.2 g, 32% (w/w)). The mixture was hydrogenated at 40 psi for 2 h. Further 10% palladium on carbon (0.1 g, 16% (w/w)) was added and the mixture hydrogenated at 40 psi for another 1 h. The catalyst was then filtered off and washed with methanol. The solvent was evaporated in vacuo to give the amine (0.48 g).

To a solution of 1-amino-3-(N-methyl-N'-piperazinyl) benzene (0.48 g) in anhydrous tetrahydrofuran (30 ml) cooled to 0° C. under an atmosphere of nitrogen was added triphosgene (0.25 g). Triethylamine (1.0 ml) was added dropwise. After stirring at 0° C. for 30 min a solution of the amine (0.48 g) in anhydrous tetrahydrofuran (10 ml) was added dropwise. The mixture was stirred at 0° C. for 5 min and then allowed to warm to ambient temperature and stirred for 10 min. The solvent was evaporated in vacuo and the residue partitioned between ethyl acetate (50 ml) and water (50 ml). The undissolved solid was collected by filtration and purified by chromatography on silica gel using 95:5:1, dichloromethane:methanol:aqueous ammonia solution increasing the ratio to 90:10:1, to give the title compound (0.55 g). Mp 160° C. (dec.). $^1$H NMR (360 MHz, CDCl$_3$) δ0.95 (3H, d, J=6.2 Hz), 1.05–1.21 (1H, m), 1.28–1.37 (1H, m), 1,46–1.62 (2H, m), 1.64–1.74 (1H, m), 2.45 (3H, s), 2.57–2.80 (6H, m), 3.25–3.35 (4H, m), 3.41 (3H, s), 3.47–3.60 (1H, m), 3.86–3.96 (1H, m), 5.26 (1H, d, J=7.8 Hz), 6.52–6.58 (2H, m), 6.65 (1H, d, J =7.9 Hz), 6.98 (1H, brs), 7.11 (1H, t, J=8.1 Hz), 7.16–7.20 (1H, m), 7.21–7.33 (2H, m), 7.47–7.55 (2H, m).

EXAMPLE 97A

Tablets containing 1–25 mg of compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 97B

Tablets containing 26–100 mg of compound

|  | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 98

Parenteral injection

|  | Amount mg |
|---|---|
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 99

Topical formulation

|  | Amount mg |
|---|---|
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

The CCK-A and CCK-B antagonising activity of the compounds described herein was evaluated using the assays described in published European patent application no. 0514133. The method essentially involves determining the concentration of the test compound required to displace 50% of the specific $^{125}$I-CCK from rat pancreas (CCK-A) or guinea pig brain (CCK-B). The data in Table 1 were obtained for compounds of the Examples.

TABLE I

| CCK RECEPTOR BINDING RESULTS IC$_{50}$ (nM) | | |
|---|---|---|
| Compound of Ex # | $^{125}$I-CCK Pancreas | $^{125}$I-CCK Brain |
| 1 | 724 | 14.8 |
| 2 | 871 | 2.02 |
| 3 | 544 | 11.6 |
| 4 | 35 | 1.19 |
| 5 (enantiomer A) | 738 | 0.49 |
| 5 (enantiomer B) | 7.8 | 14.8 |
| 6 | 235 | 10.9 |
| 7 | 7.74 | 1.64 |
| 8 (enantiomer A) | 981 | 0.35 |
| 8 (enantiomer B) | 2.61 | 23.2 |
| 9 | 8.97 | 0.21 |
| 10 (enantiomer A) | 421 | 0.76 |
| 10 (enantiomer B) | 0.42 | 12.6 |
| 11 | 25.2 | 4.22 |
| 12 | 2180 | 0.28 |
| 13 | 496 | 1.53 |
| 14 (enantiomer A) | 3220 | 11.6 |
| 14 (enantiomer B) | 11.4 | 174 |
| 15 (enantiomer A) | 1902 | 3.47 |
| 15 (enantiomer B) | 163 | 75 |
| 16 | 2650 | 19.1 |
| 17 | 27.2 | 0.2 |
| 18 (enantiomer A) | 765 | 0.64 |
| 20 (enantiomer A) | 3294 | 1.52 |
| 20 (enantiomer B) | 40 | 44 |
| 22 (enantiomer A) | 3670 | 32.9 |
| 24 (enantiomer A) | 2250 | 0.927 |
| 24 (enantiomer B) | 46 | 50 |
| 26 | >3000 | 0.27 |
| 27 | 15 | 33 |
| 28 (enantiomer A) | 239 | 27.8 |
| 28 (enantiomer B) | 3.97 | 281 |
| 30 | 347 | 0.36 |
| 31 | 20 | 0.53 |
| 32 | >3000 | 22 |
| 33 | 1604 | 0.10 |
| 34 | 6.46 | 26.7 |
| 35 | 39.6 | 0.82 |
| 36 | 1400 | 0.32 |
| 37 | 9 | 144 |
| 38 | 7.93 | 0.71 |
| 39 | 4010 | 0.17 |
| 40 | 8.8 | 36.3 |
| 41 | >3000 | 0.37 |
| 42 | 80.4 | 1.79 |
| 43 | >3000 | 48.3 |
| 44 | 70.2 | 0.52 |
| 45 | >3000 | 0.42 |
| 46 | 23.7 | 20.1 |
| 47 | 26.6 | 1.01 |
| 48 | 2418 | 1.11 |
| 49 | 9.65 | 82.7 |
| 50 | 10 | 3.9 |
| 51 | 28.5 | 5.49 |
| 52 | 18.5 | 0.25 |
| 53 | 3760 | 0.18 |
| 54 | 8.4 | 68 |
| 55 | >3000 | 0.73 |
| 56 | 62 | 47 |
| 57 | 12.3 | 4.6 |
| 58 | 2260 | 2.0 |
| 59 | 9.7 | 144 |
| 60 | 186 | 2.56 |
| 61 | 704 | 0.22 |
| 62 | 114 | 35.2 |
| 63 | 304 | 1.36 |
| 64 | 2065 | 0.22 |
| 65 | 138 | 13.7 |

TABLE I-continued

CCK RECEPTOR BINDING RESULTS IC$_{50}$ (nM)

| Compound of Ex # | $^{125}$I-CCK Pancreas | $^{125}$I-CCK Brain |
|---|---|---|
| 66 | 83.6 | 0.79 |
| 67 | 1999 | 0.10 |
| 68 | 53.4 | 26.6 |
| 69 | 469 | 2.82 |
| 70 | >3000 | 0.61 |
| 71 | 145 | 86 |
| 72 | 176 | 10.3 |
| 73 | >3000 | 1410 |
| 74 | 192 | 7.3 |
| 75 | 314 | 46.9 |
| 76 | 760 | 3.12 |
| 77 | 135 | 81.1 |
| 78 | 891 | 4.5 |
| 79 | 1700 | 13.4 |
| 80 | 1135 | 32.4 |
| 81 | 14.9 | 23.2 |
| 82 | 815 | 0.47 |
| 83 | 283 | 3.67 |
| 84 | >3000 | 1900 |
| 85 | >3000 | 785 |
| 86 | 831 | 31.3 |
| 87 | 0.87 | 509 |
| 88 | 393 | 66 |
| 89 | 0.26 | 653 |
| 90 | 8.7 | 225 |
| 93 | 101 | 348 |
| 94 | 646 | 119 |
| 95 | 11.6 | 161 |
| 96 | 94.1 | 148 |

We claim:

1. A compound of formula (I), or a pharmaceutically acceptable salt or prodrug thereof:

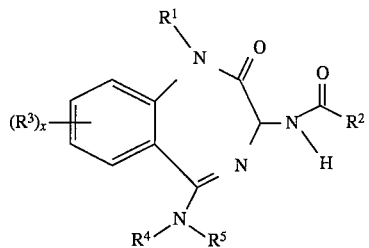

wherein:

R$^1$ represents C$_{1-6}$alkyl, C$_{3-7}$cycloalkyl, cyclopropylmethyl, CH$_2$CO$_2$R$^{11}$ (wherein R$^{11}$ is C$_{1-4}$alkyl) or a group CH$_2$CONR$^6$R$^7$ (where R$^6$ and R$^7$ each independently represents H or C$_{1-4}$alkyl, or R$^6$ and R$^7$ together from a chain (CH$_2$)p where p is 4 or 5);

R$^2$ represents NHR$^{12}$;

R$^{12}$ represents a phenyl group optionally substituted by one or more substituents selected from C$_{1-6}$alkyl, halo, hydroxy, (CH$_2$)$_q$-tetrazolyl optionally substituted in the tetrazole ring by C$_{1-4}$alkyl, (CH$_2$)q-imidazolyl, (CH$_2$)q-triazolyl (where q is 0, 1, 2 or 3), 5-hydroxy-4-pyrone, NR$^6$R$^7$, NR$^9$COR$^{11}$, NR$^9$CONR$^{9'}$R$^{11}$ (where R$^9$ and R$^{9'}$ are each independently H or C$_{1-4}$alkyl and R$^{11}$ is as previously defined), CONR$^6$R$^7$ (where R$^6$ and R$^7$ are as previously defined), SO(C$_{1-6}$alkyl), SO$_2$(C$_{1-6}$alkyl), trifluoromethyl, CONHSO$_2$R$^8$, SO$_2$NHCOR$^8$ (where R$^8$ is C$_{1-6}$alkyl, optionally substituted aryl, 2,2-difluorocyclopropane or trifluoromethyl), SO$_2$NHR$^{10}$ (where R$^{10}$ is a nitrogen containing heterocycle), B(OH)$_2$, (CH$_2$)$_t$CO$_2$H, where t is zero, 1 or 2; or R$^{12}$ represents a group

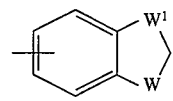

where W represents CH$_2$ or NR$^9$, where R$^9$ is as previously defined and W$^1$ represents CH$_2$, or W and W$^1$ both represent oxygen;

R$^3$ represents C$_{1-6}$alkyl, halo or NR$^6$R$^7$, where R$^6$ and R$^7$ are as previously defined;

x is 0, 1, 2, or 3 and NR$^4$R$^5$ represents a group

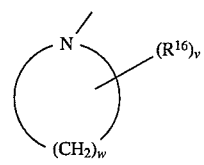

wherein each R$^{16}$ independently represents C$_{1-6}$alkyl, C$_{1-6}$alkoxy, hydroxy, oxo, SR$^{11}$, NR$^6$R$^7$, NR$^9$C$_{1-4}$alkylR$^{17}$, =NOR$^9$ or

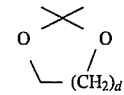

where R$^{11}$, R$^6$, R$^7$ and R$^9$ are as previously defined, R$^{17}$ is halo or trifluoromethyl, and d is 2 or 3; v is 1, 2, 3, 4, 5, 6, 7 or 8; and w is 4, 5, 6, 7, 8, 9, 10 or 11.

2. A compound as claimed in claim 1 wherein R$^{12}$ represents a phenyl group optionally substituted by one or more substituents selected from C$_{1-6}$alkyl, halo, hydroxy, C$_{1-4}$alkoxy, (CH$_2$)$_q$-tetrazolyl optionally substituted in the tetrazole ring by C$_{1-4}$alkyl, (CH$_2$)$_q$-imidazolyl, (CH$_2$)$_q$triazolyl, 5-hydroxy-4-pyrone, NR$^6$R$^7$, NR$^9$COR$^{11}$, NR$^9$COR$^{9'}$R$^{11}$, CONR$^6$R$^7$, SO(C$_{1-6}$alkyl), SO$_2$(C$_{1-6}$alkyl), trifluoromethyl, CONHSO$_2$R$^8$, SO$_2$NHCOR$^8$, SO$_2$NHR$^{10}$, B(OH)$_2$ and (CH$_2$)$_t$CO$_2$H; or R$^{12}$ represents a group

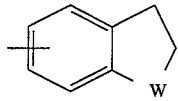

where W represents CH$_2$ or NR$^9$;

R$^{16}$ represents C$_{1-6}$alkyl, C$_{1-6}$alkoxy, hydroxy, oxo, SR$^{11}$, NR$^6$R$^7$, NR$^9$C$_{1-4}$alkylR$^{17}$, =NOR$^9$ or

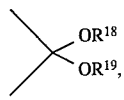

where R$^{18}$ and R$^{19}$ each independently represent C$_{1-4}$alkyl or R$^{18}$ and R$^{19}$ together form a chain CH$_2$CH$_2$ or CH$_2$CH$_2$CH$_2$;

and v is 1.

3. A compound as claimed in claim 1 selected from:

N-[3(R,S)-2,3-dihydro-5-(1,4-dioxa-8-azaspiro[4.5]decan-8-yl)-2-oxo-1-propyl-1H-1,4-benzodiazepin-3-yl]-N'-[3-methylphenyl]urea;

N-[3(R,S)-2,3-dihydro-2-oxo-5-(4-oxopiperidin-1-yl)-2-oxo-1-propyl-1H-1,4-benzodiazepin-3-yl]N'-[3-methylphenyl]urea;

N-[3(R,S)-2,3-dihydro-2-oxo-1-propyl-5-(4-[1,1,1-trifluoroethylamine]piperidin-1-yl)-1H-1,4-benzodiazepin-3-yl]N'-[3-methylphenyl]urea;

N-[3(R,S)-2,3-dihydro-5-(cis-2,6-dimethylpiperidin-1-yl)-1-methyl-2-oxo-1H-1,4-benzodiazepin-3-yl]N'-[indan-5-yl]urea;

and pharmaceutically acceptable salts thereof.

4. A compound as claimed in claim 1 selected from:

N-[3(R,S)-2,3-dihydro-5-(4,4-dimethylpiperidin-1-yl)-1-methyl-2-oxo-1H-1,4-benzodiazepin-3-yl]N'-[indan-5-yl]urea;

(−)-N-[2,3-dihydro-5-(4,4-dimethylpiperidin-1-yl)-1-methyl-2-oxo-1H-1,4-benzodiazepin-3-yl]N'-[indan-5-yl]urea;

(+)-N-[2,3-dihydro-5-(4,4-dimethylpiperidin-1-yl)-1-methyl-2-oxo-1H-1,4-benzodiazepin-3-yl]N'-[indan-5-yl]urea; and pharmaceutically acceptable salts thereof.

5. A pharmaceutical composition comprising a compound as claimed in claim 1 in association with a pharmaceutically acceptable carrier.

6. A method for the treatment or prevention of a physiological disorder involving CCK and/or gastrin, which method comprises administration to a patient in need thereof a CCK and/or gastrin reducing amount of a compound according to claim 1.

7. A method as claimed in claim 6 for the treatment or prevention of anxiety.

8. A method as claimed in claim 6 for the treatment or prevention of panic.

9. A method as claimed in claim 6 for the treatment or prevention of pain.

10. A compound of formula (I), or a salt or prodrug thereof:

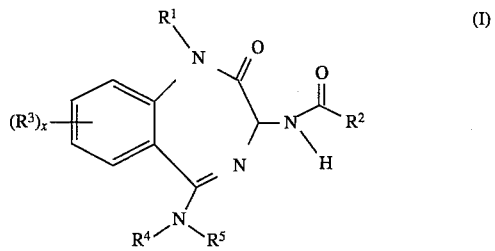

wherein:

$R^1$ represents H, $C_{1-6}$ alkyl, $C_{3-7}$ cloalkyl, cyclopropylmethyl, $(CH_2)_r$imidazolyl, $(CH_2)_r$triazolyl, $(CH_2)_r$tetrazolyl (where r is 1, 2 or 3), $CH_2CO_2R^{11}$ (where $R^{11}$ is $C_{1-4}$alkyl) or a group $CH_2CONR^6R^7$ (where $R^6$ and $R^7$ each independently represents H or $C_{1-4}$ alkyl, or $R^6$ and $R^7$ together form a chain $(CH_2)_p$ where p is 4 or 5);

$R^2$ represents $NHR^{12}$;

$R^{12}$ represents a phenyl group optionally substituted by one or more substituents selected from $C_{1-6}$ alkyl, halo, hydroxy, $C_{1-4}$ alkoxy, $(CH_2)_q$-tetrazolyl optionally substituted in the tetrazole ring by $C_{1-4}$ alkyl, $(CH_2)_q$-imidazolyl, $(CH_2)_q$-triazolyl (where q is 0, 1, 2 or 3), 5-hydroxy-4-pyrone, $NR^6R^7$, $NR^9COR^{11}$, $NR^9CONR^{9'}R^{11}$ (where $R^9$ and $R^{9'}$ are each independently H or $C_{1-4}$ alkyl and $R^{11}$ is as previously defined), $CONR^6R^7$ (where $R^6$ and $R^7$ are as previously defined), $SO(C_{1-6}$ alkyl), $SO_2(C_{1-6}$ alkyl), trifluoromethyl, $CONHSO_2R^8$, $SO_2NHCOR^8$ (where $R^8$ is $C_{1-6}$ alkyl, optionally substituted aryl, 2,2-difluorocyclopropane or trifluoromethyl), $SO_2NHR^{10}$ (where $R^{10}$ is a nitrogen containing heterocycle), $B(OH)_2$, $(CH_2)_qCO_2H$, where q is as previously defined; or $R^{12}$ represents a group

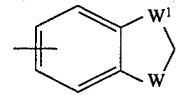

where W represents $CH_2$ or $NR^9$, and $R^9$ is as previously defined, and $W^1$ represents $CH_2$, or W and $W^1$ each represent oxygen;

$R^3$ represents $C_{1-6}$ alkyl, halo or $NR^6R^7$, where $R^6$ and $R^7$ are as previously defined; $R^4$ and $R^5$ together with the nitrogen to which they are attached form a residue of a bridged azabicyclic system;

x is 0, 1, 2 or 3.

11. A compound as claimed in claim 10 wherein $R^1$ represents $C_{1-6}$alkyl, $C_{3-7}$cycloalkyl, cyclopropylmethyl, $CH_2CO_2R^{11}$ or $CH_2CONR^6R^7$; and $R^{12}$ represents a phenyl group optionally substituted by one or more substituents selected from $C_{1-6}$alkyl, halo, hydroxy, $C_{1-4}$alkoxy, $(CH_2)_q$tetrazolyl optionally substituted in the tetrazole ring by $C_{1-4}$alkyl, $(CH_2)_q$imidazolyl, $(CH_2)_q$triazolyl, 5-hydroxy-4-pyrone, $NR^6R^7$, $NR^9COR^{11}$, $NR^9COR^{9'}R^{11}$, $CONR^6R^7$, $SO(C_{1-6}$alkyl), $SO_2(C_{1-6}$alkyl), trifluoromethyl, $CONHSO_2R^8$, $SO_2NHCOR^8$, $SO_2NHR^{10}$, $B(OH)_2$ and $(CH_2)_tCO_2H$, where t is zero, 1 or 2; or $R^{12}$ represents a group

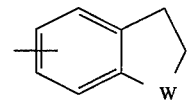

where W represents $CH_2$ or $NR^9$.

12. A compound as claimed in claim 10 selected from:

N-[3(R,S)-2,3-dihydro-5-((1S,4S)-5-methyl-2,5-diazabicyclo[2.2.1]heptan-2-yl]-2-oxo-1-propyl-1H-1,4-benzodiazepin-3-yl]N'-[3-methylphenyl]urea;

N-[3(R,S)-5-(3-azabicyclo[3.2.2]nonan-3-yl)-2,3-dihydro-1-methyl-2-oxo-1H-1,4-benzodiazepin-3-yl]N'-[3-fluorophenyl]urea;

(−)-N-[5-(3-azabicyclo[3.2.2]nonan-3-yl)-2,3-dihydro-1-methyl-2-oxo-1H-1,4-benzodiazepin-3-yl]N'-[3-fluorophenyl]urea;

(+)-N-[5-(3-azabicyclo[3.2.2]nonan-3-yl)-2,3-dihydro-1-methyl-2-oxo-1H-1,4-benzodiazepin-3-yl]N'-[3-fluorophenyl]urea;

N-[3(R,S)-5-(3-azabicyclo[3.2.1]octan-3-yl)-2,3-dihydro-1-methyl-2-oxo-1H-1,4-benzodiazepin-3-yl]N'-[3-methylphenyl]urea;

(−)-N-[5-(3-azabicyclo[3.2.1]octan-3-yl)-2,3-dihydro-1-methyl-2-oxo-1H-1,4-benzodiazepin-3-yl]N'-[3-methylphenyl]urea;

(+)-N-[5-(3-azabicyclo[3.2.1]octan-3-yl)-2,3-dihydro-1-methyl-2-oxo-1H-1,4-benzodiazepin-3-yl]N'-[3-methylphenyl]urea;

(−)-N-[5-(3-azabicyclo[3.2.2]nonan-3-yl)-2,3-dihydro-1-methyl-2-oxo-1H-1,4-benzodiazepin-3-yl]N'-[5-indanyl]urea;

N-[3(R,S)-5-(3-azabicyclo[3.2.2]nonan-3-yl)-2,3-dihydro-1-methyl-2-oxo-1H-1,4-benzodiazepin-3-yl]N'-[3-trifluoromethylphenyl]urea;

N-[3(R,S)-2,3-dihydro-5-(8-methyl-3,8-diazabicyclo [3.2.1]octan-3-yl)-2-oxo-1-propyl-1H-1,4-benzodiazepin-3-yl]N'-[3-methylphenyl]urea;

N-[3(R,S)-5-(3-azabicyclo[3.2.2]nonan-3-yl)-2,3-dihydro-1-methyl-2-oxo-1H-1,4-benzodiazepin-3-yl]N'-[3-fluoro-4-methylphenyl]urea;

(−)-N-[5-(3-azabicyclo[3.2.2]nonan-3-yl)-2,3-dihydro-1-methyl-2-oxo-1H-1,4-benzodiazepin-3-yl]N'-[3-fluoro-4-methylphenyl]urea;

N-[3(R,S)-5-(2-azabicyclo[2.2.2]octan-2-yl)-2,3-dihydro-1-methyl-2-oxo-1H-1,4-benzodiazepin-3-yl]N'-[3-methylphenyl]urea;

N-[3(R,S)-5-(3-azabicyclo[3.2.2]nonan-3-yl)-2,3-dihydro-1-methyl-2-oxo-1H-1,4-benzodiazepin-3-yl]N'-[4-fluoro-3-methylphenyl]urea;

(−)-N-[5-(3-azabicyclo[3.2.2]nonan-3-yl)-2,3-dihydro-1-methyl-2-oxo-1H-1,4-benzodiazepin-3-yl]N'-[4-fluoro-3-methylphenyl]urea;

(+)-N-[5-(3-azabicyclo[3.2.2]nonan-3-yl)-2,3-dihydro-1-methyl-2-oxo-1H-1,4-benzodiazepin-3-yl]N'-[4-fluoro-3-methylphenyl]urea;

(−)-N-[5-(3-azabicyclo[3.2.2]nonan-3-yl)-2,3-dihydro-1-methyl-2-oxo-1H-1,4-benzodiazepin-3-yl]N'-[3-trifluoromethylphenyl]urea;

(+)-N-[5-(3-azabicyclo[3.2.2]nonan-3-yl)-2,3-dihydro-1-meth 1-2-oxo-1H-1,4-benzodiazepin-3-yl]N'-[3-trifluoromethylphenyl]urea;

(+)-N-[5-(3-azabicyclo[3.2.2]nonan-3-yl)-2,3-dihydro-1-methyl-2-oxo-1H-1,4-benzodiazepin-3-yl]N'-[3-fluoro-4-methylphenyl]urea;

N-[3(R,S)-5-(3-azabicyclo[3.2.2]nonan-3-yl)-2,3-dihydro-1-methyl-2-oxo-1H-1,4-benzodiazepin-3-yl]N'-[3-iodophenyl]urea;

(−)-N-[5-(3-azabicyclo[3.2.2]nonan-3-yl)-2,3-dihydro-1-methyl-2-oxo-1H-1,4-benzodiazepin-3-yl]N'-[3-iodophenyl]urea;

(+)-N-[5-(3-azabicyclo[3.2.2]nonan-3-yl)-2,3-dihydro-1-methyl-2-oxo-1H-1,4-benzodiazepin-3-yl]N'-[3-iodophenyl]urea;

N-[3(R,S)-5-(3-azabicyclo[3.2.2]nonan-3-yl)-2,3-dihydro-1-methyl-2-oxo-1H-1,4-benzodiazepin-3-yl]N'-[phenyl]urea;

and pharmaceutically acceptable salts thereof.

13. A compound as claimed in claim 10 selected from:

N-[3(R,S)-5-(3-azabicyclo[3.2.2]nonan-3-yl)-2,3-dihydro-1-methyl-2-oxo-1H-1,4-benzodiazepin-3-yl]N'-[3-methylphenyl]urea;

(−)-N-[5-(3-azabicyclo[3.2.2]nonan-3-yl)-2,3-dihydro-1-methyl-2-oxo-1H-1,4-benzodiazepin-3-yl]N'-[3-methylphenyl]urea;

(+)-N-[5-(3-azabicyclo[3.2.2]nonan-3-yl)-2,3-dihydro-1-methyl-2-oxo-1H-1,4-benzodiazepin-3-yl]N'-[3-methylphenyl]urea;

and pharmaceutically acceptable salts thereof.

14. A pharmaceutical composition comprising a compound as claimed in claim 10 in association with a pharmaceutically acceptable carrier.

15. A method for the treatment or prevention of a physiological disorder involving CCK and/or gastrin, which method comprises administration to a patient in need thereof a CCK and/or gastrin reducing amount of a compound according to claim 10.

16. A method as claimed in claim 15 for the treatment or prevention of anxiety.

17. A method as claimed in claim 15 for the treatment or prevention of panic.

18. A method as claimed in claim 15 for the treatment or prevention of pain.

\* \* \* \* \*